United States Patent
Gailunas et al.

(10) Patent No.: US 7,589,094 B2
(45) Date of Patent: Sep. 15, 2009

(54) N-(3-AMINO-2-HYDROXY-PROPYL) SUBSTITUTED ALKYLAMIDE COMPOUNDS

(75) Inventors: Andrea Gailunas, Burlingame, CA (US); John A. Tucker, San Mateo, CA (US); Ruth TenBrink, Kalamazoo, MI (US); John Mickelson, Mattawan, MI (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 221 days.

(21) Appl. No.: 11/296,669

(22) Filed: Dec. 7, 2005

(65) Prior Publication Data

US 2006/0194817 A1 Aug. 31, 2006

Related U.S. Application Data

(62) Division of application No. 10/193,044, filed on Jul. 11, 2002, now abandoned.

(60) Provisional application No. 60/304,525, filed on Jul. 11, 2001, provisional application No. 60/308,756, filed on Jul. 30, 2001, provisional application No. 60/341,341, filed on Dec. 17, 2001, provisional application No. 60/341,416, filed on Dec. 17, 2001, provisional application No. 60/344,872, filed on Dec. 21, 2001, provisional application No. 60/380,574, filed on Dec. 21, 2001.

(51) Int. Cl.
C07C 233/35 (2006.01)
A61K 31/164 (2006.01)

(52) U.S. Cl. .............. 514/252.12; 514/617; 544/398; 544/399; 544/400; 544/401; 564/182

(58) Field of Classification Search .......... 564/182; 514/617, 237.8, 252.12, 357, 381, 384, 416, 514/423, 424, 467, 471; 544/168, 398, 399, 544/400, 401; 546/336, 337; 548/253, 264.4, 548/472, 540, 551; 549/72, 451, 494

See application file for complete search history.

(56) References Cited

U.S. PATENT DOCUMENTS 6,211,183 B1  4/2001  Marlowe et al.

FOREIGN PATENT DOCUMENTS

| EP | 0200406 | 12/1986 |
|---|---|---|
| EP | 0580402 | 1/1994 |
| GB | 2184730 | 7/1987 |
| WO | 0202512 | 1/2002 |
| WO | WO 03/040096 | * 5/2003 |

OTHER PUBLICATIONS

Varghese et al., CAPLUS Abstract 138:385173, 2003.*
Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Hartmann et al., PubMed Abstract (J Mol Neurosci. 17(2):171-81), Oct. 2001.*
Janus, PubMed Abstract (CNS Drugs 17(7):457-74), 2003.*

* cited by examiner

*Primary Examiner*—Deepak Rao
(74) *Attorney, Agent, or Firm*—McDonnell Boehnen Hulbert & Berghoff LLP

(57) ABSTRACT

Disclosed are compounds of the formula (I):

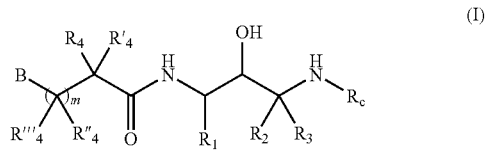

useful in treating Alzheimer's disease and other similar diseases. These compounds include inhibitors of the beta-secretase enzyme that are useful in the treatment of Alzheimer's disease and other diseases characterized by deposition of A beta peptide in a mammal. The compounds of the invention are useful in pharmaceutical compositions and methods of treatment to reduce A beta peptide formation.

7 Claims, No Drawings

N-(3-AMINO-2-HYDROXY-PROPYL) SUBSTITUTED ALKYLAMIDE COMPOUNDS

This application is a divisional of U.S. Ser. No. 10/193,044 filed Jul. 11, 2002 now abandoned, which claims the benefit of U.S. Provisional Patent Application No. 60/304,525, filed Jul. 11, 2001; U.S. Provisional Patent Application No. 60/308,756, filed Jul. 30, 2001; U.S. Provisional Patent Application No. 60/341,341, filed Dec. 17, 2001; U.S. Provisional Patent Application No. 60/341,416, filed Dec. 17, 2001; U.S. Provisional Patent Application No. 60/344,872, filed Dec. 21, 2001; and U.S. Provisional Patent Application No. 60/380,574, filed Dec. 21, 2001.

BACKGROUND OF THE INVENTION

1. Field of the Invention

The invention relates to N-(3-amino-2-hydroxy-propyl)-aryl-, heteroaryl-, cycloalkyl- and heterocyclyl-alkylamide compounds and such compounds that are useful for the treatment of Alzheimer's disease. More specifically, the invention relates to such compounds that are capable of inhibiting beta-secretase, an enzyme that cleaves amyloid precursor protein to produce amyloid beta peptide (A beta), a major component of the amyloid plaques found in the brains of Alzheimer's sufferers.

2. Description of the Related Art

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39-42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sindha et al., 1999, *Nature* 402:537-554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325-327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1-19.

BACE1 knockout mice fail to produce A beta, and present a normal phenotype. When crossed with transgenic mice that over express APP, the progeny show reduced amounts of A beta in brain extracts as compared with control animals (Luo et al., 2001 *Nature Neuroscience* 4:231-232). This evidence further supports the proposal that inhibition of beta-secretase activity and reduction of A beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

The invention provides compounds of formula (I):

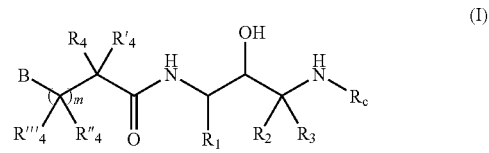

wherein
m is 0-5;

B is aryl or heteroaryl optionally substituted with one, two, three or four groups independently selected from $R_6$, $R'_6$, $R''_6$ and $R'''_6$, or B is cycloalkyl or heterocycloalkyl optionally substituted with one, two, three, four, five, six, seven or eight groups independently selected from $R_{6a}$, $R_{6b}$, $R'_{6a}$, $R'_{6b}$, $R''_{6a}$, $R''_{6b}$, $R'''_{6a}$ and $R'''_{6b}$;

$R_4$ and $R'_4$ independently are H, —NRR', —SR, —CN, —OCF$_3$, —CF$_3$, —CONRR', —CO$_2$R, —SO$_2$NRR', —O—P(=O)(OR)(OR'), —N(R)—C(=O)(R'), —N(R)(SO$_2$R'), —SO$_2$R, —C(=O)R, —NO$_2$, halogen, —(CH$_2$)$_{0-4}$-aryl, —(CH$_2$)$_{0-4}$-heteroaryl, or $C_1$-$C_8$ alkyl, $C_2$-$C_7$ alkenyl or $C_2$-$C_7$ alkynyl, each of which is optionally substituted with one, two or three groups selected from —NRR', —SR, —CN, —OCF$_3$, —CF$_3$, —CONRR', —CO$_2$R, —SO$_2$NRR', —O—P(=O)(OR)(OR'), —N(R)—C(=O)(R'), —N(R)(SO$_2$R'), —SO$_2$R, —C(=O)R, —NO$_2$, halogen, —(CH$_2$)$_{0-4}$-aryl, and —(CH$_2$)$_{0-4}$-heteroaryl, or $R_4$ and $R'_4$ together are oxo;

$R''_4$ and $R'''_4$ independently are H, —OR, —NRR', —SR, —CN, —OCF$_3$, —CF$_3$, —CONRR', —CO$_2$R, —SO$_2$NRR', —O—P(=O)(OR)(OR'), —N(R)—C(=O)(R'), —N(R)(SO$_2$R'), —SO$_2$R, —C(=O)R, —NO$_2$, halogen, —(CH$_2$)$_{0-4}$-aryl, —(CH$_2$)$_{0-4}$-heteroaryl, or $C_1$-$C_8$ alkyl, $C_2$-$C_7$ alkenyl or $C_2$-$C_7$ alkynyl, each of which is optionally substituted with one, two or three groups selected from —OR, —NRR', —SR, —CN, —OCF$_3$, —CF$_3$, —CONRR', —CO$_2$R, —SO$_2$NRR', —O—P(=O)(OR)(OR'), —N(R)—C(=O)(R'), —N(R)(SO$_2$R'), —SO$_2$R, —C(=O)R, —NO$_2$, halogen, —(CH$_2$)$_{0-4}$-aryl, and —(CH$_2$)$_{0-4}$-heteroaryl, or $R''_4$ and $R'''_4$ together are oxo;

R and R' independently are —H, —($C_1$-$C_{10}$) alkyl, —(CH$_2$)$_{0-4}$—$R_{aryl}$, —(CH$_2$)$_{0-4}$—$R_{heteroaryl}$, —(CH$_2$)$_{0-4}$—$R_{heterocyclyl}$, or $C_2$-$C_7$ alkenyl or $C_2$-$C_7$ alkynyl, each of which is optionally substituted with one, two or three substituents selected from the group consisting of halogen, —OH, —SH, —C≡N, —CF$_3$, $C_1$-$C_3$ alkoxy, amino, mono- or dialkylamino, and $C_1$-$C_6$ alkyl, or —(CH$_2$)$_{0-4}$—$C_3$-$C_7$ cycloalkyl optionally substituted with one, two or three substituents selected from the group consisting of halogen, —OH, —SH, —C≡N, —CF$_3$, $C_1$-$C_3$ alkoxy, amino, mono- or dialkylamino, and $C_1$-$C_6$ alkyl;

$R_1$ is —(CH$_2$)$_{1-2}$—S(O)$_{0-2}$—($C_1$-$C_6$ alkyl), or $C_1$-$C_{10}$ alkyl optionally substituted with 1, 2, or 3 groups independently selected from halogen, —OH, =O, —SH, —C≡N, —CF$_3$, —$C_1$-$C_3$ alkoxy, amino, mono- or dialkylamino, —N(R)C(O)R'—, —OC(=O)-amino and —OC(=O)-mono- or dialkylamino, or $C_2$-$C_6$ alkenyl or $C_2$-$C_6$ alkynyl, each of which is optionally substituted with 1, 2 or 3 groups independently selected from halogen, —OH, —SH, —C≡N, —CF$_3$, $C_1$-$C_3$ alkoxy, amino, and mono- or dialkylamino, or aryl, heteroaryl, heterocyclyl, —$C_1$-$C_6$ alkyl-aryl, —$C_1$-$C_6$ alkyl-heteroaryl, or —$C_1$-$C_6$ alkyl-heterocyclyl, where the ring portions of each are optionally substituted with 1, 2, 3, or 4 groups independently selected from halogen, —OH, —SH, —C≡N, —NR$_{105}$R'$_{105}$, —CO$_2$R, —N(R)COR', or —N(R)SO$_2$R', —C(=O)—($C_1$-$C_4$)alkyl, —SO$_2$-amino, —SO$_2$-mono or dialkylamino, —C(=O)-amino, —C(=O)-mono or dialkylamino, —SO$_2$—($C_1$-$C_4$)alkyl, or $C_1$-$C_6$ alkoxy optionally substituted with 1, 2, or 3 groups which are independently selected from halogen, or $C_3$-$C_7$ cycloalkyl optionally substituted with 1, 2, or 3 groups independently selected from halogen, —OH, —SH, —C≡N, —CF$_3$, $C_1$-$C_3$ alkoxy, amino, —$C_1$-$C_6$ alkyl and mono- or dialkylamino, or $C_1$-$C_{10}$ alkyl optionally substituted with 1, 2, or 3 groups independently selected from halogen, —OH, —SH, —C≡N, —CF$_3$, —$C_1$-$C_3$ alkoxy, amino, mono- or dialkylamino and —$C_1$-$C_3$ alkyl, or $C_2$-$C_{10}$ alkenyl or $C_2$-$C_{10}$ alkynyl each of which is optionally substituted with 1, 2, or 3 groups independently selected from halogen, —OH, —SH, —C≡N, —CF$_3$, $C_1$-$C_3$ alkoxy, amino, $C_1$-$C_6$ alkyl and mono- or dialkylamino; and the heterocyclyl group is optionally further substituted with oxo;

$R_6$, $R'_6$, $R''_6$, $R'''_6$, $R_{6a}$, $R_{6b}$, $R'_{6a}$, $R'_{6b}$, $R''_{6a}$, $R''_{6b}$, $R'''_{6a}$ and $R'''_{6b}$ independently are —OR, —NO$_2$, halogen, —CO$_2$R, —C≡N, —NRR', —SR, —SO$_2$R, —C(=O)R, —OCF$_3$, —CF$_3$, —CONRR', —SO$_2$NRR', —O—P(=O)(OR)(OR'), —N(R)(COR'), —N(R)(SO$_2$R'), —(CH$_2$)$_{0-4}$—CO—NR$_7$R'$_7$, —(CH$_2$)$_{0-4}$—O—(CH$_2$)$_{0-4}$—CONRR', —(CH$_2$)$_{0-4}$—CO—($C_1$-$C_{12}$ alkyl), —(CH$_2$)$_{0-4}$—CO—($C_2$-$C_{12}$ alkenyl), —(CH$_2$)$_{0-4}$—CO—($C_2$-$C_{12}$ alkynyl), —(CH$_2$)$_{0-4}$—CO—($C_3$-$C_7$ cycloalkyl), —(CH$_2$)$_{0-4}$—$R_{aryl}$, —(CH$_2$)$_{0-4}$—$R_{heteroaryl}$, —(CH$_2$)$_{0-4}$—$R_{heterocyclyl}$, —(CH$_2$)$_{0-4}$—CO—$R_{aryl}$, —(CH$_2$)$_{0-4}$—CO—$R_{heteroaryl}$, —(CH$_2$)$_{0-4}$—CO—$R_{heterocyclyl}$, —(CH$_2$)$_{0-4}$—CO—$R_{10}$, —(CH$_2$)$_{0-4}$—CO—O—$R_{11}$, —(CH$_2$)$_{0-4}$—SO$_2$—NR$_7$R'$_7$, —(CH$_2$)$_{0-4}$—SO—($C_1$-$C_8$ alkyl), —(CH$_2$)$_{0-4}$—SO$_2$ ($C_1$-$C_{12}$ alkyl), —(CH$_2$)$_{0-4}$—SO$_2$—($C_3$-$C_7$ cycloalkyl), —(CH$_2$)$_{0-4}$—N(H or $R_{11}$)—CO—O—$R_{11}$, —(CH$_2$)$_{0-4}$—N(H or $R_{11}$)—CO—N($R_{11}$)$_2$, —(CH$_2$)$_{0-4}$—N(H or $R_{11}$)—CS—N($R_{11}$)$_2$, —(CH$_2$)$_{0-4}$—N(—H or $R_{11}$)—CO—$R_7$, —(CH$_2$)$_{0-4}$—NR$_7$R'$_7$, —(CH$_2$)$_{0-4}$—$R_{10}$, —(CH$_2$)$_{0-4}$—O—CO—($C_1$-$C_6$ alkyl), —(CH$_2$)$_{0-4}$—O—P(O)—(O—$R_{aryl}$)$_2$, —(CH$_2$)$_{0-4}$—O—CO—N($R_{11}$)$_2$, —(CH$_2$)$_{0-4}$—O—CS—N($R_{11}$)$_2$, —(CH$_2$)$_{0-4}$—O—($R_{11}$), —(CH$_2$)$_{0-4}$—O—($R_{11}$)—COOH, —(CH$_2$)$_{0-4}$—S—($R_{11}$), $C_3$-$C_7$ cycloalkyl, —(CH$_2$)$_{0-4}$—N(—H or $R_{11}$)—SO$_2$—$R_7$, or —(CH$_2$)$_{0-4}$-$C_3$-$C_7$ cycloalkyl, or $C_1$-$C_8$ alkyl optionally substituted with one, two or three groups independently selected from $C_1$-$C_6$ alkyl, —F, —Cl, —Br, —I, —OR, —NO$_2$, —F, —Cl, —Br, —I, —CO$_2$R, —C≡N, —NRR', —SR, —SO$_2$R, —C(=O)R, —OCF$_3$, —CF$_3$, —CONRR', —SO$_2$NRR', —O—P(=O)(OR)(OR'), —N(R)(COR'), —N(R)(SO$_2$R'), —(CH$_2$)$_{0-4}$—CO—NR$_7$R'$_7$, —(CH$_2$)$_{0-4}$—CO—($C_1$-$C_{12}$ alkyl), —(CH$_2$)$_{0-4}$—CO—($C_2$-$C_{12}$ alkenyl), —(CH$_2$)$_{0-4}$—CO—($C_2$-$C_{12}$ alkynyl), —(CH$_2$)$_{0-4}$—CO—($C_3$-$C_7$ cycloalkyl), —(CH$_2$)$_{0-4}$—$R_{aryl}$, —(CH$_2$)$_{0-4}$—$R_{heteroaryl}$, —(CH$_2$)$_{0-4}$—$R_{heterocyclyl}$, —(CH$_2$)$_{0-4}$—CO—$R_{aryl}$, —(CH$_2$)$_{0-4}$—CO—$R_{heteroaryl}$, —(CH$_2$)$_{0-4}$—CO—$R_{heterocyclyl}$, —(CH$_2$)$_{0-4}$—CO—$R_{10}$, —(CH$_2$)$_{0-4}$—CO—O—$R_{11}$, —(CH$_2$)$_{0-4}$—SO$_2$—NR$_7$R'$_7$, —(CH$_2$)$_{0-4}$—SO—($C_1$-$C_8$ alkyl), —(CH$_2$)$_{0-4}$—SO$_2$ ($C_1$-$C_{12}$ alkyl), —(CH$_2$)$_{0-4}$—SO$_2$—($C_3$-$C_7$ cycloalkyl), —(CH$_2$)$_{0-4}$—N(H or $R_{11}$)—CO—O—$R_{11}$, —(CH$_2$)$_{0-4}$—N(H or $R_{11}$)—CO—N($R_{11}$)$_2$, —(CH$_2$)$_{0-4}$—N(H or $R_{11}$)—CS—N($R_{11}$)$_2$, —(CH$_2$)$_{0-4}$—N(—H or $R_{11}$)—CO—$R_7$, —(CH$_2$)$_{0-4}$—NR$_7$R'$_7$, —(CH$_2$)$_{0-4}$—$R_{10}$, —(CH$_2$)$_{0-4}$—O—CO—($C_1$-$C_6$ alkyl), —(CH$_2$)$_{0-4}$—O—P(O)—(O—$R_{aryl}$)$_2$, —(CH$_2$)$_{0-4}$—O—CO—N($R_{11}$)$_2$, —(CH$_2$)$_{0-4}$—O—CS—N($R_{11}$)$_2$, —(CH$_2$)$_{0-4}$—O—($R_{11}$), —(CH$_2$)$_{0-4}$—O—($R_{11}$)—COOH, —(CH$_2$)$_{0-4}$—S—

($R_{11}$), $C_3$-$C_7$ cycloalkyl, —$(CH_2)_{0-4}$—N(—H or $R_{11}$)—$SO_2$—$R_7$, or —$(CH_2)_{0-4}$—$C_3$-$C_7$ cycloalkyl, or $C_2$-$C_7$ alkenyl or $C_2$-$C_7$ alkynyl, each of which is optionally substituted with one, two or three groups independently selected from halogen or —OH, or $C_2$-$C_7$ alkenyl or $C_2$-$C_7$ alkynyl, each of which is optionally substituted with one, two or three groups independently selected from halogen, $C_1$-$C_3$ alkyl, —OH, —SH, —C≡N, —$CF_3$, $C_1$-$C_3$ alkoxy, amino, and mono- or dialkylamino, or —$(CH_2)_{0-4}$—O—($C_1$-$C_6$ alkyl), where the alkyl portion is optionally substituted with one, two, three, four, or five of halogen, or any two of $R_{6a}$, $R_{6b}$, $R'_{6a}$, $R'_{6b}$, $R''_{6a}$, $R''_{6b}$, $R'''_{6a}$ and $R'''_{6b}$ together are oxo;

$R_7$ and $R'_7$ are the same or different and represent —H, —$C_3$-$C_7$ cycloalkyl, —($C_1$-$C_2$ alkyl)-($C_3$-$C_7$ cycloalkyl), —($C_1$-$C_6$ alkyl)-O—($C_1$-$C_3$ alkyl), —$C_2$-$C_6$ alkenyl, —$C_2$-$C_6$ alkynyl, —$C_1$-$C_6$ alkyl chain with one double bond and one triple bond, or —$C_1$-$C_6$ alkyl optionally substituted with —OH or —$NH_2$; or;

—$C_1$-$C_6$ alkyl optionally substituted with one, two or three groups independently selected from halogen; or heterocyclyl optionally substituted with halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1C_4$ alkyl), —CO—$NH_2$, —CO—NH—$C_1$-$C_6$ alkyl, oxo and —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_1$-$C_6$ alkoxy optionally substituted with one, two or three of halogen;

aryl or heteroaryl, each of which is optionally substituted with halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH—$C_1$-$C_6$ alkyl, and —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_1$-$C_6$ alkoxy optionally substituted with one, two or three of halogen;

$R_{10}$ is heterocyclyl optionally substituted with one, two, three or four groups independently selected from $C_1$-$C_6$ alkyl;

$R_{11}$ is $C_1$-$C_6$ alkyl, $C_2$-$C_6$ alkenyl, $C_2$-$C_6$ alkynyl, $C_3$-$C_7$ cycloalkyl, —$(CH_2)_{0-2}$—$R_{aryl}$, or —$(CH_2)_{0-2}$—$R_{heteroaryl}$;

$R_{aryl}$ is aryl optionally substituted with halogen, amino, mono- or dialkylamino, —OH, —C≡N, —$SO_2$—$NH_2$, —$SO_2$—NH-$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH-$C_1$-$C_6$ alkyl, or —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_1$-$C_6$ alkoxy optionally substituted with one, two or three of halogen;

$R_{heteroaryl}$ is heteroaryl, each of which is optionally substituted with halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH—$C_1$-$C_6$ alkyl, or —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_1$-$C_6$ alkoxy optionally substituted with one, two or three of halogen;

$R_{heterocyclyl}$ is heterocyclyl optionally substituted with halogen, amino, mono- or dialkylamino, —OH, —C≡N, —$SO_2$—$NH_2$, —$SO_2$—NH—$C_1$-$C_6$ alkyl, —$SO_2$—N($C_1$-$C_6$ alkyl)$_2$, —$SO_2$—($C_1$-$C_4$ alkyl), —CO—$NH_2$, —CO—NH-$C_1$-$C_6$ alkyl, =O or —CO—N($C_1$-$C_6$ alkyl)$_2$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_2$-$C_6$ alkenyl or $C_2$-$C_6$ alkynyl, each of which is optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_1$-$C_6$ alkoxy optionally substituted with one, two or three of halogen;

$R_2$ is

—H; or —$(CH_2)_{0-4}$—$R_{aryl}$ and —$(CH_2)_{0-4}$—$R_{heteroaryl}$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $C_2$-$C_6$ alkenyl, $C_2$-$C_6$ alkynyl or —$(CH_2)_{0-4}$—$C_3$-$C_7$ cycloalkyl, each of which is optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino;

$R_3$ is —H, $C_2$-$C_6$ alkenyl, $C_2$-$C_6$ alkynyl, —$(CH_2)_{0-4}$—$R_{aryl}$, or —$(CH_2)_{0-4}$—$R_{heteroaryl}$; or $C_1$-$C_6$ alkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or —$(CH_2)_{0-4}$-$C_3$-$C_7$ cycloalkyl optionally substituted with one, two or three groups independently selected from $C_1$-$C_3$ alkyl, halogen, —OH, —SH, —C≡N, —$CF_3$, $C_1$-$C_3$ alkoxy, amino, and mono- or dialkylamino; or $R_2$ and $R_3$ taken together with the carbon atom to which they are attached form a carbocycle of three, four, five, six, or seven carbon atoms, where one atom is optionally a heteroatom selected from the group consisting of —O—, —S—, —SO$_2$—, and —NR$_8$—;

$R_c$ is hydrogen, —(CR$_{245}$R$_{250}$)$_{0-4}$-aryl, —(CR$_{245}$R$_{250}$)$_{0-4}$-heteroaryl, —(CR$_{245}$R$_{250}$)$_{0-4}$-heterocyclyl, —(CR$_{245}$R$_{250}$)$_{0-4}$-aryl-heteroaryl, —(CR$_{245}$R$_{250}$)$_{0-4}$-aryl-heterocyclyl, —(CR$_{245}$R$_{250}$)$_{0-4}$-aryl-aryl, —(CR$_{245}$R$_{250}$)$_{0-4}$-heteroaryl-aryl, —(CR$_{245}$R$_{250}$)$_{0-4}$-heteroaryl-heterocyclyl, —(CR$_{245}$R$_{250}$)$_{0-4}$-heteroaryl-heteroaryl, —(CR$_{245}$R$_{250}$)$_{0-4}$-heterocyclyl-heteroaryl, —(CR$_{245}$R$_{250}$)$_{0-4}$-heterocyclyl-heterocyclyl, —(CR$_{245}$R$_{250}$)$_{0-4}$-heterocyclyl-aryl, —[C(R$_{255}$)(R$_{260}$)]$_{1-3}$—CO—N—(R$_{255}$)$_2$, —CH(aryl)$_2$, —CH(heteroaryl)$_2$, —CH(heterocyclyl)$_2$, —CH(aryl)(heteroaryl), —(CH$_2$)$_{0-1}$—CH((CH$_2$)$_{0-6}$—OH)—(CH$_2$)$_{0-1}$-aryl, —(CH$_2$)$_{0-1}$—CH((CH$_2$)$_{0-6}$—OH—(CH$_2$)$_{0-1}$-heteroaryl, —CH(-aryl or -heteroaryl)-CO—O(C$_1$-C$_4$ alkyl), —CH(—CH$_2$—OH)—CH(OH)-phenyl-NO$_2$, (C$_1$-C$_6$ alkyl)-O—(C$_1$-C$_6$ alkyl)-OH; —CH$_2$—NH—CH$_2$—CH(—O—CH$_2$—CH$_3$)$_2$, —(CH$_2$)$_{0-6}$—C(=NR$_{235}$)(NR$_{235}$R$_{240}$), or $C_1$-$C_{10}$ alkyl optionally substituted with 1, 2, or 3 groups independently selected from the group consisting of R$_{205}$, —OC=ONR$_{235}$R$_{240}$, —S(=O)$_{0-2}$(C$_1$-C$_6$ alkyl), —SH, —NR$_{235}$C=ONR$_{235}$R$_{240}$, —C=ONR$_{235}$R$_{240}$, and —S(=O)$_2$NR$_{235}$R$_{240}$, or —(CH$_2$)$_{0-3}$—(C$_3$-C$_8$) cycloalkyl wherein the cycloalkyl is optionally substituted with 1, 2, or 3 groups independently selected from the group consisting of R$_{205}$, —CO$_2$H, and —CO$_2$—(C$_1$-C$_4$ alkyl), or cyclopentyl, cyclohexyl, or cycloheptyl ring fused to aryl, heteroaryl, or heterocyclyl wherein one, two or three carbons of the cyclopentyl, cyclohexyl, or cycloheptyl is optionally replaced with a heteroatom independently selected from NH, NR$_{215}$, O, or S(=O)$_{0-2}$, and wherein the cyclopentyl, cyclohexyl, or cycloheptyl group can be optionally substituted with one or two groups that are independently R$_{205}$, =O, —CO—NR$_{235}$R$_{240}$, or —SO$_2$—(C$_1$-C$_4$ alkyl), or $C_2$-$C_{10}$ alkenyl or $C_2$-$C_{10}$ alkynyl, each of which is optionally substituted with 1, 2, or 3 R$_{205}$ groups, wherein each aryl and heteroaryl is optionally substituted with 1, 2, or 3 R$_{200}$, and wherein each heterocyclyl is optionally substituted with 1, 2, 3, or 4 R$_{210}$;

$R_{200}$ at each occurrence is independently selected from —OH, —NO$_2$, halogen, —CO$_2$H, C≡N, —(CH$_2$)$_{0-4}$—CO—NR$_{220}$R$_{225}$, —(CH$_2$)$_{0-4}$—CO—(C$_1$-C$_{12}$ alkyl), —(CH$_2$)$_{0-4}$—CO—(C$_2$-C$_{12}$ alkenyl), —(CH$_2$)$_{0-4}$—CO—(C$_2$-C$_{12}$ alkynyl), —(CH$_2$)$_{0-4}$—CO—(C$_3$-C$_7$ cycloalkyl), —(CH$_2$)$_{0-4}$—CO-aryl, —(CH$_2$)$_{0-4}$—CO-heteroaryl, —(CH$_2$)$_{0-4}$—CO-heterocyclyl, —(CH$_2$)$_{0-4}$—CO—O—R$_{215}$, —(CH$_2$)$_{0-4}$—SO$_2$—NR$_{220}$R$_{225}$, —(CH$_2$)$_{0-4}$—SO—(C$_1$-C$_8$ alkyl), —(CH$_2$)$_{0-4}$—SO$_2$—(C$_1$-C$_{12}$ alkyl), —(CH$_2$)$_{0-4}$—SO$_2$—(C$_3$-C$_7$ cycloalkyl), —(CH$_2$)$_{0-4}$—N(H or R$_{215}$)—CO—O—R$_{215}$, —(CH$_2$)$_{0-4}$—N(H or R$_{215}$)—CO—N(R$_{215}$)$_2$, —(CH$_2$)$_{0-4}$—N—CS—N(R$_{215}$)$_2$, —(CH$_2$)$_{0-4}$—N(—H or R$_{215}$)—CO—R$_{220}$, —(CH$_2$)$_{0-4}$—NR$_{220}$R$_{225}$, —(CH$_2$)$_{0-4}$—O—CO—(C$_1$-C$_6$ alkyl), —(CH$_2$)$_{0-4}$—O—P(O)—(OR$_{240}$)$_2$, —(CH$_2$)$_{0-4}$—O—CO—N(R$_{215}$)$_2$, —(CH$_2$)$_{0-4}$—O—CS—N(R$_{215}$)$_2$, —(CH$_2$)$_{0-4}$—O—(R$_{215}$), —(CH$_2$)$_{0-4}$—O—(R$_{215}$)—COOH, —(CH$_2$)$_{0-4}$—S—(R$_{215}$), —(CH$_2$)$_{0-4}$—O—(C$_1$-C$_6$ alkyl optionally substituted with 1, 2, 3, or 5-F), C$_3$-C$_7$ cycloalkyl, —(CH$_2$)$_{0-4}$—N(H or R$_{215}$)—SO$_2$—R$_{220}$, —(CH$_2$)$_{0-4}$—C$_3$-C$_7$ cycloalkyl, or $C_1$-$C_{10}$ alkyl optionally substituted with 1, 2, or 3 R$_{205}$ groups, or $C_2$-$C_{10}$ alkenyl or $C_2$-$C_{10}$ alkynyl, each of which is optionally substituted with 1 or 2 R$_{205}$ groups, wherein the aryl and heteroaryl groups at each occurrence are optionally substituted with 1, 2, or 3 groups that are independently R$_{205}$, R$_{210}$, or $C_1$-$C_6$ alkyl substituted with 1, 2, or 3 groups that are independently R$_{205}$ or R$_{210}$, and wherein the heterocyclyl group at each occurrence is optionally substituted with 1, 2, or 3 groups that are independently R$_{210}$;

$R_{205}$ at each occurrence is independently selected from C$_1$-C$_6$ alkyl, halogen, —OH, —O-phenyl, —SH, —C≡N, —CF$_3$, C$_1$-C$_6$ alkoxy, NH$_2$, NH(C$_1$-C$_6$ alkyl) or N—(C$_1$-C$_6$ alkyl)(C$_1$-C$_6$ alkyl);

$R_{210}$ at each occurrence is independently selected from halogen, C$_1$-C$_6$ alkoxy, C$_1$-C$_6$ haloalkoxy, —NR$_{220}$R$_{225}$, OH, C≡N, —CO—(C$_1$-C$_4$ alkyl), —SO$_2$—NR$_{235}$R$_{240}$, —CO—NR$_{235}$R$_{240}$, —SO$_2$—(C$_1$-C$_4$ alkyl), =O, or C$_1$-C$_6$ alkyl, C$_2$-C$_6$ alkenyl, C$_2$-C$_6$ alkynyl or C$_3$-C$_7$ cycloalkyl, each of which is optionally substituted with 1, 2, or 3 R$_{205}$ groups;

$R_{215}$ at each occurrence is independently selected from C$_1$-C$_6$ alkyl, —(CH$_2$)$_{0-2}$-(aryl), C$_2$-C$_6$ alkenyl, C$_2$-C$_6$ alkynyl, C$_3$-C$_7$ cycloalkyl, and —(CH$_2$)$_{0-2}$-(heteroaryl), —(CH$_2$)$_{0-2}$-(heterocyclyl), wherein the aryl group at each occurrence is optionally substituted with 1, 2, or 3 groups that are independently R$_{205}$ or R$_{210}$, and wherein the heterocyclyl and heteroaryl groups at each occurrence are optionally substituted with 1, 2, or 3 R$_{210}$;

$R_{220}$ and $R_{225}$ at each occurrence are independently selected from —H, —C$_3$-C$_7$ cycloalkyl, —(C$_1$-C$_2$ alkyl)-(C$_3$-C$_7$ cycloalkyl), —(C$_1$-C$_6$ alkyl)-O—(C$_1$-C$_3$ alkyl), —C$_2$-C$_6$ alkenyl, —C$_2$-C$_6$ alkynyl, —C$_1$-C$_6$ alkyl chain with one double bond and one triple bond, -aryl, -heteroaryl, and -heterocyclyl, or —C$_1$-C$_{10}$ alkyl optionally substituted with —OH, —NH$_2$ or halogen, wherein the aryl, heterocyclyl and heteroaryl groups at each occurrence are optionally substituted with 1, 2, or 3 R$_{270}$ groups $R_{235}$ and $R_{240}$ at each occurrence are independently H, or C$_1$-C$_6$ alkyl;

$R_{245}$ and $R_{250}$ at each occurrence are independently selected from —H, C$_1$-C$_4$ alkyl, C$_1$-C$_4$ alkylaryl, C$_1$-C$_4$ alkylheteroaryl, C$_1$-C$_4$ hydroxyalkyl, C$_1$-C$_4$ alkoxy, C$_1$-C$_4$ haloalkoxy, —(CH$_2$)$_{0-4}$—C$_3$-C$_7$ cycloalkyl, C$_2$-C$_6$ alkenyl, C$_2$-C$_6$ alkynyl, and phenyl; or $R_{245}$ and $R_{250}$ are taken together with the carbon to which they are attached to form a carbocycle of 3, 4, 5, 6, or 7 carbon atoms, where one carbon atom is optionally replaced by a heteroatom selected from —O—, —S—, —SO$_2$—, and —NR$_{220}$—;

$R_{255}$ and $R_{260}$ at each occurrence are independently selected from —H, —(CH$_2$)$_{1-2}$—S(O)$_{0-2}$—(C$_1$-C$_6$ alkyl)-(C$_1$-C$_4$ alkyl)-aryl, —(C$_1$-C$_4$ alkyl)-heteroaryl, —(C$_1$-C$_4$ alkyl)-heterocyclyl, -aryl, -heteroaryl, -heterocyclyl, —(CH$_2$)$_{1-4}$—R$_{265}$—(CH$_2$)$_{0-4}$-aryl, —(CH$_2$)$_{1-4}$—R$_{265}$—(CH$_2$)$_{0-4}$-heteroaryl, —(CH$_2$)$_{1-4}$—R$_{265}$—(CH$_2$)$_{0-4}$-heterocyclyl, or C$_1$-C$_6$ alkyl, C$_2$-C$_6$ alkenyl, C$_2$-C$_6$ alkynyl or —(CH$_2$)$_{0-4}$—C$_3$-C$_7$ cycloalkyl, each of which is optionally substituted with 1, 2, or 3 R$_{205}$ groups, wherein each aryl or phenyl is optionally substituted with 1, 2, or 3 groups that are independently R$_{205}$, R$_{210}$, or $C_1$-$C_6$ alkyl substituted with 1, 2, or 3 groups that are independently $R_{205}$ or $R_{210}$, and wherein each heterocyclyl is optionally substituted with 1, 2, 3, or 4 $R_{210}$;

$R_{265}$ at each occurrence is independently —O—, —S— or —N($C_1$-$C_6$ alkyl)-;

$R_{270}$ at each occurrence is independently $R_{205}$, halogen $C_1$-$C_6$ alkoxy, $C_1$-$C_6$ haloalkoxy, $NR_{235}R_{240}$, —OH, —C≡N, —CO—($C_1$-$C_4$ alkyl), $SO_2$—$NR_{235}R_{240}$, —CO—$NR_{235}R_{240}$, —$SO_2$—($C_1$-$C_4$ alkyl), =O, or $C_1$-$C_6$ alkyl, $C_2$-$C_6$ alkenyl, $C_2$-$C_6$ alkynyl or —$(CH_2)_{0-4}$—$C_3$-$C_7$ cycloalkyl, each of which is optionally substituted with 1, 2, or 3 $R_{205}$ groups;

and pharmaceutically acceptable salts thereof.

The invention also provides intermediates and methods useful for preparing the compounds of formula X.

The invention further provides pharmaceutical compositions comprising a compound of formula X.

The present invention also provides the use of a compound of formula (X) and pharmaceutically acceptable salts thereof for the manufacture of a medicament. The present invention also provides a method of treating a patient who has Alzheimer's Disease or other diseases that can be treated by inhibiting beta-secretase activity.

DETAILED DESCRIPTION OF THE INVENTION

The compounds encompassed by the instant invention are those described by the general formula (I) set forth above, and the pharmaceutically acceptable salts and prodrugs thereof.

In an embodiment, the compounds of formula (I) have syn stereochemistry.

In an embodiment, the compounds of formula (I) have anti stereochemistry.

The invention also provides intermediates and methods useful for preparing the compounds of formula I.

In an embodiment, the compound has formula (Ia):

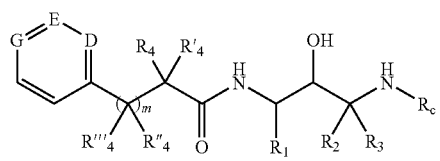

(Ia)

where m, $R_1$, $R_2$, $R_3$, $R_4$, $R'_4$, $R''_4$, $R'''_4$ and $R_c$ are as defined above for (I) and D, E and G independently represent N, $N^+$—$O^-$ or $CR_6$ where $R_6$ is as defined above for (I), provided that not more than two of D, E and G are N and not more than one of D, E and G is $N^+$—$O^-$. The aromatic ring containing D, E and G can also be optionally substituted with up to four groups selected from $R_6$, $R'_6$, $R''_6$ and $R'''_6$, as defined above for (I). Preferred compounds for formula (Ia) are those where D, E and G are $CR_6$; $R_2$ and $R_3$ are hydrogen; $R_1$ is —$C_1$-$C_3$ alkyl-aryl, the aryl optionally substituted with one or two groups independently selected from halogen; and $R_C$ is —$C_1$-$C_3$ alkyl-aryl, the aryl optionally substituted with halogen or —$C_1$-$C_6$ alkyl. More preferred compounds of formula (Ia) are those where m is 0; $R_4$ and $R'_4$ are hydrogen; $R_1$ is phenylmethyl, where the phenyl is optionally substituted with one or two groups independently selected from halogen; $R_2$ and $R_3$ are hydrogen; and $R_c$ is phenylmethyl, where the phenyl is optionally substituted with halogen or —$C_1$-$C_6$ alkyl.

In another embodiment, the compound has a formula of (Ib):

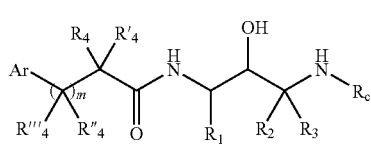

(Ib)

where m, $R_1$, $R_2$, $R_3$, $R_4$, $R'_4$, $R''_4$, $R'''_4$ and $R_c$ are as defined above for (I) and Ar is an aromatic ringed system other than the aromatic ring containing D, E and G of formula (Ia) above, and is optionally substituted with one, two, three or four groups independently selected from $R_6$, $R'_6$, $R''_6$ and $R'''_6$, as defined above for (I); where Ar is selected from 1,1-dioxido-3-oxo-1,2-benzisothiazol-2(3H)-yl, 1,3-dioxo-1,3-dihydro-2H-isoindol-2-yl, 1,2,3,4-tetrahydronaphthalen-1-yl, 2,3-dihydro-1H-inden-1-yl, 2,3-dihydro-1-benzofuran-5-yl, benzofuran-4-yl, 2,3-dihydro-1H-inden-5-yl, 6-oxopyridazin-1(6H)-yl, 1-naphthyl, 2-naphthyl, 3,4-dihydronaphthalen-1-yl, 1H-indol-1-yl, 2,3-dihydro-1-benzofuran-4-yl, 1H-pyrazol-1-yl, 2-oxo-1,3-benzoxazol-3(2H)-yl, 1H-benzimidazol-2-yl, 2-thioxo-1,3-benzothiazol-3(2H)-yl, 1,2,4-oxadiazol-5-yl, 1H-benzimidazol-1-yl, [1,2,4]triazolo[4,3-a]pyrimidin-3-yl, 2H-tetraazol-2-yl, 1,3-benzothiazol-2-yl, 2-oxo-2,3-dihydro-1H-benzimidazol-1-yl, 2,3-dihydro-1H-indol-1-yl, 1H-tetraazol-1-yl, 1H-1,2,3-benzotriazol-1-yl, 1,3benzodioxol-5-yl, thien-2-yl, thien-3-yl, 2,6-dioxo-1,2,3,6-tetrahydro-7H-purin-7-yl, 1H-indol-3-yl, benzothien-4-yl, 2,6-dioxo-1,2,3,6-tetrahydro-9H-purin-9-yl, 2-oxo-1,3-benzothiazol-3(2H)-yl, 1,3-thiazol-5-yl, 1,3-benzoxazol-5-yl, 2H-1,2,3-benzotriazol-2-yl, 1,3-thiazol-4-yl, 1H-1,2,4-triazol-1-yl, 1H-imidazol-1-yl, 2-furyl, 4H-[1,2,4]triazolo[1,5-a]benzimidazol-4-yl, 1H-indol-2-yl, 3,4-dihydro-2H-1,5-benzodioxepin-7-yl, 2-oxo-pyridin-1(2H)-yl, 1-benzofuran-2-yl, dibenzo[b,d]furan-2-yl, 6-oxo-pyridazin-1(6H)-yl, 3,4-dihydro-2H-chromen-6-yl, 3-oxo-2,3-dihydro-1H-isoindol-1-yl, 1H-pyrrol-1-yl, 1-oxo-1,3-dihydro-2H-isoindol-2-yl, 2-thioxo-2,3-dihydro-1,3-thiazol-4-yl, isoxazol-5-yl, 2,3-dihydro-1,4-benzodioxin-6-yl, 2-oxo-2H-1,3-benzoxazin-3(4H)-yl, 2-oxo-2,3-dihydro-1,3-benzoxazol-5-yl, 2-oxo-2,3-dihydro-1H-benzimidazol-5-yl, 1H-pyrrol-2-yl, [1,2,4]triazolo[1,5-a]pyrimidin-2-yl, 4H-1,2,4-triazol-3-yl, 2,4-dioxo-1,2,3,4-tetrahydropyridin-3-yl and 3-oxo-2,1-benzisothiazol-1(3H)-yl. Preferred compounds of formula (Ib) are those where $R_2$ and $R_3$ are hydrogen; $R_1$ is —$C_1$-$C_3$ alkyl-aryl, the aryl optionally substituted with one or two groups independently selected from halogen; and $R_c$ is hydroxy $C_1$-$C_6$ alkyl, —$C_1$-$C_3$ alkyl-aryl, the aryl optionally substituted with halogen or —$C_1$-$C_6$ alkyl. More preferred compounds of formula (Ib) are those where m is 0; $R_4$ and $R'_4$ are hydrogen; $R_1$ is phenylmethyl, where the phenyl is optionally substituted with one or two groups independently selected from halogen; $R_2$ and $R_3$ are hydrogen; and $R_c$ is phenylmethyl, where the phenyl is optionally substituted with halogen or —$C_1$-$C_6$ alkyl.

In an embodiment, the compound has formula (Ic):

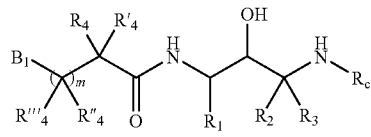

(Ic)

where m, $R_1$, $R_2$, $R_3$, $R_4$, $R'_4$, $R''_4$, $R'''_4$ and $R_c$ are as defined above for (I) and $B_1$ is selected from piperazin-1-yl, piperi dine-4-yl, morpholin-4-yl, 4,5,6,7,3a,7a-hexahydroisoindol-2-yl, 3-azabicyclo[3.2.2]nonan-3-yl, 1,4-diazaperhydroepin-1-yl, 1,4-thiazaperhydroin-1-yl, thiolan-3-yl, thiolan-2-yl and imidazolidin-1-yl, each of which is optionally substituted with up to eight groups selected from $R_6$, $R_{6a}$, $R'_6$, $R'_{6a}$, $R''_6$, $R''_{6a}$, $R'''_6$ and $R'''_{6a}$. Preferred compounds of formula (Ic) are those where $B_1$ is piperazin-1-yl or piperidine-4-yl, each of which is optionally substituted with one, two or three groups selected from oxo and $C_1$-$C_6$ alkyl; $R_2$ and $R_3$ are hydrogen; $R_1$ is —$C_1$-$C_3$ alkyl-aryl, the aryl optionally substituted with one or two groups independently selected from halogen; and $R_c$ is —$C_1$-$C_3$ alkyl-aryl, the aryl optionally substituted with halogen or —$C_1$-$C_6$ alkyl. More preferred compounds of formula (Ic) are those where m is 0; $R_4$ and $R'_4$ are hydrogen; $B_1$ is piperazin-1-yl or piperidine-4-yl, each of which is optionally substituted with one, two or three groups selected from oxo and $C_1$-$C_6$ alkyl; $R_1$ is phenylmethyl, where the phenyl is optionally substituted with one or two groups independently selected from halogen; $R_2$ and $R_3$ are hydrogen; and $R_c$ is phenylmethyl, where the phenyl is optionally substituted with halogen or —$C_1$-$C_6$ alkyl.

In another embodiment, the compound has a formula of (Id):

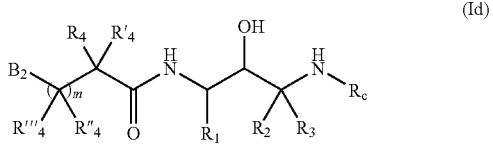

(Id)

where m, $R_1$, $R_2$, $R_3$, $R_4$, $R'_4$, $R''_4$, $R'''_4$ and $R_c$ are as defined above for (I) and $B_2$ is cycloalkyl optionally substituted with up to eight groups selected from $R_6$, $R_{6a}$, $R'_6$, $R'_{6a}$, $R''_6$, $R''_{6a}$, $R'''_6$ and $R'''_{6a}$. Preferred compounds of formula (Id) are those where $B_2$ is cyclohexyl optionally substituted with one, two or three groups selected from oxo and $C_1$-$C_6$ alkyl; $R_2$ and $R_3$ are hydrogen; $R_1$ is —$C_1$-$C_3$ alkyl-aryl, the aryl optionally substituted with one or two groups independently selected from halogen; and $R_C$ is —$C_1$-$C_3$ alkyl-aryl, the aryl optionally substituted with halogen or —$C_1$-$C_6$ alkyl. More preferred compounds of formula (Id) are those where m is 0; $R_4$ and $R'_4$ are hydrogen; $B_2$ is cyclohexyl optionally substituted with oxo and $C_1$-$C_6$ alkyl; $R_1$ is phenylmethyl, where the phenyl is optionally substituted with one or two groups independently selected from halogen; $R_2$ and $R_3$ are hydrogen; and $R_c$ is phenylmethyl, where the phenyl is optionally substituted with halogen or —$C_1$-$C_6$ alkyl.

The present invention also includes a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating Frontotemporal dementias with Parkinsonism (FTDP), for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound of formula (I) and pharmaceutically acceptable salts thereof.

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is FTDP.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease.

In an embodiment, this method of treatment can prevent a disease from developing.

In an embodiment, this method of treatment can employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The present invention also includes a pharmaceutical composition which includes a substituted amine of formula (I) and pharmaceutically acceptable salts thereof.

The present invention also includes the use of a substituted amine of formula (I) and pharmaceutically acceptable salts thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a substituted amine of formula (I) can be employed where the disease is Alzheimer's disease.

In an embodiment, this use of a substituted amine of formula (I) can help prevent or delay the onset of Alzheimer's disease.

In an embodiment, this use of a substituted amine of formula (I) can be employed where the disease is mild cognitive impairment.

In an embodiment, this use of a substituted amine of formula (I) can be employed where the disease is Down's syndrome.

In an embodiment, this use of a substituted amine of formula (I) can be employed where the disease is Hereditary Cerebral Hemorrhage with Amyloidosis of the Dutch-Type.

In an embodiment, this use of a substituted amine of formula (I) can be employed where the disease is cerebral amyloid angiopathy.

In an embodiment, this use of a substituted amine of formula (I) can be employed where the disease is degenerative dementias.

In an embodiment, this use of a substituted amine of formula (I) can be employed where the disease is diffuse Lewy body type of Alzheimer's disease.

In an embodiment, this use of a substituted amine employs a pharmaceutically acceptable salt selected from the group consisting of salts of the following acids hydrochloric, hydrobromic, hydroiodic, nitric, sulfuric, phosphoric, citric, TFA, methanesulfonic, $CH_3$—$(CH_2)$—COOH where n is 0 thru 4, HOOC—$(CH_2)_n$—COOH where n is as defined above, HOOC—CH=CH—COOH, and phenyl-COOH.

The present invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain which include administration of a therapeutically effective amount of a substituted amine of formula (I) and pharmaceutically acceptable salts thereof.

The present invention also includes a method for inhibiting beta-secretase activity, including exposing said beta-secretase to an effective inhibitory amount of a compound of the formula (I) or a pharmaceutically acceptable salt thereof.

Preferably, this method employs a compound that inhibits 50% of the enzyme's activity at a concentration of less than 50 micromolar.

This method more preferably employs a compound that inhibits 50% of the enzyme's activity at a concentration of 10 micromolar or less This method even more preferably employs a compound that inhibits 50% of the enzyme's activity at a concentration of 1 micromolar or less.

In a particular embodiment, this method employs a compound that inhibits 50% of the enzyme's activity at a concentration of 10 nanomolar or less.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The present invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of a compound of formula (I) or a pharmaceutically acceptable salt thereof.

In an embodiment, this method employs a cleavage site: between Met652 and Asp653, numbered for the APP-751 isotype; between Met 671 and Asp 672, numbered for the APP-770 isotype; between Leu596 and Asp597 of the APP-695 Swedish Mutation; between Leu652 and Asp653 of the APP-751 Swedish Mutation; or between Leu671 and Asp672 of the APP-770 Swedish Mutation.

In an embodiment, this method exposes said reaction mixture in vitro.

In an embodiment, this method exposes said reaction mixture in a cell.

In an embodiment, this method exposes said reaction mixture in an animal cell.

In an embodiment, this method exposes said reaction mixture in a human cell.

The present invention also includes a method for inhibiting production of amyloid beta peptide (A beta) in a cell, including administering to said cell an effective inhibitory amount of a compound of formula (I) or a pharmaceutically acceptable salt thereof.

In an embodiment, this method includes administering to an animal.

In an embodiment, this method includes administering to a human.

The present invention also includes a method for inhibiting the production of beta-amyloid plaque in an animal, including administering to said animal an effective inhibitory amount of a compound of the formula (I) or a pharmaceutically acceptable salt thereof.

In an embodiment, this method includes administering to a human.

The present invention also includes a method for treating or preventing a disease characterized by beta-amyloid deposits in the brain including administering to a patient an effective therapeutic amount of a hydroxyethylene compound of the formula (I) or a pharmaceutically acceptable salt thereof.

Preferably, this method employs a compound that inhibits 50% of the enzyme's activity at a concentration of less than 50 micromolar.

This method more preferably employs a compound that inhibits 50% of the enzyme's activity at a concentration of 10 micromolar or less This method even more preferably employs a compound that inhibits 50% of the enzyme's activity at a concentration of 1 micromolar or less.

In a particular embodiment, this method employs a compound that inhibits 50% of the enzyme's activity at a concentration of 10 nanomolar or less.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The present invention also includes a composition including beta-secretase complexed with a compound of formula (I) or a pharmaceutically acceptable salt thereof.

The present invention also includes a method for producing a beta-secretase complex including exposing beta-secretase to a compound of formula (I) or a pharmaceutically acceptable salt thereof, in a reaction mixture under conditions suitable for the production of said complex.

In an embodiment, this method employs exposing in vitro.

In an embodiment, this method employs a reaction mixture that is a cell.

The present invention also includes a component kit including component parts capable of being assembled, in which at least one component part includes a compound of formula Xa enclosed in a container.

In an embodiment, this component kit includes lyophilized compound, and at least one further component part includes a diluent.

The present invention also includes a container kit including a plurality of containers, each container including one or more unit dose of a compound of formula (I) or a pharmaceutically acceptable salt thereof.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The present invention also includes an agent kit including a compound of formula (I) or a pharmaceutically acceptable salt thereof; and one or more therapeutic agent selected from the group consisting of an antioxidant, an anti-inflammatory, a gamma secretase inhibitor, a neurotrophic agent, an acetyl cholinesterase inhibitor, a statin, an A beta peptide, and an anti-A beta antibody.

The present invention also includes a composition including a compound of formula (I) or a pharmaceutically acceptable salt thereof; and an inert diluent or edible carrier.

In an embodiment, this composition includes a carrier that is an oil.

The present invention also includes a composition including a compound of formula (I) or a pharmaceutically acceptable salt thereof; and a binder, excipient, disintegrating agent, lubricant, or gildant.

The present invention also includes a composition including a compound of formula (I) or a pharmaceutically acceptable salt thereof; disposed in a cream, ointment, or patch.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

By "Protecting Group" in the present invention is meant any suitable organic protecting group such as disclosed in T. W. Green and P. G. M. Wuts in "Protective Groups in Organic Chemistry", John Wiley and Sons, 1991. Preferred protecting groups in the present invention are t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyoopentanyloxycarbonyl, cyclohexanyloxycarbonyl, 1-methylcyclohexanyloxycabonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobrornyloxycarbonyl, 1-piperidyloxycarbonyl, 9-fluoroenylmethyl carbonate, —CH—CH=CH$_2$, or phenyl-C(=N—)—H.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system, and can optionally contain a double bond. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl or di($C_1$-$C_6$)alkylamino($C_1$-$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, —COOH, —C(=O)O($C_1$-$C_6$ alkyl), —C(=O)NH$_2$, —C(=O)N(mono- or di-$C_1$-$C_6$ alkyl), —S($C_1$-$C_6$ alkyl), —SO$_2$ ($C_1$-$C_6$ alkyl), —O—C(=O)($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$—($C_1$-$C_6$ alkyl), —NH—C(=O)NH$_2$, —NH—C(=O)N(mono- or di-$C_1$-$C_6$ alkyl), —NH($C_1$-$C_6$ alkyl)-C(=O)—NH$_2$ or —NH($C_1$-$C_6$ alkyl)-C(=O)—N-(mono- or di-$C_1$-$C_6$ alkyl).

By "heteroaryl" is meant one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazothiazolyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl, —COOH, —C(=O)O($C_1$-$C_6$ alkyl), —C(=O)NH$_2$, —C(=O)N(mono- or di-$C_1$-$C_6$ alkyl), —S($C_1$-$C_6$ alkyl), —SO$_2$ ($C_1$-$C_6$ alkyl), —O—C(=O)($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$—($C_1$-$C_6$ alkyl), —NH—C(=O)NH$_2$, —NH—C(=O)N(mono- or di-$C_1$-$C_6$ alkyl), —NH($C_1$-$C_6$ alkyl)-C(=O)—NH$_2$ or —NH($C_1$-$C_6$ alkyl)-C(=O)—N-(mono- or di-$C_1$-$C_6$ alkyl).

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. The heterocycle may optionally contain a double bond. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$) alkyl or =O.

Synthesis

The present invention is the substituted amines (I), which are useful in treating and preventing Alzheimer's disease. The anti-Alzheimer's substituted amines (I) are made by methods well known to those skilled in the art from starting compounds known to those skilled in the art. The process chemistry is well known to those skilled in the art. The most general process to prepare the compounds of formulas (I), (Ia) and (Ib) of the present invention is set forth in CHART A below, where m, B, $R_1$, $R_2$, $R_3$, $R_4$, $R'_4$, $R''_4$, $R'''_4$, $R_6$, $R'_6$, $R''_6$, $R'''_6$ and $R_c$ are as defined above for (I). $X_2$ and $X_3$ are functional organic groups defined in more detail below.

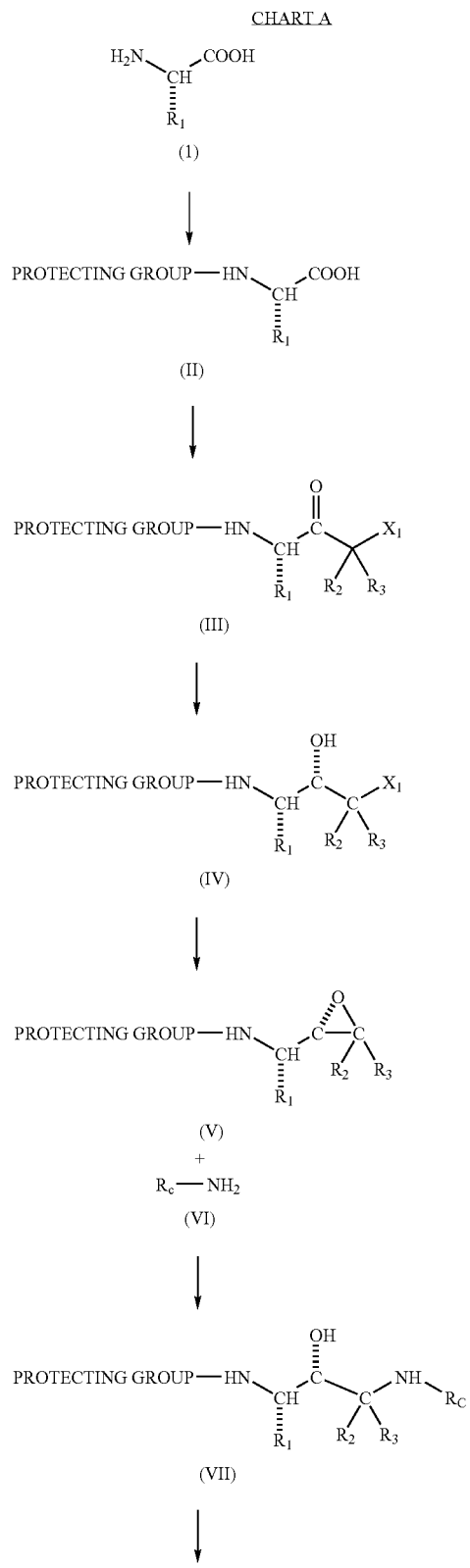

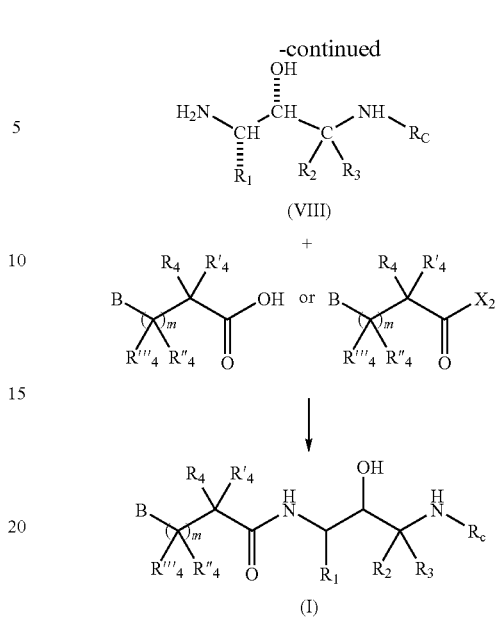

The chemistry is straight forward and in summary involves the steps of N-protecting an amino acid (1) starting material to produce the corresponding protected amino acid (II), reaction of the protected amino acid (II) with diazomethane followed by work-up to add a carbon atom to produce the corresponding protected compound (III), reduction of the protected compound (III) to the corresponding alcohol (IV), formation of the corresponding epoxide (V), opening of the epoxide (V) with a C-terminal amine, $R_c$—$NH_2$ (VI) to produce the corresponding protected alcohol (VII) which then has the nitrogen protecting group removed to produce the corresponding amine (VIII), which is then reacted with an amide forming agent of the formula (IX) to produce the anti-Alzheimer compounds of formula (I). One skilled in the art will appreciate that these are all well known reactions in organic chemistry. A chemist skilled in the art, knowing the chemical structure of the biologically active compounds of formula (I) of the invention would be able to prepare them by known methods from known starting materials without any additional information. The explanation below therefore is not necessary but is deemed helpful to those skilled in the art who desire to make the compounds of the present invention.

The backbone of the compounds of the present invention is a hydroxyethylamine moiety, —NH—CH(R)—CH(OH)—. It can be readily prepared by methods disclosed in the literature and known to those skilled in the art. For example, J. Med. Chem., 36, 288-291 (1992), Tetrahedron Letters, 28, 5569-5572 (1987), J. Med. Chem., 38, 581-584 (1994) and Tetrahedron Letters, 38, 619-620 (1997) all disclose processes to prepare hydroxyethylamine type compounds.

CHART A sets forth a general method used in the present invention to prepare the compounds of formula (I). The anti-Alzheimer compounds of formula (I) can be prepared by starting with the corresponding amino acid (1). The amino acids (1) are well known to those skilled in the art or can be readily prepared from known compounds by methods well known to those skilled in the art. The compounds of formula (I) have at least two enantiomeric centers which give four enantiomers. The first of these enantiomeric centers derives from the amino acid starting material (1). It is preferred to commercially obtain or produce the desired enantiomer (S) rather than produce an enantiomerically impure mixture and then have to separate out the desired enantiomer (S). It is preferred to start the process with enantiomerically pure (S)-amino acid (1) of the same configuration as that of the compounds of formula (I). For the amino acids (1), $R_1$ is as defined above for formula (I).

It is preferred that $R_1$ be —$(CH_2)_{0-1}$-aryl or —$(CH_2)_{0-1}$-heteroaryl. It is more preferred that $R_1$ is —$(CH_2)$-aryl or —$(CH_2)_{0-1}$-heteroaryl. It is further preferred that aryl is phenyl; it is even more preferred that the phenyl is substituted with two —F. It is additionally preferred that the —F substitution is 3,5-difluorobenzyl.

When $R_1$ is heteroaryl or heterocyclyl, the bond from the heteroaryl or heterocyclyl group to the —$(CH_2)$— group can be from any ring atom which has an available valence provided that such bond does not result in formation of a charged species or unstable valence. This means that the heteroaryl or heterocyclyl group is bonded to —$(CH_2)$— by any ring atom of the parent heteroaryl or heterocyclyl group which is substituted by hydrogen such that the new bond to the heteroaryl or heterocyclyl group replaces the hydrogen atom and its bond.

The first step of the process is to protect the free amino group of the (S)-amino acid (1) with an amino protecting group to produce the (S)-protected amino acid (II) by methods well known to those skilled in the art. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—$NH_2$) during subsequent reactions on the (S)-amino acid (1) which would not proceed well, either because the amino group would react and be functionalized in a way that is inconsistent with its need to be free for subsequent reactions, or the free amino group would interfere in the reaction. When the amino protecting group is no longer needed, it is removed by methods well known to those skilled in the art. By definition the amino protecting group must be readily removable as is known to those skilled in the art by methods well known to those skilled in the art.

The (S)-protected amino acid (II) is transformed to the corresponding (S)-protected compound (III) by two different methods depending on the nature of $R_2$ and $R_3$. $R_2$ and $R_3$ are as defined above for formula (I).

It is preferred that $R_2$ and $R_3$ both be —H. If $R_2$ and $R_3$ are not the same, an additional enantiomeric center is added to the molecule. If it is desired that both $R_2$ and $R_3$ are —H, then the (S)-protected amino acid (II) is reacted with diazomethane, as is well known to those skilled in the art, followed by reaction with a compound of the formula H—$X_1$ to produce the (S)-protected compound (III). $X_1$ includes —Cl, —Br, —I, —O-tosylate, —O-mesylate, —O-nosylate.; it is preferred that —$X_1$ be —Br or —Cl. Suitable reaction conditions include running the reaction in inert solvents, such as but not limited to ether, tetrahydrofuran and the like. The reactions from the (S)-protected amino acid (II) to the (S)-protected compound (III) are carried out for a period of time between 10 minutes and 1 day and at temperatures ranging from −78 degrees to 20-25 degrees C. It is preferred to conduct the reactions for a period of time between 1-4 hours and at temperatures between −30 degrees to −10 degrees C. This process adds one methylene group.

Alternatively, the (S)-protected compounds of formula (III) can be prepared by first converting the (S)-protected amino acid (II) to a corresponding methyl or ethyl ester, according to methods well established in the art, followed by treatment with a reagent of formula $X_1$—$C(R_2)(R_3)$—$X_1$ and a strong metal base. The base serves to affect a halogen-metal exchange, where the —$X_1$ undergoing exchange is a halogen selected from chlorine, bromine or iodine. The nucleophilic addition to the ester derivative gives directly the (S)-protected compound (III). Suitable bases include, but are not limited to the alkyllithiums including, for example, sec-butyllithium, n-butyllithium, and t-butyllithium. The reactions are preferably conducted at low temperature, such as −78 degrees C. Suitable reaction conditions include running the reaction in inert solvents, such as but not limited to, ether, tetrahydrofuran, and the like. Where $R_2$ and $R_3$ are both hydrogen, then examples of $X_1$—$C(R_2)(R_3)$—$X_1$ include dibromomethane, diiodomethane, chloroiodo-methane, bromoiodomethane, and bromochloromethane. One skilled in the art knows suitable and preferred conditions for to conducting this reaction. Furthermore, if $R_2$ and/or $R_3$ are not —H, then by the addition of —$C(R_2)(R_3)$—$X_1$ to esters of the (S)-protected amino acid (II) to produce the (S)-protected compound (III), an additional chiral center will be incorporated into the product, provided that $R_2$ and $R_3$ are not the same.

The (S)-protected compound (III) is then reduced by methods well known to those skilled in the art for reduction of a ketone to the corresponding secondary alcohol affording the corresponding alcohol (IV). The methods and reaction conditions for reducing the (S)-protected compound (III) to the corresponding alcohol (IV) include, for example, sodium borohydride, lithium borohydride, borane, diisobutylaluminum hydride, and lithium aluminium hydride. Sodium borohydride is the preferred reducing agent. The reductions are carried out for a period of time between 1 hour and 3 days at temperatures ranging from −78 degrees C. to elevated temperature up to the reflux point of the solvent employed. It is preferred to conduct the reduction between −78 degrees C. and 0 degrees C. If borane is used, it may be employed as a complex, for example, borane-methyl sulfide complex, borane-piperidine complex, or borane-tetrahydrofuran complex. Suitable and preferred combinations of reducing agents and reaction conditions are known to those skilled in the art; see for example, Larock, R. C. in Comprehensive Organic Transformations, VCH Publishers, 1989. The reduction of the (S)-protected compound (III) to the corresponding alcohol (IV) produces the second chiral center (third chiral center if $R_2$ and $R_3$ are not the same). The reduction of the (S)-protected compound (III) produces a mixture of enantiomers at the second center, (S, R/S)-alcohol (IV). This enantiomeric mixture is then separated by methods known to those skilled in the art such as selective low-temperature recrystallization or chromatographic separation, for example by HPLC, employing commercially available chiral columns. The enantiomer that is used in the remainder of the process of CHART A is the (S,S)-alcohol (IV) since this enantiomer will give the desired biologically active anti-Alzheimer (S,R)-compounds of formula (I).

The (S,S)-alcohol (IV) is transformed to the corresponding epoxide (V) by methods known to those skilled in the art. The stereochemistry of the (S)-(IV) center is maintained in forming the epoxide (V). A preferred method is by reaction with base, for example, but not limited to, hydroxide ion generated from sodium hydroxide, potassium hydroxide, lithium hydroxide and the like. Reaction conditions include the use of $C_1$-$C_6$ alcohol solvents; ethanol is preferred. A common co-solvent, such as for example, ethyl acetate may also be employed. Reactions are conducted at temperatures ranging from −45 degrees C. up to the reflux temperature of the alcohol employed; preferred temperature ranges are between −20 degrees C. and 20-25 degrees C.

The epoxide (V) is then reacted with the appropriately substituted C-terminal amine, $R_c$—$NH_2$ (VI) by methods known to those skilled in the art that opens the epoxide to produce the desired corresponding enantiomerically pure (S,R)-protected alcohol (VII). The substituted C-terminal amines, $R_c$—$NH_2$ (VI) of this invention are commercially available or are known to those skilled in the art and can be readily prepared from known compounds. $R_C$ is as defined above for formula (I).

It is preferred that $R_C$ is —$C_1$-$C_8$ alkyl, —$(CH_2)_{0-3}$—$(C_3$-$C_7)$cycloalkyl, —$(CR_{12}R_{13})_{0-4}$—$R_{aryl}$, —$(CR_{12}R_{13})_{0-4}$—$R_{heteroaryl}$, —$(CR_{12}R_{13})_{0-4}$—$R_{heterocycle}$, -cyclopentyl or -cyclohexyl ring fused to $R_{aryl}$ or $R_{heteroaryl}$ or $R_{heterocycle}$.

It is more preferred that $R_c$ is —$(CH_2)_{0-3}$—$(C_3$-$C_7)$ cycloalkyl, —$(CR_{12}R_{13})_{0-4}$—$R_{aryl}$, —$(CR_{12}R_{13})_{0-4}$—$R_{C-heteroaryl}$, —$(CR_{12}R_{13})_{0-4}$—$R_{heterocycle}$, -cyclopentyl or -cyclohexyl ring fused to a $R_{aryl}$ or $R_{heteroaryl}$ or $R_{heterocycle}$.

It is even more preferred that $R_c$ is —$(CR_{12}R_{13})_{0-4}$—$R_{aryl}$, —$(CR_{12}R_{13})_{0-4}$—$R_{heteroaryl}$, -cyclopentyl or -cyclohexyl ring fused to a $R_{aryl}$ or $R_{heteroaryl}$ or $R_{heterocycle}$.

It is still more preferred that $R_c$ is selected from the group consisting of —$(CR_{12}R_{13})_{0-4}$—$R_{aryl}$ where $R_{aryl}$ is phenyl, —$(CR_{12}R_{13})_{0-4}$—$R_{heteroaryl}$, -cyclopentyl or -cyclohexyl ring fused to a $R_{aryl}$ or $R_{heteroaryl}$ or $R_{heterocycle}$.

Further, it is preferred that when $R_c$ is phenyl, it is substituted in the 3-position or 3,5-positions.

Suitable reaction conditions for opening the epoxide (V) include running the reaction in a wide range of common and inert solvents. $C_1$-$C_6$ alcohol solvents are preferred and isopropyl alcohol most preferred. The reactions can be run at temperatures ranging from 20-25 degrees C. up to the reflux temperature of the alcohol employed. The preferred temperature range for conducting the reaction is between 50 degrees C. up to the reflux temperature of the alcohol employed. When the substituted C-terminal amine (VI) is a 1-amino-3,5-cis-dimethyl cyclohexyldicarboxylate it is preferrably prepared as follows. To dimethyl-5-aminoisophthalate in acetic acid and methanol, is added rhodium in alumina in a high-pressure bottle. The bottle is saturated with hydrogen at 55 psi and shaken for one week of time. The mixture is then filtered through a layer of diatomaceous earth and rinsed with methanol three times, the solvents are removed under reduced pressure (with heat) to give a concentrate. The concentrate is triturated with ether and filtered again to give the desired C-terminal amine (VI).

When the substituted C-terminal amine (VI) is 1-amino-3,5-cis-dimethoxy cyclohexane it is prepared by following the general procedure above and making non-critical variations but starting wth 3,5-dimethoxyaniline.

When the substituted C-terminal amine (VI) is an aminomethyl group where the substituent on the methyl group is an aryl group, for example $NH_2$—$CH_2$—$R_{C-aryl}$, and $NH_2$—$CH_2$—$R_{C-aryl}$ is not commercially available it is preferrably prepared as follows. A suitable starting material is the (appropriately substituted) aralkyl compound. The first step is bromination of the alkyl substitutent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine (VI) of formula $NH_2$—$CH_2$—$R_{C-aryl}$. The suitably functionalized C-terminal amines (VI) may readily be prepared by one skilled in the art via known methods in the literature, making non-significant modifications. Select literature references include 1) Calderwood, et al., *Tet. Lett.*, 1997, 38, 1241, 2) Ciganek, *J. Org. Chem.*, 1992, 57, 4521, 3) Thurkauf, et al., *J. Med. Chem.*, 1990, 33, 1452, 4) Werner, et al., *Org. Syn., Coll. Vol.* 5, 273, 5) *J. Med. Chem.*, 1999, 42, 4193, 6) *Chem. Rev.* 1995, 95, 2457, 7) *J. Am. Chem. Soc.*, 1986, 3150, 8) Felman et al., *J. Med. Chem.*, 1992, 35, 1183, 9) *J. Am. Chem. Soc.* 1970, 92, 3700, 10) *J. Med. Chem.*, 1997, 40, 2323.

One process to prepare the carboxylic acid ((IX) in CHART A and L in CHART 2A below) used in CHART A is set forth below in CHART 2A.

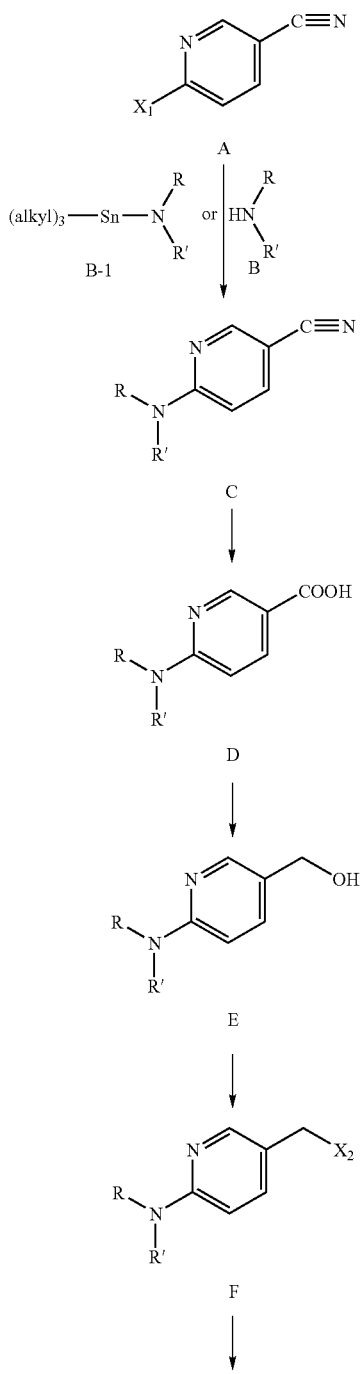

CHART 2A

-continued

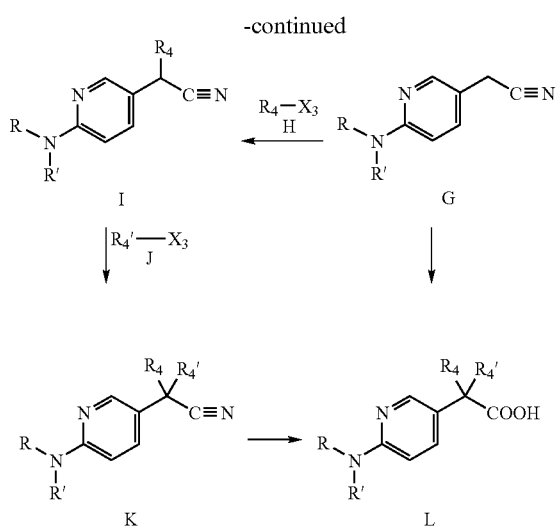

CHART 2A discloses an exemplary method of preparing carboxylic acid (IX and L) starting with commercially available halo nitrile (A), where $X_1$ can be —F, —Cl, —Br, —I, or -Otf; preferably —Cl or —Br. Halo nitrile (A) and amine (B) are stirred, with heating, with solvents such as DMF, THF, NMP, dioxane, toluene and the like at temperatures up to the boiling point of the solvent, or preferably halo nitrile (A) and amine (B) are heated together in a closed vessel in the absence of solvent to give amino nitrile (C). Another method for the conversion of halo nitrile (A) to amino nitrile (C) is by treating halo nitrile (A) with amine (B) in the presence of a catalyst, preferably a palladium catalyst, and a phosphine additive, in the presence of a base, preferably sodium tert-butoxide, and in an inert solvent, preferably toluene, at temperatures between 20-25 degrees and the reflux temperature of the solvent, as is known to those skilled in the art, see for example, *Acc. Chem. Res.* 31, 805, (1998) and *Ang. Chem. Int. Ed. Engl.*, 37, 2046 (1998).

Amine B used herein is commercially available or is known to those skilled in the art and can be readily prepared from known compounds. R and R' are as defined above for formula (I).

Another method for the preparation of amino nitrile (C) is to treat halo nitrile (A) with tin reagent (B-1) in the presence of a palladium catalyst such as tris(dibenzylideneacetone) dipalladium and a phosphine additive, preferably tris(2-methylphenyl)phosphine and an inert solvent such as toluene at temperatures ranging from 50 to 110 degrees, as is known to those skilled in the art, see *J. Am. Chem. Soc.* 116, 7901 (1994), and *J. Am. Chem. Soc.* 116, 5969 (1994). Amino nitrile (C) is then hydrolyzed using mineral acid or an alkaline earth base by methods well known to those versed in the art to give amine acid (D). Amine acid (D) is then reduced to alcohol (E) in an inert solvent such as THF, at temperatures from about 20-25 degrees to reflux, using borane in forms such as borane-methyl sulfide complex, borane-THF complex, or by using lithium aluminum hydride in ethereal solvents such as ether or THF. The alcohol of alcohol (E) is then converted to a leaving group $X_2$ (such as iodo, bromo, chloro, tosylate, mesylate, nosylate, and the like) in a solvent (such as THF, dichloromethane, DMF, toluene, ethyl acetate, or acetonitrile) to give halide (F). The leaving group $X_2$ of halide (F) is displaced with nitrile employing reagents such as sodium cyanide, potassium cyanide, and trimethylsilylcyanide in solvents such as THF, DMF, DMSO, NMP, acetonitrile, ethyl acetate and the like to give cyanide (G).

If it is desired to have additional substituents on the carbon adjacent to the acid group of carboxylic acid (IX or L), then cyanide (G) is treated with an alkali metal dialkylamide (preferably lithium diisopropylamide) or an alkali metal bis(trialkylsilyl)amide in inert solvents at temperatures ranging from −78 to 20-25 degrees, followed by halide (H), to give mono substituted nitrile (I). Halide (H) includes $R_4$ where $R_4$ is as defined above for formula (I).

Halide (H) also includes $X_3$ such as iodo, bromo, chloro, tosylate, mesylate, nosylate and the like. Inert solvents that can be used in the step from (G) to (I) may include, but are not limited to, acetonitrile, dialkyl ethers (preferably ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloaalkanes (preferably methylene chloride).

Treatment of monosubstituted nitrile (I) with base as above and addition of halide (J) gives disubstituted nitrile (K). Halide (J) includes $R_4'$, where $R_4'$ is defined as $R_4$, and $X_3$ is as defined above. It should also be understood that $R_4$ and $R'_4$ taken together can be =O. Hydrolysis by the methods discussed above and well known to those versed in the art gives carboxylic acid (L). If it is desired to leave the carbon adjacent to the cyano group of cyanide (G) unsubstituted, then cyanide (G) is hydrolyzed to carboxylic acid (L) using mineral acid or alkaline earth base, by methods well known to those versed in the art.

CHART 2B discloses an exemplary method of producing other carboxylic acids (L), more particularly ones that are substituted in the 2-position by R.

CHART 2B

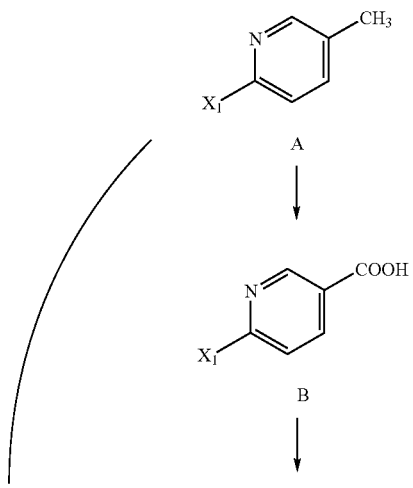

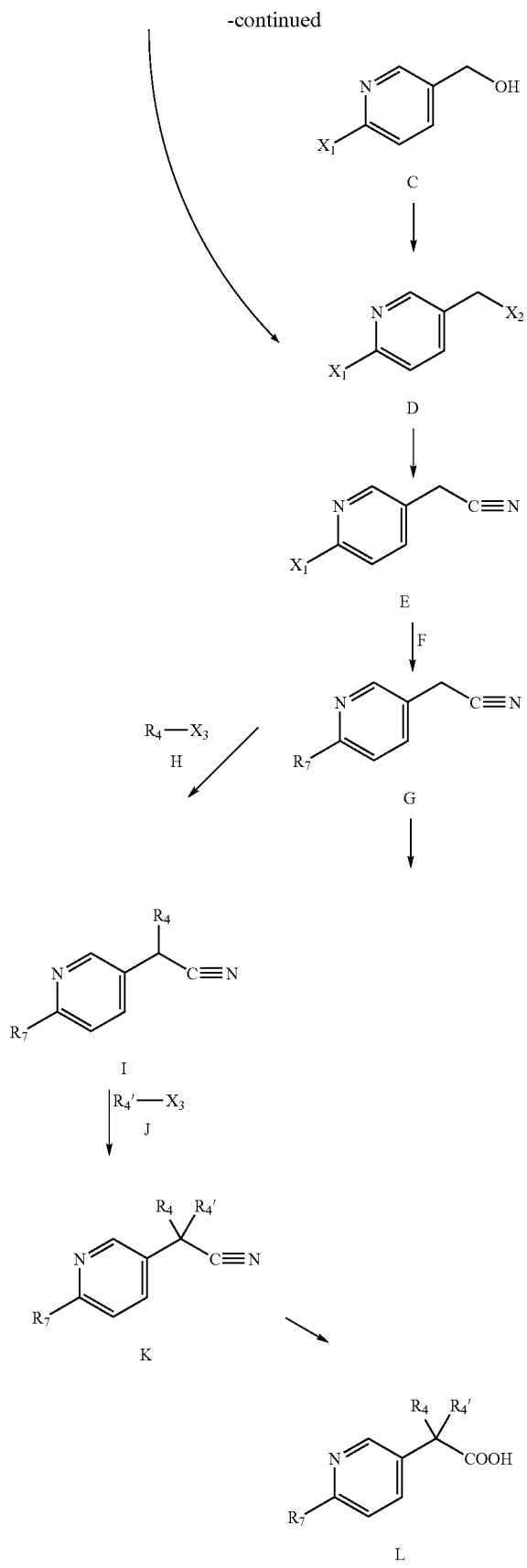

CHART 2B discloses one method of preparing carboxylic acid (L) starting with commercially available 4-methyl-2-substituted pyridine (A), where $X_1$ is halogen, preferably bromine.

4-Methyl-2-substituted pyridine (A) is oxidized to pyridine acid (B) using potassium permanganate in water and alcoholic solvent at temperatures ranging from 20-25 to 100 degrees C. or by methods as discussed in Smith and March, "Advanced Organic Chemistry", Wiley, 2001, p. 1527-1528. Pyridine acid (B) is then reduced to pyridine alcohol (C) using borane in forms such as borane-methyl sulfide complex, borane-THF complex, or using lithium aluminum hydride in ethereal solvents such as ether and THF. The alcohol of pyridine alcohol (C) is then converted to a leaving group $X_2$ (such as iodo, bromo, chloro, tosylate, mesylate, nosylate, triflate, and the like) in solvent (such as THF, dichloromethane, DMF, toluene, ethyl acetate, or acetonitrile) to give pyridine halide (D). Alternatively, 4-methyl-2-substituted pyridine (A) may be halogenated using halogenating agents well known to those versed in the art, including but not limited to, N-halosuccinimide and halogen, preferably N-bromosuccinimide and bromine, and others as taught in Smith and March, "Advanced Organic Chemistry", Wiley, 2001, pp. 907-912, to give halide (D). The leaving group $X_2$ of pyridine halide (D) is displaced with nitrile by employing reagents such as sodium cyanide, potassium cyanide, or trimethylsilylcyanide in solvents such as THF, DMF, DMSO, NMP, acetonitrile, ethyl acetate and the like at temperatures ranging from 20-25 degrees C. to the boiling point of the solvent to give pyridine cyanide (E). Treatment of pyridine cyanide (E) with a boron reagent (F) such as alkylboronic acid, alkyl boronic acid ester, or alkyl boroxines in the presence of a metal catalyst with or without base in an inert solvent gives alkyl pyridine (G). Alkyl pyridine (G) includes $R_7$, where $R_7$ is as defined above for formula (I).

Metal catalysts suitable for these transformations include, but are not limited to, salts or phosphine complexes of copper, lead, or nickel such as $Cu(OAc)_2$, $PdCl_2 (PPh_3)_2$, $NiCl_2 (PPh_3)_2$. Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl) amide), trialkyl amines (preferably diisopropylethylamine or triethylamine) or aromatic amines (preferably pyridine). Inert solvents may include, but are not limited to, acetonitrile, dialkyl ethers (preferably ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from 20-25 degrees C. up to the boiling point of the solvent employed. Non-commercially available boronic acids or boronic acid esters may be obtained from the corresponding optionally substituted aryl halide as described in *Tetrahedron*, 50, 979-988 (1994).

Alkyl pyridine (G) may be converted directly to carboxylic acid (L) using the hydrolysis methods as discussed above for CHART 2A and well known to those versed in the art. If it is desired to have additional substitutions on the carbon adjacent to the acid of carboxylic acid (L), then cyanide (G) is treated with an alkali metal dialkylamide (preferably lithium diisopropylamide) or an alkali metal bis(trialkylsilyl)amide in inert solvents at temperatures ranging from −78 to 20-25 degrees C., followed by halide (H) where $R_4$ and $X_3$ are described as in CHART 2A above, to give mono substituted nitrile (I). Inert solvents may include, but are not limited to, acetonitrile, dialkyl ethers (preferably ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Treatment of monosubstituted nitrile (I) with base as above and addition of halide (J) where $R_4'$ is described as in CHART 2A above, gives disubsituted nitrile (K). Hydrolysis by the methods discussed above and well known to those versed in the art gives carboxylic acid (L).

An exemplary process to prepare the carboxylic acid (L) when G is not nitrogen is set forth in CHART 2C below. $R_6$ and $R'_6$ are as defined above for formula (I).

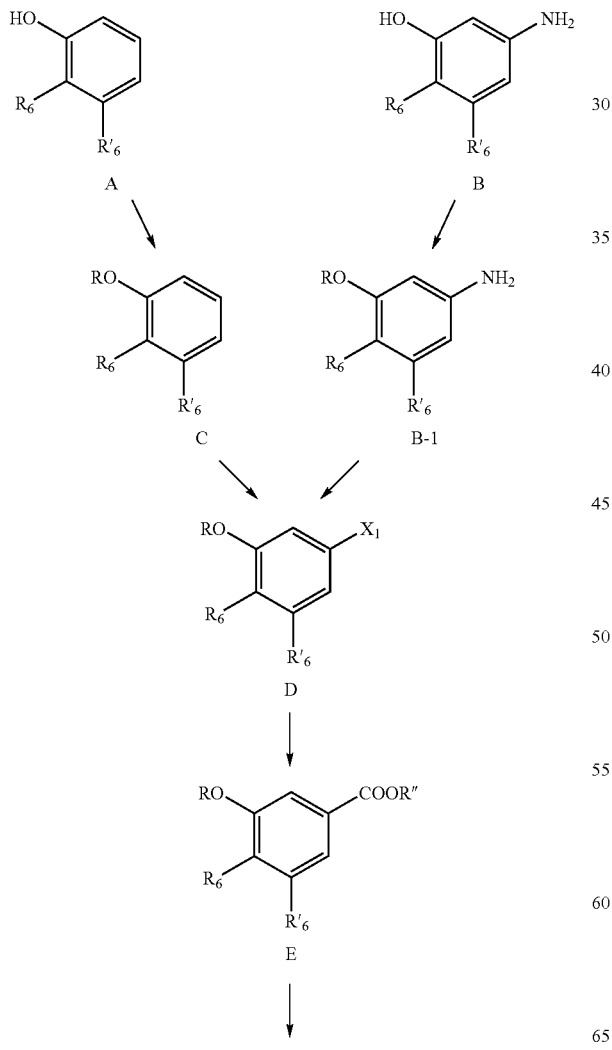

CHART 2C

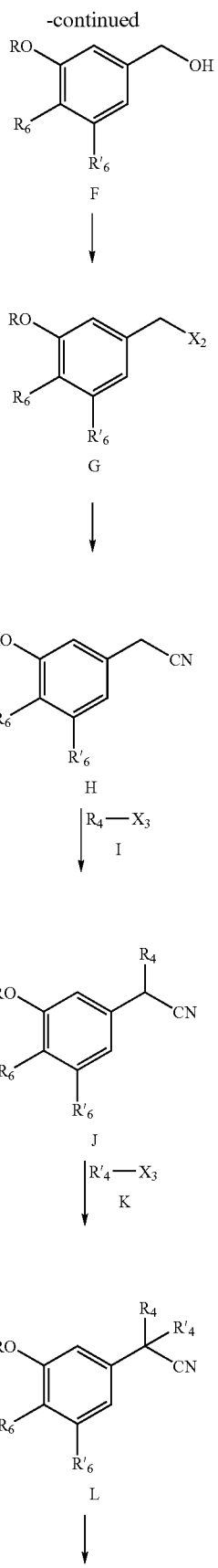

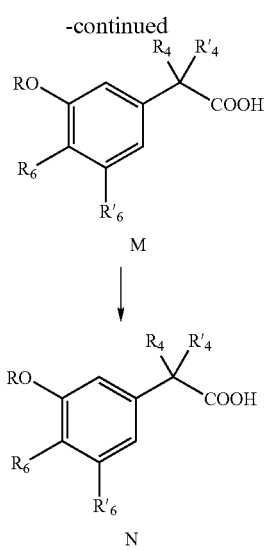

CHART 2C discusses one method of synthesis of phenol acid (N) which begins with commercially available phenol (A) or an aniline phenol (B). $R'_6$ in phenol (A) or aniline phenol (B) encompasses the same components as $R_6$.

When starting with the commercially available phenol (A), the protecting group R in the protected phenol (C) may be chosen from any protecting groups suitable for phenols, such as those taught in Greene and Wuts, Protective Groups in Organic Synthesis, $3^{rd}$ ed., Wiley, 1999, pp. 246-292. Protected phenol (C) is then halogenated to add $X_1$, using chlorine or bromine, preferably bromine, in the presence of a Lewis acid catalyst using methods known to those versed in the art and taught in Smith and March, Advanced Organic Chemistry, Wiley, 2001, pp. 704-707, to give halide (D).

Alternatively, the aniline of an aniline phenol (B) may first be protected with a protecting group (step not shown) and then the phenol of an aniline phenol (B) may be protected with a different protecting group R, such that the protecting group on the aniline may be removed in the presence of the phenol protecting group; such strategies of orthogonal protection are known to those versed in the art; such protecting groups are taught in Greene and Wuts, Protective Groups in Organic Synthesis, $3^{rd}$ ed., Wiley, 1999. Removal of the aniline protecting group then gives a phenol protected aniline (B-1). Phenol protected aniline (B-1) is treated with an alkyl nitrite such as amyl or butyl nitrite in inert solvents such as acetonitrile at temperatures between −60 to 20-25 degrees C., or with sodium nitrite or potassium nitrite in aqueous mineral acids such as aqueous sulfuric acid at temperatures between −60 and 20-25 degrees C. (steps not shown), followed by halide in the form of a halide salt, the preferred salts being potassium bromide or copper bromide, to give halide (D) containing $X_1$ where $X_1$ is a halogen, preferably —Br or —Cl.

Halide (D) obtained by modification of the commercially available phenol (A) or the phenol aniline (B) is then contacted with an alkyl lithium base where the alkyl, represented as R''' in acid (E), includes n-butyl, s-butyl, or t-butyl lithium in an inert solvent, preferably THF, at temperatures ranging from −78 to 0 degrees C., followed by dry carbon dioxide, to give acid (E). Alternatively, halide (D) may be treated with carbon monoxide in the presence of a catalyst, preferably a palladium catalyst, preferably palladium acetate, a phosphine additive, preferably triphenyl phosphine or bis(diphenylphosphino)propane, an alcohol such as methanol or ethanol, and a base, preferably an alkali metal carbonate or alkali metal bicarbonate, at temperatures ranging from 20-25 degrees C. to the reflux temperature of inert solvents such as toluene, DMF, NMP, and dimethylacetamide to give acid (E) where the acid is in the form of an ester.

Acid (E), either as its acid or ester form, may then be reduced to alcohol (F) using lithium aluminum hydride in ethereal solvents such as ethyl ether or THF, or acid (E) may be hydrolyzed to its acid form using methods well known to those versed in the art. Acid (E) in its acid form may also be reduced to alcohol (F) using borane in such forms as borane-THF complex or borane-methyl sulfide complex in ethereal solvents such as THF at temperatures ranging from 50 degrees C. to the reflux temperature of the solvent. The alcohol of alcohol (F) is then converted to a leaving group $X_2$ (such as iodo, bromo, chloro, tosylate, mesylate, nosylate, triflate, and the like) in solvent (such as THF, dichloromethane, DMF, toluene, ethyl acetate, or acetonitrile) at temperatures ranging between −30 and 50 degrees C. to give halo phenol (G).

The leaving group $X_2$ of halo phenol (G) is displaced with nitrile employing reagents such as sodium cyanide, potassium cyanide, or trimethylsilylcyanide in solvents such as THF, DMF, DMSO, NMP, acetonitrile, ethyl acetate and the like at temperatures between 0 and 100 degrees to give nitrile (H).

Nitrile (H) may be converted directly to carboxylic acid (M) using the hydrolysis methods as discussed above for CHART 2A and well known to those versed in the art. If it is desired to have additional substitutions on the carbon adjacent to the acid of carboxylic acid (M), then nitrile (H) is treated with an alkali metal dialkylamide (preferably lithium diisopropylamide) or an alkali metal bis(trialkylsilyl)amide in inert solvents such at temperatures ranging from −78 to 20-25 degrees C., followed by halide (I), where $R_4$ and $X_3$ are as discussed in reference to CHART 2A, to give mono-subsitituted nitrile (J). The inert solvents used may include, but are not limited to, acetonitrile, dialkyl ethers (preferably ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloaalkanes (preferably methylene chloride).

Treatment of mono-substituted nitrile (J) with base as above and addition of halide (K), where $R_4'$ and $X_3$ are as discussed in reference to CHART 2A, gives di-subsituted nitrile (L). Hydrolysis by the methods discussed above and well known to those versed in the art gives carboxylic acid (M). Removal of the protecting group of carboxylic acid (M) using, but not limited to, methods taught in Greene and Wuts, Protective Groups in Organic Synthesis, $3^{rd}$ ed., Wiley, 1999, pp. 246-292, gives acid (N).

The compounds produced as in CHARTS 2A, 2B and 2C are then used in the synthesis of compounds of formula (I) as exemplified by CHART A.

Examples of processes for the preparation of N-(3-amino-2-hydroxy-propyl)-cycloalkyl- and heterocyclyl-alkylamide compounds of formula (I), formula (Ic) and (Id) are set forth in CHARTS 2A through 2E, which are described in greater detail hereinbelow. For purposes of the schemes, $R_7$, $R_8'$ and $R_8''$ are as defined above for $R_6$, $R'_6$ and $R''_6$ in formula; and R, $R_1$, $R_2$, $R_3$ and $R_c$ are as defined above for formula (I).

CHART 3A (3-Oxopiperazine; R7)
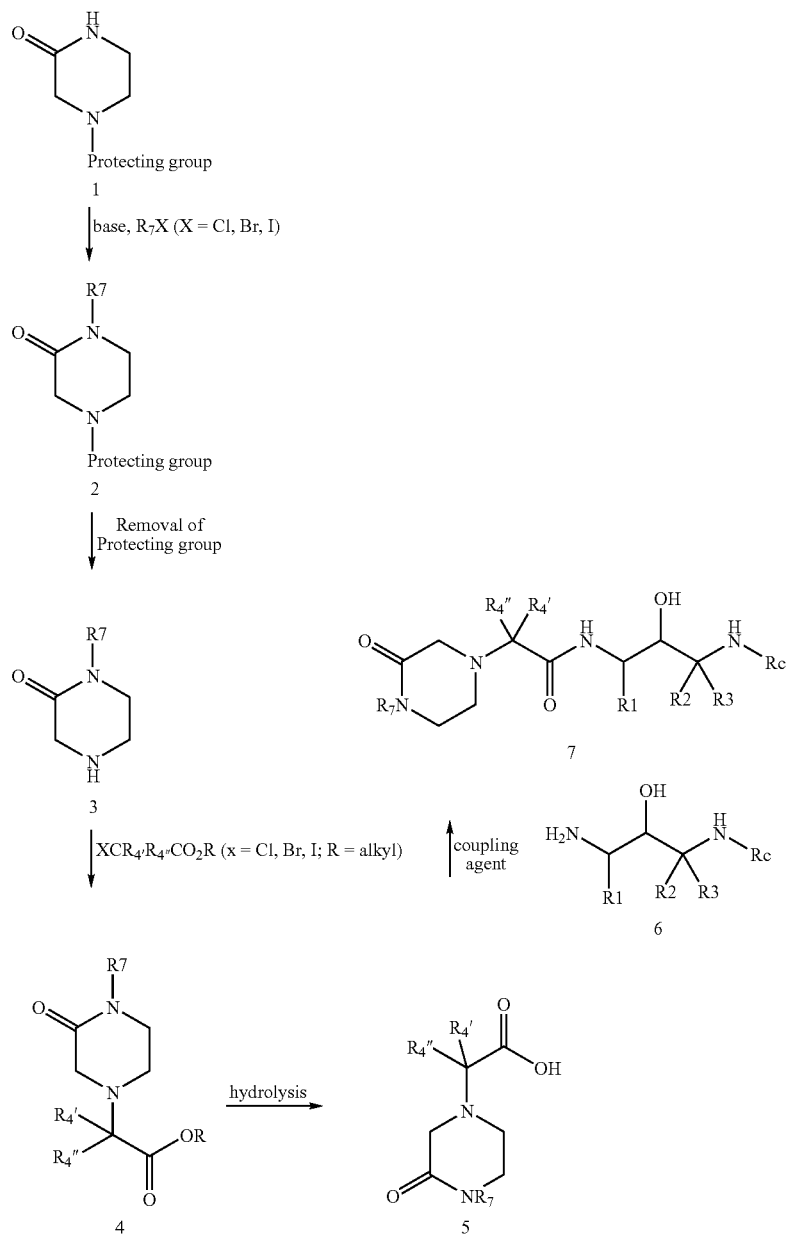
CHART 3B (3-Oxopiperazine-Disubstituted; R7, R8)
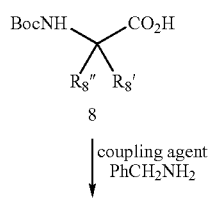

-continued
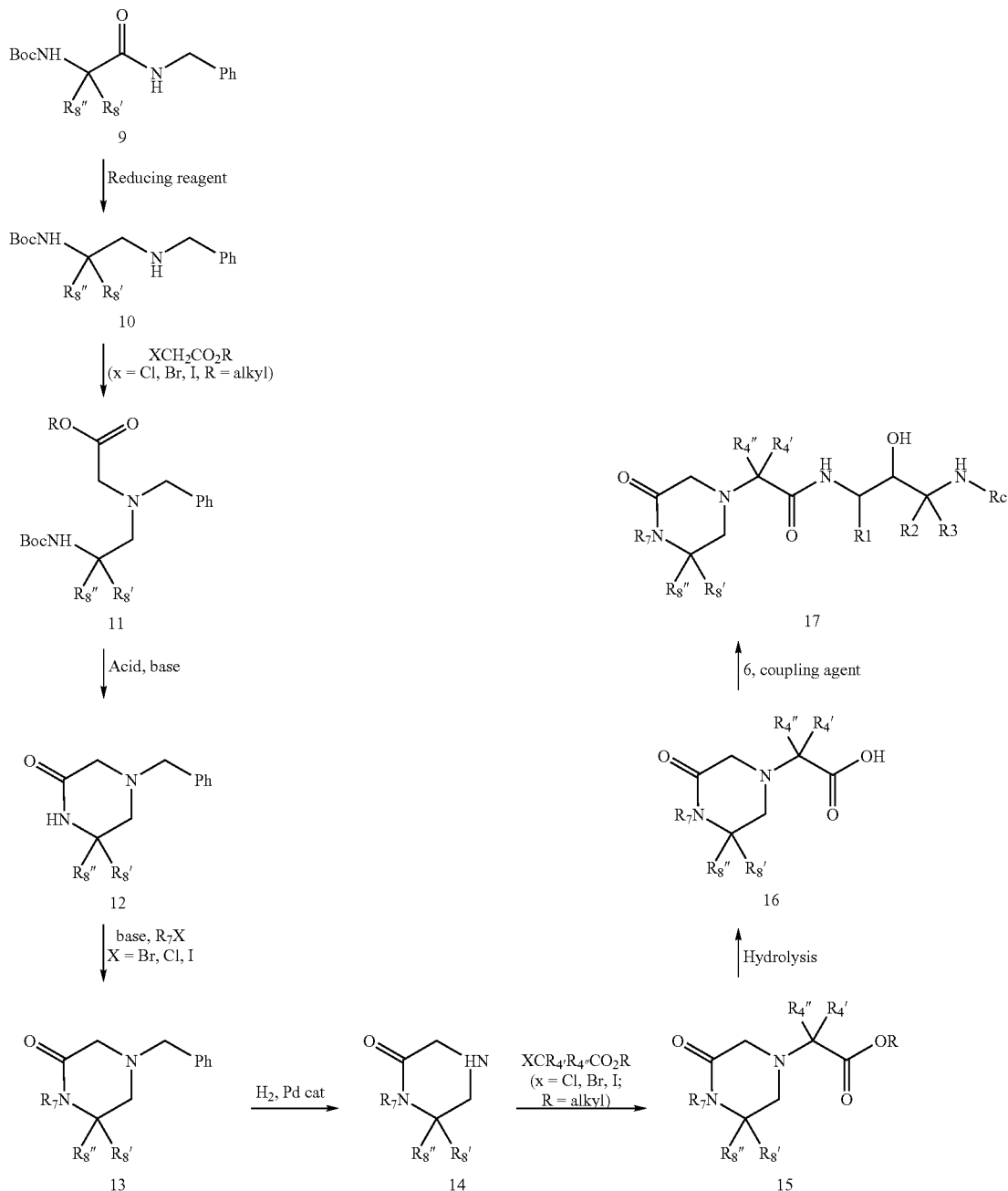
CHART 3C (2,5-Dioxopiperazine, R7, R8)
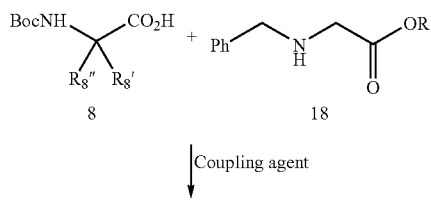

-continued
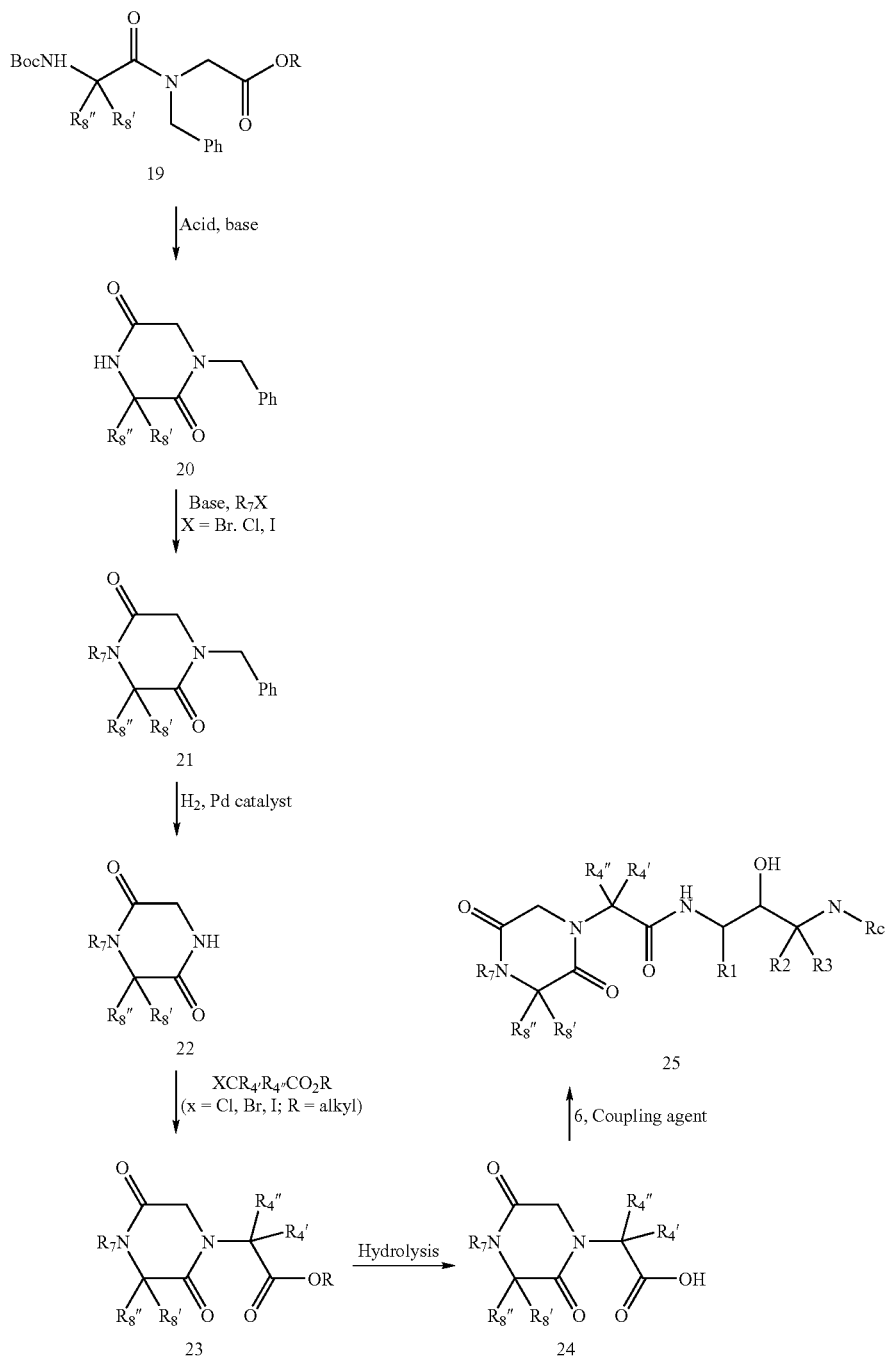
CHART 3D (2,3-Dioxopiperazine, R7, R8)
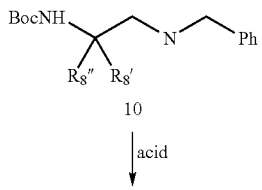

-continued
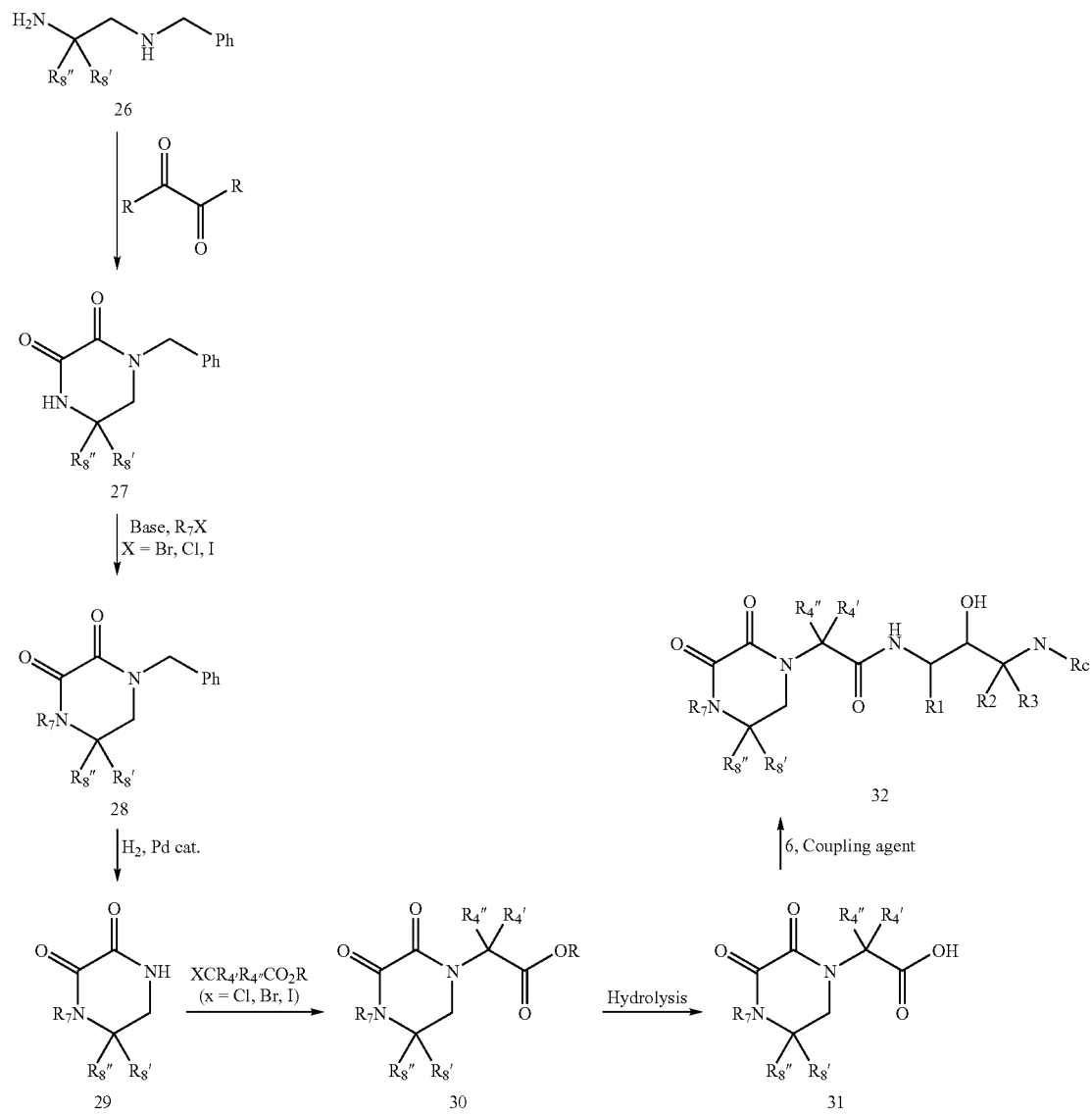
CHART 3E (3,5-Dioxopiperazine, R7)
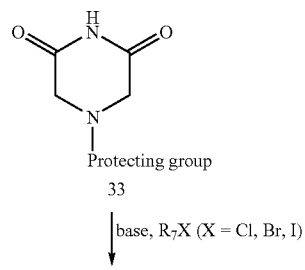

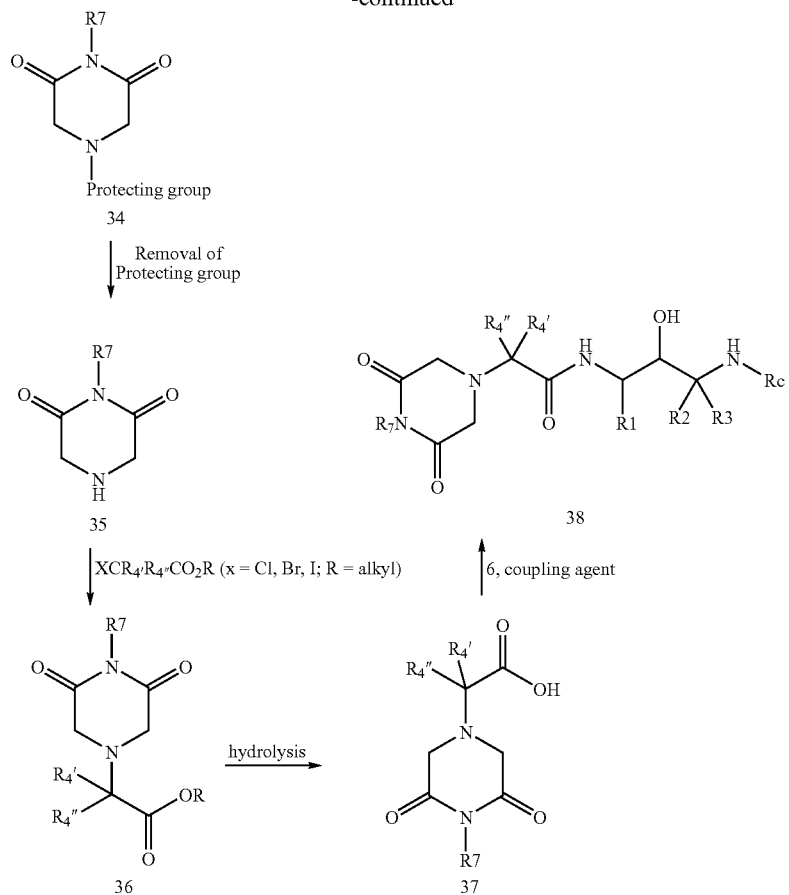

CHART 3A discloses a process to prepare hydroxyethylamine compounds of Formula (I) having an oxopiperazine moiety starting from a suitably protected oxopiperazine. Commercially available oxopiperazine (1) where the protecting group is benzyloxycarbonyl is treated with a base such as sodium hydride and an alkyl halide to provide piperazine (2). The protecting group is removed, for the benzyloxycarbonyl protecting group a palladium catalyst and hydrogen is used, to give compound (3). Compound (3) is alkylated with an α-halo alkyl ester to provide intermediate (4), which is hydrolyzed to the acid (5). Oxopiperazine acid (5) is coupled to amine (6) using a coupling agent, many of which are known to those skilled in the art, to provide compound (7), which has Formula (I).

CHART 3B discloses a process to prepare hydroxyethylamine compounds of Formula (I) having an oxopiperazine moiety starting from commercially available, literature or readily available protected amino acid derivatives (a variety of methods can be found in; Synthesis of Optically Active α-Amino Acids, Williams, M. Robert, 1989, Pergamon Press). Commercially available, literature or readily available amino acid (8) is treated with benzylamine and a coupling agent, many which are known to those skilled in the art, to provide derivative (9). Intermediate (9) is reduced with a reducing reagent such as lithium aluminum hydride to give amine (10), which is alkylated with an α-halo alkyl ester to provide (11). Treatment of (11) with an acid such as trifluoroacetic acid gives oxopiperazine (12). Treatment of (12) with a base such as sodium hydride and an alkyl halide gives oxopiperazine (13). Removal of the benzyl group with hydrogen and a palladium catalyst provides intermediate (14), which is alkylated with an α-halo alkyl ester to give compound (15). Hydrolysis of (15) provides the oxopiperazine acid (16). Coupling of acid (16) with amine (6) using a coupling agent, many which are known to those skilled in the art, gives the desired compound (17), which has Formula (I).

CHART 3C discloses a process to prepare hydroxyethylamine compounds of Formula (I) having a dioxopiperazine moiety starting from commercially available, literature or readily available amino acid derivatives (a variety of methods can be found in; Synthesis of Optically Active α-Amino Acids, Williams, M. Robert, 1989, Pergamon Press). Commercially available, literature or readily available amino acid (8) is treated with N-benzylglycine ethyl ester (18) and a coupling agent, many which are known to those skilled in the art, to provide derivative (19). Treatment of (19) with an acid such as trifluoroacetic acid gives dioxopiperazine (20). Treatment of (20) with a base such as sodium hydride and an alkyl halide gives dioxopiperazine (21). Removal of the benzyl group with hydrogen and a palladium catalyst provides intermediate (22), which is alkylated with an alpha-halo alkyl ester to give compound (23). Hydrolysis of (23) provides the acid (24). Coupling of acid (24) with amine (6) using a coupling agent, many of which are known to those skilled in the art, provides the desired compound (25), which has Formula (I).

CHART 3D discloses a process to prepare hydroxyethylamine compounds of Formula (I) having a dioxopiperazine moiety starting from previously described amine (10) of CHART 2B. Amine (10) is treated with acid such as trifluoroacetic acid to provide diamine (26). Condensation with an oxalic acid derivative gives the dioxopiperazine (27). Treatment of (27) with a base such as sodium hydride and an alkyl halide gives dioxopiperazine (28). Removal of the benzyl group with hydrogen and a palladium catalyst provides intermediate (29), which is alkylated with an α-halo alkyl ester to give compound (30). Hydrolysis of (30) provides the acid (31). Coupling of acid (31) with amine (6) using a coupling agent, many of which are known to those skilled in the art, provides the desired compound (32), which has Formula (I).

CHART 3E discloses a process to prepare hydroxyethylamine compounds of Formula (I) having a dioxopiperazine moiety starting from a suitably protected oxopiperazine. Commercially available dioxopiperazine (33), where the protecting group is benzyl, is treated with a base such as potassium carbonate and an alkyl halide to provide dioxopiperazine (34). The protecting group is removed (for the benzyl protecting group a palladium catalyst and hydrogen is used) to give compound (35). Compound (35) is alkylated with an α-halo alkyl ester to provide intermediate (36), which is hydrolyzed to the dioxopiperazine acid (37). Acid (37) is coupled to amine (6) using a coupling agent, many of which are known to those skilled in the art, to provide the desired compound (38), which has Formula (I).

The compounds of formula (I) are amines, and as such form salts when reacted with acids. Pharmaceutically acceptable salts are preferred over the corresponding amines of formula (I) since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include acid addition salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.*, 33, 201-217 (1986) and *J. Pharm. Sci.*, 66(1), 1, (1977).

Methods of the Invention

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the outset of the disease.

Dosage Forms and Amounts

The compounds of the invention can be administered orally, parenternally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

In addition, the compounds of the present invention can also be used with inhibitors of P-glycoproten (P-gp). The use of P-gp inhibitors is known to those skilled in the art. See for example, *Cancer Research*, 53, 4595-4602 (1993), *Clin. Cancer Res.* , 2, 7-12 (1996), *Cancer Research,* 56, 4171-4179 (1996), International Publications WO99/64001 and WO01/10387. The important thing is that the blood level of the P-gp inhibitor be such that it exerts its effect in inhibiting P-gp from decreasing brain blood levels of the compounds of the present invention. To that end the P-gp inhibitor and the compounds of the present invention can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzo-suberane, phenothiazines, acridine derivatives such as GF120918, FK506, VX-710, LY335979, PSC-833, GF-102, 918 and other steroids. It is to be understood that additional agents will be found that do the same function and are also considered to be useful.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

There is nothing novel about the route of administration or the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et.al., 1999, *Mol.Cell.Neurosci.* 14:419-427; Vassar et.al., 1999, *Science* 286:735-741; Yan et.al., 1999, *Nature* 402: 533-537; Sinha et.al., 1999, *Nature* 40:537-540; and Lin et.al., 2000, *PNAS USA* 97:1456-1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described by Kang et.al., 1987, *Nature* 325:733-6, the 770 amino acid isotype described by Kitaguchi et. al., 1981, *Nature* 331:530-532, and variants such as the Swedish Mutation (KM670-1NL) (APP-SW), the London Mutation (V7176F), and others. See, for example, U.S. Pat. No. 5,766, 846 and also Hardy, 1992, *Nature Genet.* 1:233-234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. Such moieties, include for example, an antigenic epitope for antibody binding, a label or other detection moiety, a binding substrate, and the like.

Antibodies

Products characteristic of APP cleavage can be measured by immunoassay using various antibodies, as described, for example, in Pirttila et.al., 1999, *Neuro.Lett.* 249:21-4, and in U.S. Pat. No. 5,612,486. Useful antibodies to detect A beta include, for example, the monoclonal antibody 6E10 (Senetek, St. Louis, Mo.) that specifically recognizes an epitope on amino acids 1-16 of the A beta peptide; antibodies 162 and 164 (New York State Institute for Basic Research, Staten Island, N.Y.) that are specific for human A beta 1-40 and 1-42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015, and 5,811,633, and in Ganes et.al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Definitions/Abbreviations

The following abbreviations/definitions are used interchangeably herein:

All temperatures are in degrees Celsius (° C.).
TLC refers to thin-layer chromatography.
psi refers to pounds/in$^2$.
h refers to hours.
HPLC refers to high pressure liquid chromatography.
THF refers to tetrahydrofuran.
LDA refers to lithium diisopropylamide
DMF refers to dimethylformamide.
DIPEA refers to diisopropylethylamine
EDC refers to ethyl-1-(3-dimethylaminopropyl)carbodiimide or 1-(3-dimethylaminopropyl)-3-ethylcarbodiimide hydrochloride.
HOBt refers to 1-hydroxy benzotriazole.
HOAt refers to 1-Hydroxy-7-azabenzotriazole.
HATU refers to O-(7-Azabenzotriazol-1-yl)-N,N,N',N'-tetramethyluroniumhexafluorophosphate.
NMM refers to N-methylmorpholine.
NBS refers to N-bromosuccinimide.
TEA refers to triethylamine.
BOC refers to 1,1-dimethylethoxy carbonyl or t-butoxycarbonyl, —CO—O—C(CH$_3$)$_3$.
CBZ refers to benzyloxycarbonyl, —CO—O—CH$_2$-phenyl.
FMOC refers to 9-fluorenylmethyl carbonate.
TFA refers to trifluoracetic acid, CF$_3$—COOH.
CDI refers to 1,1'-carbonyldiimidazole.
Saline refers to an aqueous saturated sodium chloride solution.
Chromatography (column and flash chromatography) refers to purification/separation of compounds expressed as (support, eluent). It is understood that the appropriate fractions are pooled and concentrated to give the desired compound(s).
CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (d) downfield from TMS.
IR refers to infrared spectroscopy.
-phenyl refers to phenyl (C$_6$H$_5$).
MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.
HRMS refers to high resolution mass spectrometry.
Ether refers to diethyl ether.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.
When solvent pairs are used, the ratios of solvents used are volume/volume (v/v).
When the solubility of a solid in a solvent is used the ratio of the solid to the solvent is weight/volume (wt/v).
BOP refers to benzotriazol-1-yloxy-tris(dimethylamino) phosphonium hexafluorophosphate.
TBDMSCl refers to t-butyldimethylsilyl chloride.
TBDMSOTf refers to t-butyldimethylsilyl trifluosulfonic acid ester.
Trisomy 21 refers to Down's Syndrome.
APP, amyloid precursor protein, is defined as any APP polypeptide, including APP variants, mutations, and isoforms, for example, as disclosed in U.S. Pat. No. 5,766,846.
A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.
Beta-secretase (BACE1, Asp2, Memapsin 2) is an aspartyl protease that mediates cleavage of APP at the amino-terminal edge of A beta. Human beta-secretase is described, for example, in WO00/17369.
"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.
A therapeutically effective amount is defined as an amount effective to reduce or lessen at least one symptom of the disease being treated or to reduce or delay onset of one or more clinical markers or symptoms of the disease.
The present invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.
Unless defined otherwise, all scientific and technical terms used herein have the same meaning as commonly understood by one of skill in the art to which this invention belongs. The disclosures in this application of all articles and references, including patents, are incorporated herein by reference.
The invention is illustrated further by the following examples which are not to be construed as limiting the invention in scope or spirit to the specific procedures described in them.
The starting materials and various intermediates may be obtained from commercial sources, prepared from commercially available organic compounds, or prepared using well known synthetic methods.

EXAMPLES

Synthesis

Synthesis of N-(3-amino-2-hydroxy-propyl)-aryl and heteroaryl-alkylamides of formula (I), formula (Ia) and formula (Ib)

The following compounds in table 1 are prepared essentially according to the procedures described in the schemes, examples and preparations set forth herein. The names of all compounds herein were generated at least in part by using the Advanced Chemistry Development Inc. (ACD) nomenclature program, IUPAC Name Batch Version 4, 4.5 or 5, or Chemdraw Ultra versions 6.0 or 6.02.

TABLE 1
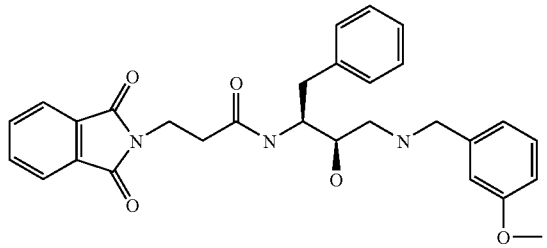
1
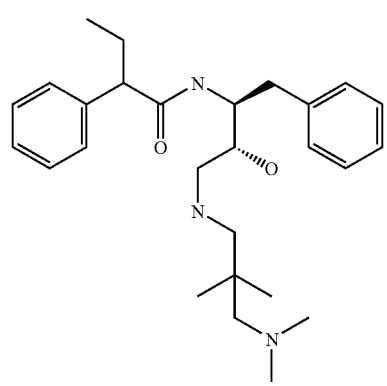
5
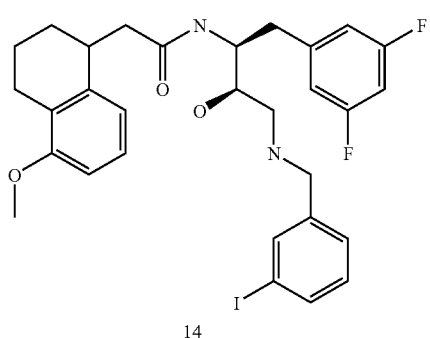
14
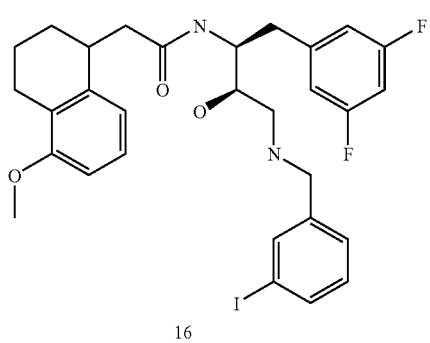
16
TABLE 1-continued
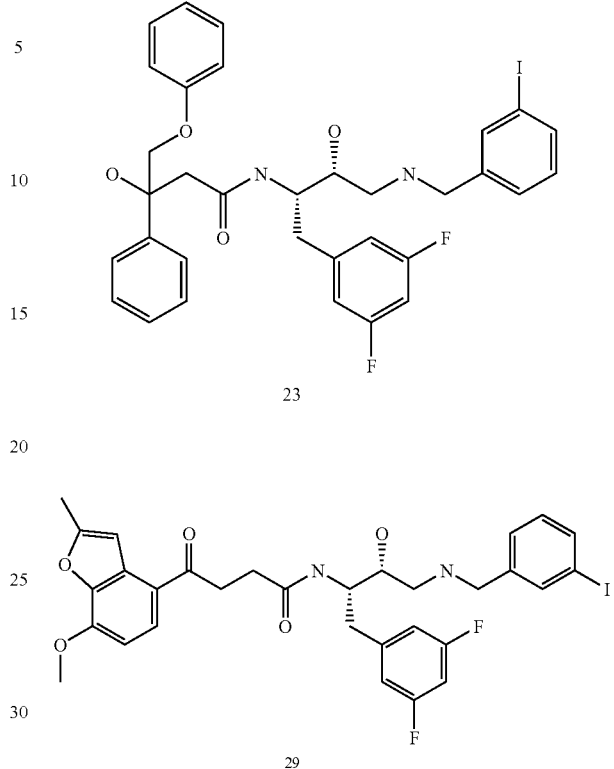
23
29
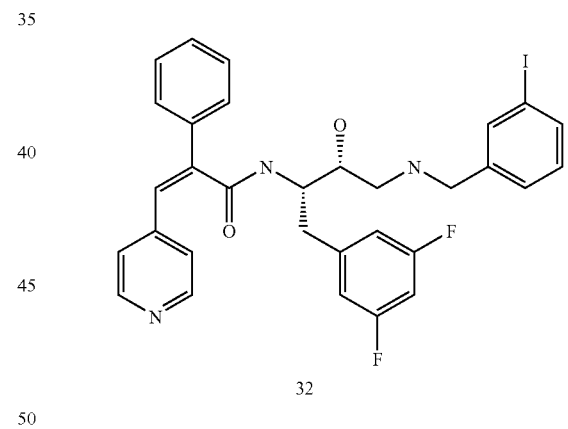
32
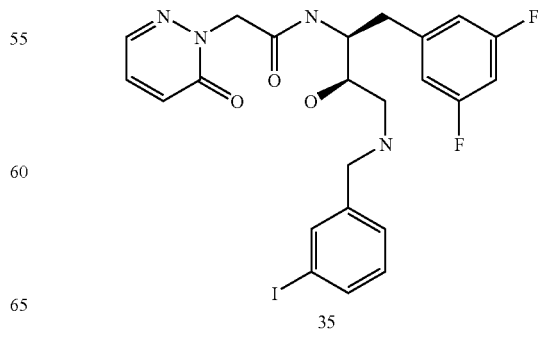
35

TABLE 1-continued
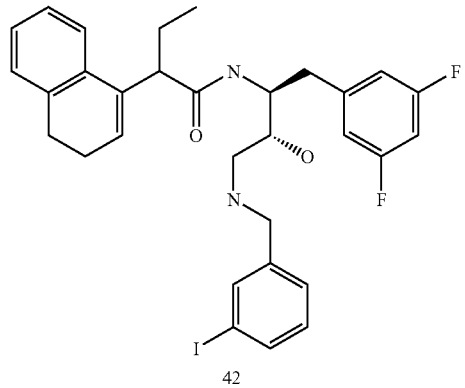
42
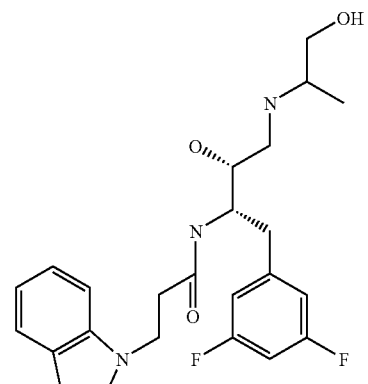
52
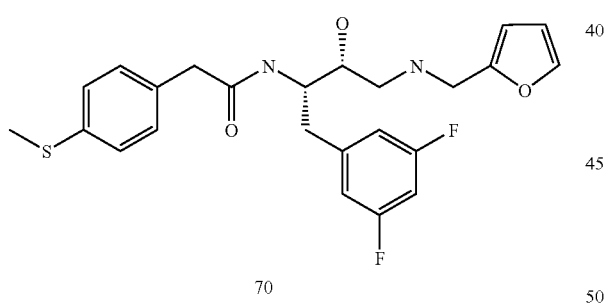
70
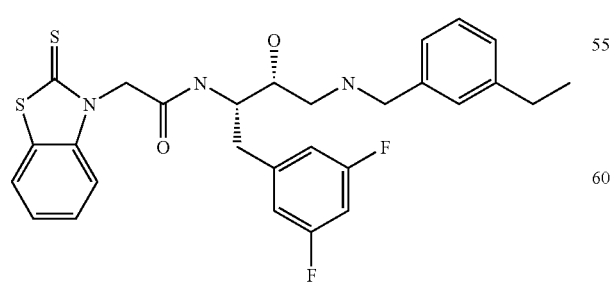
86
TABLE 1-continued
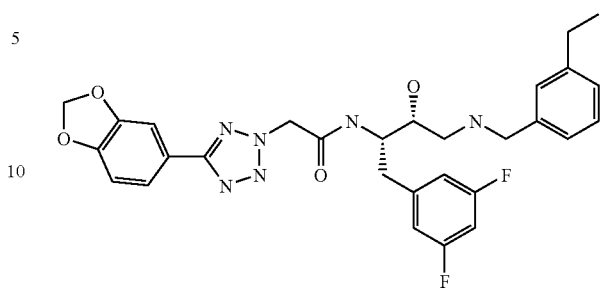
100
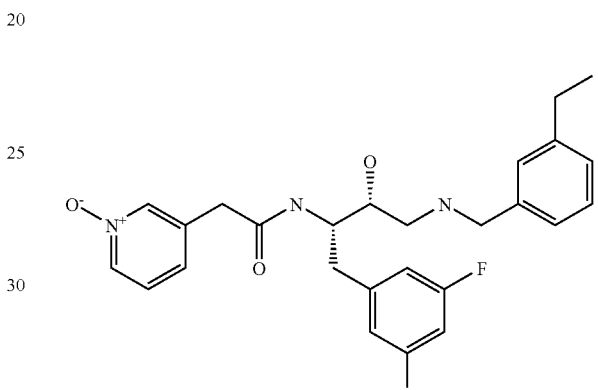
115
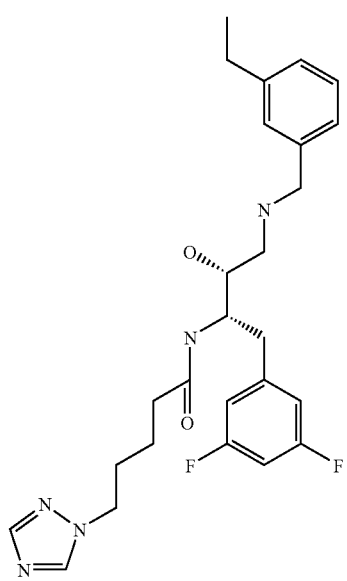
128

TABLE 1-continued

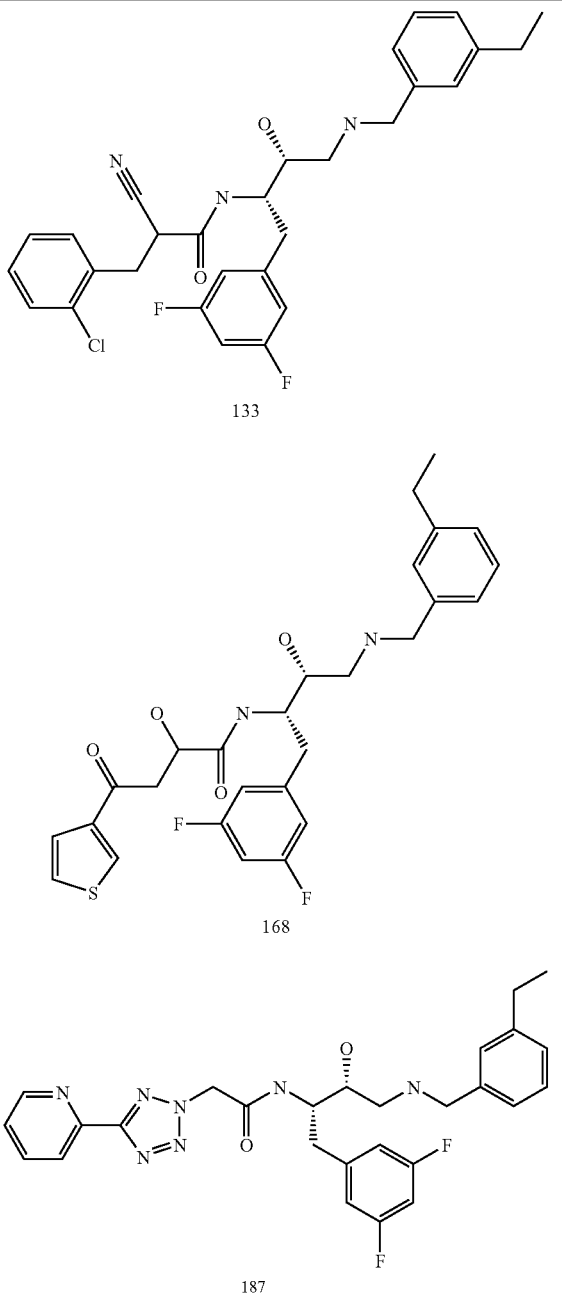

TABLE 2

| Compound No. | Compound Name | MS |
|---|---|---|
| 1 | N-{(1S,2R)-1-benzyl-2-hydroxy-3-[(3-methoxybenzyl)amino]propyl}-3-(1,1-dioxido-3-oxo-1,2-benzisothiazol-2(3H)-yl)propanamide hydrochloride | 538.1994 HRMS calcd 538.2012 |
| 2 | N-{(1S,2R)-1-benzyl-2-hydroxy-3-[(3-methoxybenzyl)amino]propyl}-3-(1,3-dioxo-1,3-dihydro-2H-isoindol-2-yl)propanamide hydrochloride | 488.2177 HRMS calcd 488.2185 |

TABLE 2-continued

| Compound No. | Compound Name | MS |
|---|---|---|
| 3 | N-{(1S,2R)-1-benzyl-2-hydroxy-3-[(3-methoxybenzyl)amino]propyl}-4-(4-fluorophenyl)-4-oxobutanamide hydrochloride | 479.2325 HRMS calcd 479.2346 |
| 4 | N-{(1S,2R)-1-benzyl-3-[(2,3-dimethylcyclohexyl)amino]-2-hydroxypropyl}-3-phenylbutanamide | 437.3 |
| 5 | N-((1S,2R)-1-benzyl-3-{[3-(dimethylamino)-2,2-dimethylpropyl]amino}-2-hydroxypropyl)-2-phenylbutanamide | 440.3 |
| 6 | N-((1S,2R)-1-benzyl-3-{[3-(dimethylamino)-2,2-dimethylpropyl]amino}-2-hydroxypropyl)-3-phenylbutanamide | 440.3 |
| 7 | N-{(1S,2R)-1-benzyl-2-hydroxy-3-[(1-phenylethyl)amino]propyl}-3-phenylbutanamide | 431.3 |
| 8 | N-{(1S,2R)-1-benzyl-2-hydroxy-3-[(1,2,2-trimethylpropyl)amino]propyl}-2-phenylbutanamide | 411.3 |
| 9 | N-{(1S,2R)-1-benzyl-2-hydroxy-3-[(1,2,2-trimethylpropyl)amino]propyl}-3-phenylbutanamide compound with methyl hydroperoxide (1:1) | 411.3 |
| 10 | N-{(1S,2R)-1-benzyl-3-[(1,3-dimethylbutyl)amino]-2-hydroxypropyl}-2-phenylbutanamide compound with methyl hydroperoxide (1:1) | 411.3 |
| 11 | N-{(1S,2R)-1-benzyl-3-[(1,3-dimethylbutyl)amino]-2-hydroxypropyl}-3-phenylbutanamide | 411.3 |
| 12 | N-{(1S,2R)-1-benzyl-3-[(1-ethylpropyl)amino]-2-hydroxypropyl}-2-phenylbutanamide compound with methyl hydroperoxide (1:1) | 397.3 |
| 13 | N-{(1S,2R)-1-benzyl-3-[(1-ethylpropyl)amino]-2-hydroxypropyl}-3-phenylbutanamide | 397.3 |
| 14 | N-{(1S,2R)-1-(3,5-difluorobenzyl)-2-hydroxy-3-[(3-iodobenzyl)amino]propyl}-2-(5-methoxy-1,2,3,4-tetrahydronaphthalen-1-yl)acetamide | 635.82 |
| 15 | 2-[4-(2-amino-2-oxoethoxy)phenyl]-N-{(1S,2R)-1-(3,5-difluorobenzyl)-2-hydroxy-3-[(3-iodobenzyl)amino]propyl}acetamide | 624.33 |
| 16 | N-{(1S,2R)-1-(3,5-difluorobenzyl)-2-hydroxy-3-[(3-iodobenzyl)amino]propyl}-2-[4-(2-oxo-2-pyrrolidin-1-ylethoxy)phenyl]acetamide | 678.58 |
| 17 | N-{(1S,2R)-1-(3,5-difluorobenzyl)-2-hydroxy-3-[(3-iodobenzyl)amino]propyl}-2-{4-[(methylsulfonyl)amino]phenyl}acetamide | 643.86 |

TABLE 2-continued

| Compound No. | Compound Name | MS |
|---|---|---|
| 18 | N-{(1S,2R)-1-(3,5-difluorobenzyl)-2-hydroxy-3-[(3-iodobenzyl)amino]propyl}-4-oxo-4-pyridin-2-ylbutanamide | 594.34 |
| 19 | N-{(1S,2R)-1-(3,5-difluorobenzyl)-2-hydroxy-3-[(3-iodobenzyl)amino]propyl}-2-{4-[2-(4-methylpiperazin-1-yl)ethoxy]phenyl}acetamide | 693.43 |
| 20 | 2-[3-(2-amino-2-oxoethoxy)phenyl]-N-{(1S,2R)-1-(3,5-difluorobenzyl)-2-hydroxy-3-[(3-iodobenzyl)amino]propyl}acetamide | 624.82 |
| 21 | N-{(1S,2R)-1-(3,5-difluorobenzyl)-2-hydroxy-3-[(3-iodobenzyl)amino]propyl}-4-(2,3-dihydro-1H-inden-1-yl)butanamide | 619.51 |
| 22 | N-{(1S,2R)-1-(3,5-difluorobenzyl)-2-hydroxy-3-[(3-iodobenzyl)amino]propyl}-2-methyl-2-(2-methyl-2,3-dihydro-1-benzofuran-5-yl)propanamide | 635.44 |
| 23 | N-{(1S,2R)-1-(3,5-difluorobenzyl)-2-hydroxy-3-[(3-iodobenzyl)amino]propyl}-3-hydroxy-4-phenoxy-3-phenylbutanamide | 687.89 |
| 24 | 2-(1,1'-biphenyl-4-yl)-N-{(1S,2R)-1-(3,5-difluorobenzyl)-2-hydroxy-3-[(3-iodobenzyl)amino]propyl}butanamide | 655.88 |
| 25 | N-{(1S,2R)-1-(3,5-difluorobenzyl)-2-hydroxy-3-[(3-iodobenzyl)amino]propyl}-4-(4-phenoxyphenyl)butanamide | 671.91 |
| 26 | N-{(1S,2R)-1-(3,5-difluorobenzyl)-2-hydroxy-3-[(3-iodobenzyl)amino]propyl}-2-(4-phenoxyphenyl)acetamide | 643.85 |
| 27 | 2-[3-chloro-4-(1-oxo-1,3-dihydro-2H-isoindol-2-yl)phenyl]-N-{(1S,2R)-1-(3,5-difluorobenzyl)-2-hydroxy-3-[(3-iodobenzyl)amino]propyl}propanamide | 730.7 |
| 28 | N-{(1S,2R)-1-(3,5-difluorobenzyl)-2-hydroxy-3-[(3-iodobenzyl)amino]propyl}-4-(2,4-dimethylphenyl)-4-oxobutanamide | 621.78 |
| 29 | N-{(1S,2R)-1-(3,5-difluorobenzyl)-2-hydroxy-3-[(3-iodobenzyl)amino]propyl}-4-(7-methoxy-2-methyl-1-benzofuran-4-yl)-4-oxobutanamide | 677.83 |
| 30 | 4'-[4-({(1S,2R)-1-(3,5-difluorobenzyl)-2-hydroxy-3-[(3-iodobenzyl)amino]propyl}amino)-4-oxobutanoyl]-1,1'-biphenyl-2-carboxamide | 712.97 |
| 31 | N-{(1S,2R)-1-(3,5-difluorobenzyl)-2-hydroxy-3-[(3-iodobenzyl)amino]propyl}-4-{2-[(methylsulfonyl)amino]phenyl}-4-oxobutanamide | 686.89 |
| 32 | (2Z)-N-{(1S,2R)-1-(3,5-difluorobenzyl)-2-hydroxy-3-[(3-iodobenzyl)amino]propyl}-2-phenyl-3-pyridin-4-ylprop-2-enamide | 640.89 |
| 33 | N-{(1S,2R)-1-(3,5-difluorobenzyl)-2-hydroxy-3-[(3-iodobenzyl)amino]propyl}-2-[4-(1,3-dihydro-2H-isoindol-2-yl)phenyl]propanamide | 682.87 |
| 34 | N-{(1S,2R)-1-(3,5-difluorobenzyl)-2-hydroxy-3-[(3-iodobenzyl)amino]propyl}-2-(2,3-dihydro-1H-inden-5-yl)butanamide | 619.91 |
| 35 | N-{(1S,2R)-1-(3,5-difluorobenzyl)-2-hydroxy-3-[(3-iodobenzyl)amino]propyl}-2-(6-oxopyridazin-1(6H)-yl)acetamide | 569.67 |
| 36 | N-{(1S,2R)-1-(3,5-difluorobenzyl)-2-hydroxy-3-[(3-iodobenzyl)amino]propyl}-2-[(methylsulfonyl)amino]-4-phenylbutanamide | 672.93 |
| 37 | N-{(1S,2R)-1-(3,5-difluorobenzyl)-2-hydroxy-3-[(3-iodobenzyl)amino]propyl}-2-(4-hydroxy-5-isopropyl-2-methylphenyl)acetamide | 623.24 |
| 38 | N-{(1S,2R)-1-(3,5-difluorobenzyl)-2-hydroxy-3-[(3-iodobenzyl)amino]propyl}-2-[4-(2-methylprop-1-enyl)phenyl]propanamide | 619.38 |
| 39 | N-{(1S,2R)-1-(3,5-difluorobenzyl)-2-hydroxy-3-[(3-iodobenzyl)amino]propyl}-2-[4-(thien-2-ylcarbonyl)phenyl]propanamide | 675.74 |
| 40 | (2R)-N-{(1S,2R)-1-(3,5-difluorobenzyl)-2-hydroxy-3-[(3-iodobenzyl)amino]propyl}-2-(6-methoxy-2-naphthyl)propanamide | 645.63 |
| 41 | N-{(1S,2R)-1-(3,5-difluorobenzyl)-2-hydroxy-3-[(3-iodobenzyl)amino]propyl}-2-[4-(2-oxopyrrolidin-1-yl)phenyl]acetamide | 634.68 |
| 42 | N-{(1S,2R)-1-(3,5-difluorobenzyl)-2-hydroxy-3-[(3-iodobenzyl)amino]propyl}-2-(3,4-dihydronaphthalen-1-yl)butanamide | 631.75 |
| 43 | N-{(1S,2R)-1-benzyl-2-hydroxy-3-[(3-methoxybenzyl)amino]propyl}-2-(4-isopropylphenyl)acetamide compound with methyl hydroperoxide (1:1) | 461.2 |
| 44 | N-{(1S,2R)-1-benzyl-2-hydroxy-3-[(3-methoxybenzyl)amino]propyl}-2-[4-(methylthio)phenyl]acetamide | 465.2 |
| 45 | N-{(1S,2R)-1-(3,5-difluorobenzyl)-2-hydroxy-3-[(pyridin-2-ylmethyl)amino]propyl}-3-phenylpropanamide | 440.2 |
| 46 | N-{(1S,2R)-1-(3,5-difluorobenzyl)-2-hydroxy-3-[(2-methoxy-1-methylethyl)amino]propyl}-3-phenylpropanamide | 421.2 |

TABLE 2-continued

| Compound No. | Compound Name | MS |
|---|---|---|
| 47 | N-{(1S,2R)-1-(3,5-difluorobenzyl)-2-hydroxy-3-[(2-hydroxy-1-methylethyl)amino]propyl}-3-phenylpropanamide compound with methyl hydroperoxide (1:1) | 407.3 |
| 48 | N-[(1S,2R)-3-(benzylamino)-1-(3,5-difluorobenzyl)-2-hydroxypropyl]-3-phenylpropanamide | 439.3 |
| 49 | N-{(1S,2R)-1-(3,5-difluorobenzyl)-2-hydroxy-3-[(3-methoxybenzyl)amino]propyl}-3-phenylpropanamide | 469.3 |
| 50 | N-{(1S,2R)-1-(3,5-difluorobenzyl)-3-[(2-furylmethyl)amino]-2-hydroxypropyl}-3-phenylpropanamide | 429.3 |
| 51 | N-{(1S,2R)-1-(3,5-difluorobenzyl)-2-hydroxy-3-[(2-methoxy-1-methylethyl)amino]propyl}-3-(1H-indol-1-yl)propanamide compound with methyl hydroperoxide (1:2) | 460.2 |
| 52 | N-{(1S,2R)-1-(3,5-difluorobenzyl)-2-hydroxy-3-[(2-hydroxy-1-methylethyl)amino]propyl}-3-(1H-indol-1-yl)propanamide compound with methyl hydroperoxide (1:2) | 446.3 |
| 53 | N-[(1S,2R)-3-(benzylamino)-1-(3,5-difluorobenzyl)-2-hydroxypropyl]-3-(1H-indol-1-yl)propanamide compound with methyl hydroperoxide (1:2) | 478.2 |
| 54 | N-{(1S,2R)-1-(3,5-difluorobenzyl)-3-[(2-furylmethyl)amino]-2-hydroxypropyl}-3-(1H-indol-1-yl)propanamide | 468.2 |
| 55 | N-[(1S,2R)-3-[(cyclopropylmethyl)amino]-1-(3,5-difluorobenzyl)-2-hydroxypropyl]-3-(1H-indol-1-yl)propanamide | 443.3 |
| 56 | N-{(1S,2R)-1-(3,5-difluorobenzyl)-2-hydroxy-3-[(3-iodobenzyl)amino]propyl}-3-(1H-indol-1-yl)propanamide | 604 |
| 57 | N-{(1S,2R)-1-(3,5-difluorobenzyl)-2-hydroxy-3-[(4-methylbenzyl)amino]propyl}-2-(4-isopropylphenyl)acetamide compound with methyl hydroperoxide (1:1) | 481.3 |
| 58 | N-{(1S,2R)-1-(3,5-difluorobenzyl)-2-hydroxy-3-[(2-methoxy-1-methylethyl)amino]propyl}-2-(4-isopropylphenyl)acetamide | 449.3 |
| 59 | N-{(1S,2R)-1-(3,5-difluorobenzyl)-2-hydroxy-3-[(2-hydroxy-1-methylethyl)amino]propyl}-2-(4-isopropylphenyl)acetamide compound with methyl hydroperoxide (1:1) | 435.3 |
| 60 | N-[(1S,2R)-3-(benzylamino)-1-(3,5-difluorobenzyl)-2-hydroxypropyl]-2-(4-isopropylphenyl)acetamide compound with methyl hydroperoxide (1:1) | 467.3 |
| 61 | N-{(1S,2R)-1-(3,5-difluorobenzyl)-2-hydroxy-3-[(4-methylbenzyl)amino]propyl}-2-[4-(methylthio)phenyl]acetamide compound with methyl hydroperoxide (1:1) | 485.2 |
| 62 | N-{(1S,2R)-1-(3,5-difluorobenzyl)-2-hydroxy-3-[(2-methoxy-1-methylethyl)amino]propyl}-2-[4-(methylthio)phenyl]acetamide | 453.2 |
| 63 | N-{(1S,2R)-1-(3,5-difluorobenzyl)-2-hydroxy-3-[(2-hydroxy-1-methylethyl)amino]propyl}-2-[4-(methylthio)phenyl]acetamide compound with methyl hydroperoxide (1:1) | 439.2 |
| 64 | N-[(1S,2R)-3-(benzylamino)-1-(3,5-difluorobenzyl)-2-hydroxypropyl]-2-[4-(methylthio)phenyl]acetamide compound with methyl hydroperoxide (1:1) | 471.2 |
| 65 | N-{(1S,2R)-1-(3,5-difluorobenzyl)-2-hydroxy-3-[(3-methoxybenzyl)amino]propyl}-2-(4-isopropylphenyl)acetamide compound with methyl hydroperoxide (1:1) | 497.3 |
| 66 | N-[(1S,2R)-3-(butylamino)-1-(3,5-difluorobenzyl)-2-hydroxypropyl]-2-(4-isopropylphenyl)acetamide compound with methyl hydroperoxide (1:1) | 433 |
| 67 | N-((1S,2R)-1-(3,5-difluorobenzyl)-3-{[2-(1,3-dioxolan-2-yl)ethyl]amino}-2-hydroxypropyl)-2-(4-isopropylphenyl)acetamide | 477.3 |
| 68 | N-{(1S,2R)-1-(3,5-difluorobenzyl)-2-hydroxy-3-[(3-iodobenzyl)amino]propyl}-2-(4-isopropylphenyl)acetamide | 593 |
| 69 | N-{(1S,2R)-1-(3,5-difluorobenzyl)-2-hydroxy-3-[(3-methoxybenzyl)amino]propyl}-2-[4-(methylthio)phenyl]acetamide compound with methyl hydroperoxide (1:1) | 400.8 |
| 70 | N-{(1S,2R)-1-(3,5-difluorobenzyl)-3-[(2-furylmethyl)amino]-2-hydroxypropyl}-2-[4-(methylthio)phenyl]acetamide | 461.2 |
| 71 | N-[(1S,2R)-3-(butylamino)-1-(3,5-difluorobenzyl)-2-hydroxypropyl]-2-[4-(methylthio)phenyl]acetamide compound with methyl hydroperoxide (1:1) | 436.9 |
| 72 | N-((1S,2R)-1-(3,5-difluorobenzyl)-3-{[2-(1,3- | 481.2 |

TABLE 2-continued

| Compound No. | Compound Name | MS |
|---|---|---|
| | dioxolan-2-yl)ethyl]amino}-2-hydroxypropyl}-2-[4-(methylthio)phenyl]acetamide | |
| 73 | N-{(1S,2R)-1-(3,5-difluorobenzyl)-2-hydroxy-3-[(3-iodobenzyl)amino]propyl}-2-[4-(methylthio)phenyl]acetamide | 597 |
| 74 | 3-[2-(benzyloxy)-4,6-dimethylphenyl]-N-{(1S,2R)-1-(3,5-difluorobenzyl)-2-hydroxy-3-[(3-iodobenzyl)amino]propyl}-3-methylbutanamide | 727.97 |
| 75 | 2-[4-(benzyloxy)phenyl]-N-{(1S,2R)-1-(3,5-difluorobenzyl)-2-hydroxy-3-[(3-iodobenzyl)amino]propyl}acetamide | 657.33 |
| 76 | N-{(1S,2R)-1-(3,5-difluorobenzyl)-2-hydroxy-3-[(3-iodobenzyl)amino]propyl}-3-(2-fluorophenyl)propanamide | 583.79 |
| 77 | N-{(1S,2R)-1-(3,5-difluorobenzyl)-2-hydroxy-3-[(3-iodobenzyl)amino]propyl}-4-(7-methoxy-2,3-dihydro-1-benzofuran-4-yl)-4-oxobutanamide | 665.89 |
| 78 | N-{(1S,2R)-1-(3,5-difluorobenzyl)-3-[(3-ethylbenzyl)amino]-2-hydroxypropyl}-2-[2-(dipropylamino)pyridin-4-yl]acetamide | 553.4 |
| 79 | N-{(1S,2R)-1-(3,5-difluorobenzyl)-3-[(3-ethylbenzyl)amino]-2-hydroxypropyl}-2-(4-hydroxy-3-methoxyphenyl)acetamide | 499 |
| 80 | N-{(1S,2R)-1-(3,5-difluorobenzyl)-3-[(3-ethylbenzyl)amino]-2-hydroxypropyl}-2-(3-hydroxyphenyl)acetamide | 469.3 |
| 81 | N-{(1S,2R)-1-(3,5-difluorobenzyl)-3-[(3-ethylbenzyl)amino]-2-hydroxypropyl}-2-(3,5-dimethoxyphenyl)acetamide | 513.3 |
| 82 | N-{(1S,2R)-1-(3,5-difluorobenzyl)-3-[(3-ethylbenzyl)amino]-2-hydroxypropyl}-2-(3-thien-2-yl-1H-pyrazol-1-yl)acetamide | 525.4 |
| 83 | N-{(1S,2R)-1-(3,5-difluorobenzyl)-3-[(3-ethylbenzyl)amino]-2-hydroxypropyl}-3-(2-oxo-1,3-benzoxazol-3(2H)-yl)propanamide | 524.5 |
| 84 | 3-(1H-benzimidazol-2-yl)-N-{(1S,2R)-1-(3,5-difluorobenzyl)-3-[(3-ethylbenzyl)amino]-2-hydroxypropyl}-3-hydroxypropanamide | 523.3 |
| 85 | N-{(1S,2R)-1-(3,5-difluorobenzyl)-3-[(3-ethylbenzyl)amino]-2-hydroxypropyl}-2-(4-morpholin-4-ylphenyl)acetamide | 538.5 |
| 86 | N-{(1S,2R)-1-(3,5-difluorobenzyl)-3-[(3-ethylbenzyl)amino]-2-hydroxypropyl}-2-(2-thioxo-1,3-benzothiazol-3(2H)-yl)acetamide | 542.4 |
| 87 | N-{(1S,2R)-1-(3,5-difluorobenzyl)-3-[(3-ethylbenzyl)amino]-2-hydroxypropyl}-3-(3-pyridin-2-yl-1,2,4-oxadiazol-5-yl)propanamide | 536.4 |
| 88 | N-{(1S,2R)-1-(3,5-difluorobenzyl)-3-[(3-ethylbenzyl)amino]-2-hydroxypropyl}-2-(2-ethyl-1H-benzimidazol-1-yl)acetamide | 521.4 |
| 89 | N-{(1S,2R)-1-(3,5-difluorobenzyl)-3-[(3-ethylbenzyl)amino]-2-hydroxypropyl}-2-(5-hydroxy-7-methyl[1,2,4]triazolo[4,3-a]pyrimidin-3-yl)acetamide | 525.3 |
| 90 | N-{(1S,2R)-1-(3,5-difluorobenzyl)-3-[(3-ethylbenzyl)amino]-2-hydroxypropyl}-2-[(4-methyl-4H-1,2,4-triazol-3-yl)thio]-2-phenylacetamide | 566.3 |
| 91 | N-{(1S,2R)-1-(3,5-difluorobenzyl)-3-[(3-ethylbenzyl)amino]-2-hydroxypropyl}-2-[5-(2-methylphenyl)-2H-tetraazol-2-yl]acetamide | 535.5 |
| 92 | 3-(1,3-benzothiazol-2-yl)-N-{(1S,2R)-1-(3,5-difluorobenzyl)-3-[(3-ethylbenzyl)amino]-2-hydroxypropyl}-3-methoxypropanamide | 554.4 |
| 93 | 1-acetyl-N-{(1S,2R)-1-(3,5-difluorobenzyl)-3-[(3-ethylbenzyl)amino]-2-hydroxypropyl}-2-phenylprolinamide | 550.5 |
| 94 | N-{(1S,2R)-1-(3,5-difluorobenzyl)-3-[(3-ethylbenzyl)amino]-2-hydroxypropyl}-2-(2-methyl-2,3-dihydro-1-benzofuran-5-yl)propanamide | 523.4 |
| 95 | N-{(1S,2R)-1-(3,5-difluorobenzyl)-3-[(3-ethylbenzyl)amino]-2-hydroxypropyl}-2-(3-methyl-2-oxo-2,3-dihydro-1H-benzimidazol-1-yl)acetamide | 523.5 |
| 96 | N-{(1S,2R)-1-(3,5-difluorobenzyl)-3-[(3-ethylbenzyl)amino]-2-hydroxypropyl}-3-(6-ethoxy-1H-benzimidazol-2-yl)propanamide | 551.4 |
| 97 | N-{(1S,2R)-1-(3,5-difluorobenzyl)-3-[(3-ethylbenzyl)amino]-2-hydroxypropyl}-4-(2,3-dihydro-1H-indol-1-yl)-4-oxobutanamide | 536.5 |
| 98 | N-{(1S,2R)-1-(3,5-difluorobenzyl)-3-[(3-ethylbenzyl)amino]-2-hydroxypropyl}-4-(2-oxo-1,3-benzoxazol-3(2H)-yl)butanamide | 538.4 |
| 99 | N-{(1S,2R)-1-(3,5-difluorobenzyl)-3-[(3-ethylbenzyl)amino]-2- | 521.3 |

TABLE 2-continued

| Compound No. | Compound Name | MS |
|---|---|---|
| | hydroxypropyl}-2-(5-phenyl-1H-tetraazol-1-yl)acetamide | |
| 100 | 2-[5-(1,3-benzodioxol-5-yl)-2H-tetraazol-2-yl]-N-{(1S,2R)-1-(3,5-difluorobenzyl)-3-[(3-ethylbenzyl)amino]-2-hydroxypropyl}acetamide | 565.4 |
| 101 | 2-(1H-1,2,3-benzotriazol-1-yl)-N-{(1S,2R)-1-(3,5-difluorobenzyl)-3-[(3-ethylbenzyl)amino]-2-hydroxypropyl}hexanamide | 550.5 |
| 102 | 3-(1,3-benzodioxol-5-yl)-N-{(1S,2R)-1-(3,5-difluorobenzyl)-3-[(3-ethylbenzyl)amino]-2-hydroxypropyl}propanamide | 511.5 |
| 103 | N-{(1S,2R)-1-(3,5-difluorobenzyl)-3-[(3-ethylbenzyl)amino]-2-hydroxypropyl}-2-(1,3-dioxo-1,3-dihydro-2H-isoindol-2-yl)acetamide | 522.2 |
| 104 | N-{(1S,2R)-1-(3,5-difluorobenzyl)-3-[(3-ethylbenzyl)amino]-2-hydroxypropyl}-3-(1,3-dioxo-1,3-dihydro-2H-isoindol-2-yl)propanamide | 536.3 |
| 105 | N-{(1S,2R)-1-(3,5-difluorobenzyl)-3-[(3-ethylbenzyl)amino]-2-hydroxypropyl}-4-oxo-4-phenylbutanamide | 495.5 |
| 106 | 2-(5-acetylthien-2-yl)-N-{(1S,2R)-1-(3,5-difluorobenzyl)-3-[(3-ethylbenzyl)amino]-2-hydroxypropyl}acetamide | 501.4 |
| 107 | N-{(1S,2R)-1-(3,5-difluorobenzyl)-3-[(3-ethylbenzyl)amino]-2-hydroxypropyl}-2-thien-2-ylacetamide | 459.3 |
| 108 | N-{(1S,2R)-1-(3,5-difluorobenzyl)-3-[(3-ethylbenzyl)amino]-2-hydroxypropyl}-2-(1,3-dimethyl-2,6-dioxo-1,2,3,6-tetrahydro-7H-purin-7-yl)acetamide | 555.4 |
| 109 | N-{(1S,2R)-1-(3,5-difluorobenzyl)-3-[(3-ethylbenzyl)amino]-2-hydroxypropyl}-4-(3-hydroxyphenyl)-4-oxobutanamide | 511.4 |
| 110 | N-{(1S,2R)-1-(3,5-difluorobenzyl)-3-[(3-ethylbenzyl)amino]-2-hydroxypropyl}-4-(3-methoxyphenyl)-4-oxobutanamide | 525.4 |
| 111 | N-{(1S,2R)-1-(3,5-difluorobenzyl)-3-[(3-ethylbenzyl)amino]-2-hydroxypropyl}-4-(1H-indol-3-yl)-4-oxobutanamide | 534.3 |
| 112 | 2-(1-benzothien-4-yl)-N-{(1S,2R)-1-(3,5-difluorobenzyl)-3-[(3-ethylbenzyl)amino]-2-hydroxypropyl}acetamide | 509.3 |
| 113 | N-{(1S,2R)-1-(3,5-difluorobenzyl)-3-[(3-ethylbenzyl)amino]-2-hydroxypropyl}-2-(1,3-dimethyl-2,6-dioxo-1,2,3,6-tetrahydro-9H-purin-9-yl)acetamide | 555.4 |
| 114 | N-{(1S,2R)-1-(3,5-difluorobenzyl)-3-[(3-ethylbenzyl)amino]-2-hydroxy-2-phenyl-2-thien-2-ylacetamide | 551.4 |
| 115 | N-{(1S,2R)-1-(3,5-difluorobenzyl)-3-[(3-ethylbenzyl)amino]-2-hydroxypropyl}-2-(1-oxidopyridin-3-yl)acetamide | 470.3 |
| 116 | 2-(4-chloro-2-oxo-1,3-benzothiazol-3(2H)-yl)-N-{(1S,2R)-1-(3,5-difluorobenzyl)-3-[(3-ethylbenzyl)amino]-2-hydroxypropyl}acetamide | 560.3 |
| 117 | N-{(1S,2R)-1-(3,5-difluorobenzyl)-3-[(3-ethylbenzyl)amino]-2-hydroxypropyl}-2-(2,4-dihydroxy-1,3-thiazol-5-yl)acetamide | 492.3 |
| 118 | N-{(1S,2R)-1-(3,5-difluorobenzyl)-3-[(3-ethylbenzyl)amino]-2-hydroxypropyl}-2-[2-(4-fluorophenyl)-1,3-benzoxazol-5-yl]acetamide | 588.4 |
| 119 | N-{(1S,2R)-1-(3,5-difluorobenzyl)-3-[(3-ethylbenzyl)amino]-2-hydroxypropyl}-2-(2-pyridin-4-yl-1,3-benzoxazol-5-yl)acetamide | 571.4 |
| 120 | N-{(1S,2R)-1-(3,5-difluorobenzyl)-3-[(3-ethylbenzyl)amino]-2-hydroxypropyl}-2-(2-methyl-1,3-benzoxazol-5-yl)acetamide | 508.5 |
| 121 | 2-(2H-1,2,3-benzotriazol-2-yl)-N-{(1S,2R)-1-(3,5-difluorobenzyl)-3-[(3-ethylbenzyl)amino]-2-hydroxypropyl}butanamide | 522.5 |
| 122 | N-{(1S,2R)-1-(3,5-difluorobenzyl)-3-[(3-ethylbenzyl)amino]-2-hydroxypropyl}-4-(1,3-dioxo-1,3-dihydro-2H-isoindol-2-yl)-2-hydroxybutanamide | 566.4 |
| 123 | 2-[2-(acetylamino)-1,3-thiazol-4-yl]-N-{(1S,2R)-1-(3,5-difluorobenzyl)-3-[(3-ethylbenzyl)amino]-2-hydroxypropyl}acetamide | 517.3 |
| 124 | N-{(1S,2R)-1-(3,5-difluorobenzyl)-3-[(3-ethylbenzyl)amino]-2-hydroxypropyl}-2-(2-pyridin-2-yl-1,3-thiazol-4-yl)acetamide | 537.4 |
| 125 | N-{(1S,2R)-1-(3,5-difluorobenzyl)-3-[(3-ethylbenzyl)amino]-2-hydroxypropyl}-4-{4-[(methylsulfonyl)amino]phenyl}-4-oxobutanamide | 588.4 |
| 126 | N-{(1S,2R)-1-(3,5-difluorobenzyl)-3-[(3-ethylbenzyl)amino]-2-hydroxypropyl}-3-{4- | 560.4 |

TABLE 2-continued

| Compound No. | Compound Name | MS |
|---|---|---|
| | [(methylsulfonyl)amino]phenyl}propanamide | |
| 127 | N-{(1S,2R)-1-(3,5-difluorobenzyl)-3-[(3-ethylbenzyl)amino]-2-hydroxypropyl}-5-(1H-pyrazol-1-yl)pentanamide | 485.4 |
| 128 | N-{(1S,2R)-1-(3,5-difluorobenzyl)-3-[(3-ethylbenzyl)amino]-2-hydroxypropyl}-5-(1H-1,2,4-triazol-1-yl)pentanamide | 486.5 |
| 129 | N-{(1S,2R)-1-(3,5-difluorobenzyl)-3-[(3-ethylbenzyl)amino]-2-hydroxypropyl}-2-(1,3-dioxo-1,3-dihydro-2H-isoindol-2-yl)propanamide | 536.1 |
| 130 | N-{(1S,2R)-1-(3,5-difluorobenzyl)-3-[(3-ethylbenzyl)amino]-2-hydroxypropyl}-4-(1H-imidazol-1-yl)butanamide | 471.3 |
| 131 | N-{(1S,2R)-1-(3,5-difluorobenzyl)-3-[(3-ethylbenzyl)amino]-2-hydroxypropyl}-2-(2,6-dihydroxypyrimidin-4-yl)acetamide | 487.3 |
| 132 | N-{(1S,2R)-1-(3,5-difluorobenzyl)-3-[(3-ethylbenzyl)amino]-2-hydroxypropyl}-4-(3-fluoro-4-methoxyphenyl)-4-oxobutanamide | 543.4 |
| 133 | 3-(2-chlorophenyl)-2-cyano-N-{(1S,2R)-1-(3,5-difluorobenzyl)-3-[(3-ethylbenzyl)amino]-2-hydroxypropyl}propanamide | 526.3 |
| 134 | N-acetyl-N-{(1S,2R)-1-(3,5-difluorobenzyl)-3-[(3-ethylbenzyl)amino]-2-hydroxypropyl}-D-phenylalaninamide | 524.4 |
| 135 | N-{(1S,2R)-1-(3,5-difluorobenzyl)-3-[(3-ethylbenzyl)amino]-2-hydroxypropyl}-4-(4-methylphenyl)-4-oxobutanamide | 509.4 |
| 136 | N-{(1S,2R)-1-(3,5-difluorobenzyl)-3-[(3-ethylbenzyl)amino]-2-hydroxypropyl}-4-(2-hydroxy-5-methylphenyl)-4-oxobutanamide | 525.5 |
| 137 | N-{(1S,2R)-1-(3,5-difluorobenzyl)-3-[(3-ethylbenzyl)amino]-2-hydroxypropyl}-4-oxo-4-thien-2-ylbutanamide | 501.3 |
| 138 | N-{(1S,2R)-1-(3,5-difluorobenzyl)-3-[(3-ethylbenzyl)amino]-2-hydroxypropyl}-4-(2-naphthyl)-4-oxobutanamide | 545.4 |
| 139 | 4-(1,3-benzodioxol-5-yl)-N-{(1S,2R)-1-(3,5-difluorobenzyl)-3-[(3-ethylbenzyl)amino]-2-hydroxypropyl}butanamide | 525.5 |
| 140 | N-{(1S,2R)-1-(3,5-difluorobenzyl)-3-[(3-ethylbenzyl)amino]-2-hydroxypropyl}-4-(3-pyridin-2-yl-1,2,4-oxadiazol-5-yl)butanamide | 550.5 |
| 141 | N-{(1S,2R)-1-(3,5-difluorobenzyl)-3-[(3-ethylbenzyl)amino]-2-hydroxypropyl}-3-[3-(4-methoxyphenyl)-1,2,4-oxadiazol-5-yl]propanamide | 565.5 |
| 142 | N-{(1S,2R)-1-(3,5-difluorobenzyl)-3-[(3-ethylbenzyl)amino]-2-hydroxypropyl}-4-(2-furyl)-4-oxobutanamide | 485.4 |
| 143 | 4-(1,3-benzothiazol-2-yl)-N-{(1S,2R)-1-(3,5-difluorobenzyl)-3-[(3-ethylbenzyl)amino]-2-hydroxypropyl}butanamide | 538.4 |
| 144 | N-acetyl-4-chloro-N-{(1S,2R)-1-(3,5-difluorobenzyl)-3-[(3-ethylbenzyl)amino]-2-hydroxypropyl}phenylalaninamide | 558.3 |
| 145 | 2-(acetylamino)-2-(1H-1,2,3-benzotriazol-1-yl)-N-{(1S,2R)-1-(3,5-difluorobenzyl)-3-[(3-ethylbenzyl)amino]-2-hydroxypropyl}acetamide | 551.4 |
| 146 | N-{(1S,2R)-1-(3,5-difluorobenzyl)-3-[(3-ethylbenzyl)amino]-2-hydroxypropyl}-2-(2-ethyl-4H-[1,2,4]triazolo[1,5-a]benzimidazol-4-yl)acetamide | 561.4 |
| 147 | N-{(1S,2R)-1-(3,5-difluorobenzyl)-3-[(3-ethylbenzyl)amino]-2-hydroxypropyl}-2-methyl-2-(1H-1,2,4-triazol-1-yl)propanamide | 472.4 |
| 148 | N-{(1S,2R)-1-(3,5-difluorobenzyl)-3-[(3-ethylbenzyl)amino]-2-hydroxypropyl}-2-(5-pyrrolidin-1-yl-2H-tetraazol-2-yl)acetamide | 514.4 |
| 149 | N-{(1S,2R)-1-(3,5-difluorobenzyl)-3-[(3-ethylbenzyl)amino]-2-hydroxypropyl}-3-{[(methylamino)carbonyl]amino}-3-thien-3-ylpropanamide | 545.4 |
| 150 | N-{(1S,2R)-1-(3,5-difluorobenzyl)-3-[(3-ethylbenzyl)amino]-2-hydroxypropyl}-2-[1-methyl-3-(methylthio)-1H-indol-2-yl]acetamide | 552.4 |
| 151 | N-{(1S,2R)-1-(3,5-difluorobenzyl)-3-[(3-ethylbenzyl)amino]-2-hydroxypropyl}-4-(3,4-dihydro-2H-1,5-benzodioxepin-7-yl)-4-oxobutanamide | 567.5 |
| 152 | N-{(1S,2R)-1-(3,5-difluorobenzyl)-3-[(3-ethylbenzyl)amino]-2-hydroxypropyl}-3-[(methoxyacetyl)amino]-3-phenylpropanamide | 554.4 |
| 153 | N-{(1S,2R)-1-(3,5-difluorobenzyl)-3-[(3-ethylbenzyl)amino]-2-hydroxypropyl}-3-[2-oxo-5-(trifluoromethyl)pyridin-1(2H)-yl]propanamide | 552.5 |

TABLE 2-continued

| Compound No. | Compound Name | MS |
|---|---|---|
| 154 | 2-cyano-N-{(1S,2R)-1-(3,5-difluorobenzyl)-3-[(3-ethylbenzyl)amino]-2-hydroxypropyl}-3-(3,4-dimethoxyphenyl)-2-methylpropanamide | 566.4 |
| 155 | 4-(3,4-dichlorophenyl)-N-{(1S,2R)-1-(3,5-difluorobenzyl)-3-[(3-ethylbenzyl)amino]-2-hydroxypropyl}-4-oxobutanamide | 563.3 |
| 156 | N-{(1S,2R)-1-(3,5-difluorobenzyl)-3-[(3-ethylbenzyl)amino]-2-hydroxypropyl}-4-(3,4-difluorophenyl)-4-oxobutanamide | 531.5 |
| 157 | N-{(1S,2R)-1-(3,5-difluorobenzyl)-3-[(3-ethylbenzyl)amino]-2-hydroxypropyl}-4-(3,4-difluorophenyl)-2-methyl-4-oxobutanamide | 545.4 |
| 158 | N-{(1S,2R)-1-(3,5-difluorobenzyl)-3-[(3-ethylbenzyl)amino]-2-hydroxypropyl}-2-hydroxy-4-oxo-4-thien-2-ylbutanamide | 517.6 |
| 159 | N-{(1S,2R)-1-(3,5-difluorobenzyl)-3-[(3-ethylbenzyl)amino]-2-hydroxypropyl}-4-(7-methoxy-1-benzofuran-2-yl)-4-oxobutanamide | 565.4 |
| 160 | 4-dibenzo[b,d]furan-2-yl-N-{(1S,2R)-1-(3,5-difluorobenzyl)-3-[(3-ethylbenzyl)amino]-2-hydroxypropyl}-4-oxobutanamide | 586.5 |
| 161 | N-{(1S,2R)-1-(3,5-difluorobenzyl)-3-[(3-ethylbenzyl)amino]-2-hydroxypropyl}-2-(6-oxo-3-phenylpyridazin-1(6H)-yl)acetamide | 547.4 |
| 162 | 2-(1H,1'H-2,2'-biimidazol-1-yl)-N-{(1S,2R)-1-(3,5-difluorobenzyl)-3-[(3-ethylbenzyl)amino]-2-hydroxypropyl}acetamide | 509.4 |
| 163 | N-{(1S,2R)-1-(3,5-difluorobenzyl)-3-[(3-ethylbenzyl)amino]-2-hydroxypropyl}-4-(3,4-dihydro-2H-chromen-6-yl)-4-oxobutanamide | 551.5 |
| 164 | N-{(1S,2R)-1-(3,5-difluorobenzyl)-3-[(3-ethylbenzyl)amino]-2-hydroxypropyl}-2-(3-oxo-1,2-benzisothiazol-2(3H)-yl)acetamide | 526.4 |
| 165 | 4-[2-(acetylamino)-4,5-dimethylphenyl]-N-{(1S,2R)-1-(3,5-difluorobenzyl)-3-[(3-ethylbenzyl)amino]-2-hydroxypropyl}-4-oxobutanamide | 580.4 |
| 166 | N-{(1S,2R)-1-(3,5-difluorobenzyl)-3-[(3-ethylbenzyl)amino]-2-hydroxypropyl}-2-(3-oxo-2,3-dihydro-1H-isoindol-1-yl)acetamide | 508.5 |
| 167 | N-{(1S,2R)-1-(3,5-difluorobenzyl)-3-[(3-ethylbenzyl)amino]-2-hydroxypropyl}-4-(4-hydroxyphenyl)-4-oxobutanamide | 511.4 |
| 168 | N-{(1S,2R)-1-(3,5-difluorobenzyl)-3-[(3-ethylbenzyl)amino]-2-hydroxypropyl}-2-hydroxy-4-oxo-4-thien-3-ylbutanamide | 517.4 |
| 169 | N-{(1S,2R)-1-(3,5-difluorobenzyl)-3-[(3-ethylbenzyl)amino]-2-hydroxypropyl}-2-phenyl-2-(1H-pyrrol-1-yl)acetamide | 518.5 |
| 170 | 4-(4-chloro-2-hydroxyphenyl)-N-{(1S,2R)-1-(3,5-difluorobenzyl)-3-[(3-ethylbenzyl)amino]-2-hydroxypropyl}-4-oxobutanamide | 545.4 |
| 171 | N-{(1S,2R)-1-(3,5-difluorobenzyl)-3-[(3-ethylbenzyl)amino]-2-hydroxypropyl}-2-(5-methyl-1,3-dioxo-1,3-dihydro-2H-isoindol-2-yl)acetamide | 536.5 |
| 172 | N-{(1S,2R)-1-(3,5-difluorobenzyl)-3-[(3-ethylbenzyl)amino]-2-hydroxypropyl}-2-(1-oxo-1,3-dihydro-2H-isoindol-2-yl)butanamide | 536.5 |
| 173 | N-{(1S,2R)-1-(3,5-difluorobenzyl)-3-[(3-ethylbenzyl)amino]-2-hydroxypropyl}-2-methyl-2-(1-oxo-1,3-dihydro-2H-isoindol-2-yl)propanamide | 536.4 |
| 174 | N-{(1S,2R)-1-(3,5-difluorobenzyl)-3-[(3-ethylbenzyl)amino]-2-hydroxypropyl}-2-(1-methyl-1H-indol-3-yl)-2-oxoacetamide | 520.4 |
| 175 | N-{(1S,2R)-1-(3,5-difluorobenzyl)-3-[(3-ethylbenzyl)amino]-2-hydroxypropyl}-2-(2-thioxo-2,3-dihydro-1,3-thiazol-4-yl)acetamide | 492.4 |
| 176 | N-{(1S,2R)-1-(3,5-difluorobenzyl)-3-[(3-ethylbenzyl)amino]-2-hydroxypropyl}-2-[4-(1H-pyrrol-1-yl)phenyl]propanamide | 532.4 |
| 177 | 2-(1-benzofuran-2-yl)-N-{(1S,2R)-1-(3,5-difluorobenzyl)-3-[(3-ethylbenzyl)amino]-2-hydroxypropyl}-2-methylpropanamide | 521.4 |
| 178 | 4-(1-benzofuran-2-yl)-N-{(1S,2R)-1-(3,5-difluorobenzyl)-3-[(3-ethylbenzyl)amino]-2-hydroxypropyl}-4-oxobutanamide | 535.4 |
| 179 | N-{(1S,2R)-1-(3,5-difluorobenzyl)-3-[(3-ethylbenzyl)amino]-2-hydroxypropyl}-4-(6-methoxy-1,1'-biphenyl-3-yl)-4-oxobutanamide | 601.4 |

TABLE 2-continued

| Compound No. | Compound Name | MS |
|---|---|---|
| 180 | 3-(3-chloroisoxazol-5-yl)-N-{(1S,2R)-1-(3,5-difluorobenzyl)-3-[(3-ethylbenzyl)amino]-2-hydroxypropyl}propanamide | 492.4 |
| 181 | N-{(1S,2R)-1-(3,5-difluorobenzyl)-3-[(3-ethylbenzyl)amino]-2-hydroxypropyl}-4-(4-methoxyphenyl)-4-oxobutanamide | 525.4 |
| 182 | N-{(1S,2R)-1-(3,5-difluorobenzyl)-3-[(3-ethylbenzyl)amino]-2-hydroxypropyl}-4-(2,3-dihydro-1,4-benzodioxin-6-yl)-4-oxobutanamide | 553.3 |
| 183 | N-{(1S,2R)-1-(3,5-difluorobenzyl)-3-[(3-ethylbenzyl)amino]-2-hydroxypropyl}-3-(2-oxo-2H-1,3-benzoxazin-3(4H)-yl)propanamide | 538.6 |
| 184 | N-{(1S,2R)-1-(3,5-difluorobenzyl)-3-[(3-ethylbenzyl)amino]-2-hydroxypropyl}-2-(2-oxo-2,3-dihydro-1,3-benzoxazol-5-yl)acetamide | 510.4 |
| 185 | N-{(1S,2R)-1-(3,5-difluorobenzyl)-3-[(3-ethylbenzyl)amino]-2-hydroxypropyl}-2-(2-oxo-2,3-dihydro-1H-benzimidazol-5-yl)acetamide | 509.4 |
| 186 | N-{(1S,2R)-1-(3,5-difluorobenzyl)-3-[(3-ethylbenzyl)amino]-2-hydroxypropyl}-4-(5-methyl-1H-pyrrol-2-yl)-4-oxobutanamide | 498.6 |
| 187 | N-{(1S,2R)-1-(3,5-difluorobenzyl)-3-[(3-ethylbenzyl)amino]-2-hydroxypropyl}-2-(5-pyridin-2-yl-2H-tetraazol-2-yl)acetamide | 522.4 |
| 188 | N-{(1S,2R)-1-(3,5-difluorobenzyl)-3-[(3-ethylbenzyl)amino]-2-hydroxypropyl}-2-(5,7-dimethyl[1,2,4]triazolo[1,5-a]pyrimidin-2-yl)acetamide | 523.5 |
| 189 | N-{(1S,2R)-1-(3,5-difluorobenzyl)-3-[(3-ethylbenzyl)amino]-2-hydroxypropyl}-4-[5-(methylsulfinyl)-2,3-dihydro-1H-indol-1-yl]-4-oxobutanamide | 598.4 |
| 190 | N-{(1S,2R)-1-(3,5-difluorobenzyl)-3-[(3-ethylbenzyl)amino]-2-hydroxypropyl}-2-phenyl-2-(4H-1,2,4-triazol-3-ylthio)acetamide | 552.4 |
| 191 | N-{(1S,2R)-1-(3,5-difluorobenzyl)-3-[(3-ethylbenzyl)amino]-2-hydroxypropyl}-2-(5,6-dimethyl-2,4-dioxo-1,2,3,4-tetrahydropyridin-3-yl)acetamide | 514.3 |
| 192 | N-{(1S,2R)-1-(3,5-difluorobenzyl)-3-[(3-ethylbenzyl)amino]-2-hydroxypropyl}-3-(3-oxo-2,1-benzisothiazol-1(3H)-yl)propanamide | 540.4 |
| 193 | N-{(1S,2R)-1-(3,5-difluorobenzyl)-3-[(3-ethylbenzyl)amino]-2-hydroxypropyl}-3-phenyl-2-(1H-tetraazol-1-yl)propanamide | 535.5 |
| 194 | N-{(1S,2R)-1-(3,5-difluorobenzyl)-3-[(3-ethylbenzyl)amino]-2-hydroxypropyl}-2-[5-(4-methylphenyl)-2H-tetraazol-2-yl]acetamide | 535.4 |
| 195 | N-{(1S,2R)-1-(3,5-difluorobenzyl)-3-[(3-ethylbenzyl)amino]-2-hydroxypropyl}-2-(3-hydroxy-4-methylphenyl)acetamide | 483.2 |
| 196 | N'-{(1S,2R)-1-(3,5-difluorobenzyl)-3-[(3-ethylbenzyl)amino]-2-hydroxypropyl}-2-phenyl-N,N-dipropylpentanediamide | |
| 197 | N-{(1S,2R)-1-(3,5-difluorobenzyl)-3-[(3-ethylbenzyl)amino]-2-hydroxypropyl}-2-phenylacetamide | 453 |
| 198 | N-{(1S,2R)-1-(3,5-difluorobenzyl)-3-[(3-ethylbenzyl)amino]-2-hydroxypropyl}-2-(3-fluoro-4-propoxyphenyl)acetamide | 530 |
| 199 | N-{(1S,2R)-1-(3,5-difluorobenzyl)-3-[(3-ethylbenzyl)amino]-2-hydroxypropyl}-2-(3-methoxy-4-propoxyphenyl)acetamide | 541.8 |
| 200 | N-{(1S,2R)-1-(3,5-difluorobenzyl)-3-[(3-ethylbenzyl)amino]-2-hydroxypropyl}-2-(4-ethoxyphenyl)acetamide | 497.6 |
| 201 | N-{(1S,2R)-1-(3,5-difluorobenzyl)-3-[(3-ethylbenzyl)amino]-2-hydroxypropyl}-2-(3-hydroxy-4-methoxyphenyl)acetamide | 499.9 |
| 202 | N-{(1S,2R)-1-(3,5-difluorobenzyl)-2-hydroxy-3-[(3-methoxybenzyl)amino]propyl}-3-phenylpropanamide | 469.3 |
| 203 | N-{(1S,2R)-1-(3,5-difluorobenzyl)-3-[(3-ethylbenzyl)amino]-2-hydroxypropyl}-3-phenylpropanamide | 467.3 |
| 204 | N-{(1S,2R)-1-(3,5-difluorobenzyl)-3-[(3-ethylbenzyl)amino]-2-hydroxypropyl}-2-[1-methyl-5-(4-methylbenzoyl)-1H-pyrrol-2-yl]acetamide | 574.3 |
| 205 | 3-(1-butyl-1H-pyrazol-4-yl)-N-{(1S,2R)-1-(3,5-difluorobenzyl)-3-[(3-ethylbenzyl)amino]-2-hydroxypropyl}propanamide | 513.3 |

Synthesis of N-(3-amino-2-hydroxy-propyl)-cycloalkyl and heterocyclyl-alkylamides of formula (I), formula (Ic) and formula (Id)

Example 1

Synthesis of 2-(4-butyl-2,3-dioxopiperazin-1-yl)-N-{(1S,2R)-1-(3,5-difluorobenzyl)-3-[(3-ethylbenzyl)amino]-2-hydroxypropyl}acetamide hydrochloride (206)

Step A (4-Butyl-2,3-dioxo-piperazin-1-yl)-acetic acid

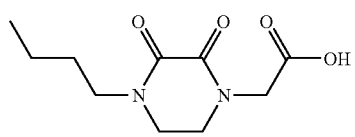

i

N-butylethylenediamine (2.0 mL, 14 mmol) and diethyloxalate (2.1 mL, 15 mmol) are added simultaneously to ice-cold iPrOH (30 mL) under nitrogen. The resultant solution is warmed to ambient temperature and then heated to reflux for 6 hours. The mixture is then concentrated and purified by flash chromatography eluting with 0.10 MeOH:0.01 7N $NH_3$ in MeOH:0.89 $CH_2Cl_2$ to give a white oily solid piperazine. This piperazine (2.4 g, 14 mmol) is dissolved in dry DMF (25 mL), cooled to 0° C., and placed under nitrogen. Solid NaH (60% in mineral oil, 0.62 g, 16 mmol) is then added and the resultant mixture stirred at ambient temperature for 0.5 hr. The mixture is placed back over ice and t-butylbromoacetate (2.3 mL, 16 mmol) is slowly added. The resultant solution is stirred for an hour at ambient temperature before it is quenched by the addition of brine and diluted with EtOAc. The phases are separated and the organic phase is further extracted three times with brine, dried over $Na_2SO_4$, and concentrated to give a yellow-orange oil. The product is isolated by column chromatography eluting with 1:1 heptane:EtOAc with 1% of 7N $NH_3$ in methanol to give the ester as a white crystalline solid (1.4 g, 5.0 mmol, 36%) (M+H:285.2). The ester is then converted to the corresponding acid i by adding trifluoroacetic acid (6 mL) to an ice cold solution of the ester (0.52 g, 2.0 mmol) in 10 mL of $CH_2Cl_2$. After stirring for two hours at ambient temperature, the reaction solution is concentrated under high vacuum to give i.

Step B Synthesis of 206

A solution of i (0.12 g, 0.53 mmol), HATU (0.25 g, 0.66 mmol), and HOAT (0.09 g, 0.66 mmol) in 5 mL of dry DMF is stirred for an hour at ambient temperature before a solution of [3-amino-4-(3,5-difluoro-phenyl)-2-hydroxy-butyl]-(4-ethyl-benzyl)-carbamic acid benzyl ester (0.20 g, 0.40 mmol) and diisopropylethylamine (0.3 mL, 1.7 mmol) in 5 mL of dry DMF is introduced. The resultant solution is stirred overnight at ambient temperature. The reaction solution is then quenched with the addition of 1M HCl, diluted with EtOAc, and the phases are separated. The organic is further extracted with 3× 1M HCl, 3× saturated $NaHCO_3$, and 3× brine. The organic phase is then dried over $Na_2SO_4$, concentrated to an orange oil, and purified by column chromatography eluting with 1:1 heptane:EtOAc to give the N-protected product as a white solid (0.06 g, 0.09 mmol, 22%). The N-protected product is then combined with 10% by weight palladium on activated carbon (0.015 g, 20 wt %) in 10 mL of methanol and placed under 4 psi of $H_2$ for 3 hours. The reaction mixture is then filtered, concentrated, and purified by column chromatography eluting with 0.04 MeOH:0.01 7N $NH_3$ in MeOH:0.95 $CH_2Cl_2$ to afford 206 as the free base. The HCl salt is prepared by dissolving the free base in 1 mL of methanol and adding 2 mL of 7N methanolic HCl and concentrating the solution to give 206 as the HCl salt (0.03 g, 0.052 mmol, 60%) (M+H:545.3).

Example 2

Synthesis of 2-(4-ethyl-2,3-dioxopiperazin-1-yl)-N-{(1S,2R)-1-(3,5-difluorobenzyl)-3-[(3-ethylbenzyl)amino]-2-hydroxypropyl}acetamide hydrochloride (207)

Step A (4-Ethyl-2,3-dioxo-piperazin-1-yl)-acetic acid

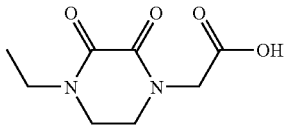

ii

To a solution of N-ethylpiperazin-2,3-dione (1.0 g, 7.0 mmol) in 10 mL of t-butanol over ice is added solid $K_2CO_3$ (1.1 g, 8.0 mmol). After stirring a few minutes t-butylbromoacetate (1.2 mL, 8.1 mmol) is introduced dropwise. The resultant mixture is stirred overnight at ambient temperature. The t-butanol is then azeotroped off with cyclohexane and the residue is partitioned between EtOAc and brine. The phases are separated and the organic phase is extracted 2× 1M HCl, 2× saturated $NaHCO_3$, and 2× brine; dried over $Na_2SO_4$; and concentrated to give the ester as a white solid (0.35 g, 1.4 mmol, 19%). The ester is then converted to the corresponding acid ii by adding trifluoroacetic acid (3 mL) to an ice cold solution of the ester (0.35 g, 1.4 mmol) in 5 mL of $CH_2Cl_2$. After stirring for two hours at ambient temperature the reaction solution is concentrated under high vacuum to give H in quantitative yield.

Step B

A solution of ii (0.27 g, 1.3 mmol), HOBT (0.27 g, 2 mmol) and EDC (0.36 g, 1.9 mmol) in 3 mL of dry DMF is stirred at ambient temperature for 45 minutes. This solution is then added to a solution of [3-amino-4-(3,5-difluoro-phenyl)-2-hydroxy-butyl]-(4-ethyl-benzyl)-carbamic acid benzyl ester (0.63 g, 1.3 mmol) and N-methylmorpholine (0.90 mL, 8.2 mmol) in 3 mL of dry DMF. The resulting solution is then stirred overnight at ambient temperature at which time it is quenched by the addition of saturated $NaHCO_3$ and diluted with EtOAc. The phases are separated and the organic phase is further extracted 1× 1M HCl, 2× saturated $NaHCO_3$, and 2× brine; dried over $Na_2SO_4$; concentrated; and purified by column chromatography eluting with 1:1 heptane:EtOAc (500 mL) then 10% MeOH in $CH_2Cl_2$ to give the protected product. The free base is then prepared by combining the protected product (0.17 g, 0.26 mmol) and Pearlman's catalyst (0.04 g, 20% by wt) in 15 mL of methanol and placing the mixture under 5 psi of $H_2$ for 2.5 hours. The mixture is then filtered, run through a small plug of silica gel, and concentrated to give the free base 207. This is converted to the HCl salt 207 by dissolving the free base 207 in 1 mL of methanol, adding 2 mL of 7N methanolic HCl, and concentrating the solution to give 207 as a white solid (0.13 g, 0.21 mmol, 93%) (M+H: 517.26).

Example 3

Synthesis of 2-(4-butyl-3-oxopiperazin-1-yl)-N-{(1S,2R)-1-(3,5-difluorobenzyl)-3-[(3-ethylbenzyl)amino]-2-hydroxypropyl}acetamide dihydrochloride (208)

Step A 3-Oxo-piperazine-1-carboxylic acid tert-butyl ester

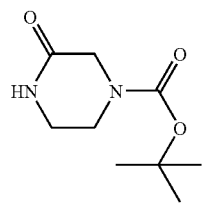

iii

Oxopiperazine (3.38 g, 34 mmol) is dissolved in 20 mL of $CH_2Cl_2$. $Et_3N$ (9.5 mL, 68 mmol) is added followed by $Boc_2O$ (7.4 g, 34 mmol). The solution is allowed to stir at ambient temperature for 3 hours, at which time the reaction is quenched by the addition of brine. The phases are separated and the organic phase is washed with brine, 1 M aqueous $KH_2PO_4$ and dried over $Na_2SO_4$. The mixture is filtered and concentrated to give iii as a white solid (6.1 g, 30 mmol, 90%). (MS: M+H:199.0).

Step B 4-Butyl-3-oxo-piperazine-1-carboxylic acid tert-butyl ester

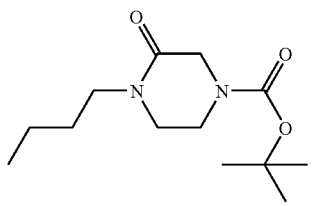

iv

A solution of oxopiperazine iii (6.1 g, 30 mmol) and n-butyl iodide (3.5 mL, 31 mmol) in anhydrous DMF 60 mL) and anhydrous THF (20 mL) is added to an ice cold suspension of sodium hydride (1.32 g, 33 mmol) in 20 mL of anhydrous DMF under a nitrogen atmosphere. The cold bath is removed and the mixture is stirred at ambient temperature for 5 h, at which time it is quenched by the addition of brine and diluted with ethyl acetate. The phases are separated and the organic phase is washed with brine and dried over $Na_2SO_4$. The mixture is filtered and concentrated to give an oil which is purified by flash chromatography on a BIOTAGE 40 M column eluting with 100 mL heptane followed by 3/1/96:MeOH/7N $NH_3$ in MeOH/$CH_2Cl_2$ to give iv as a colorless oil (6.8 g, 27 mmol, 89%). (MS:M+H: 257.4).

Step C 1-Butyl-piperazin-2-one

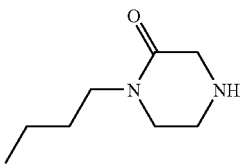

v

Oxopiperazine iv is dissolved in 10 mL of $CH_2Cl_2$ under $N_2$ and 15 mL of TFA is added. The solution is allowed to stir at ambient temperature for 16 h. The solution is concentrated under reduced pressure, dissolved in water, basified by the addition of solid NaOH, and extracted with ethyl acetate. The combined extracts are dried over $Na_2SO_4$. The mixture is filtered and concentrated to give v as an orange oil (3 g, 19 mmol, 76%). (MS:M+H:157.3).

Step D (4-Butyl-3-oxo-piperazin-1-yl)-acetic acid methyl ester

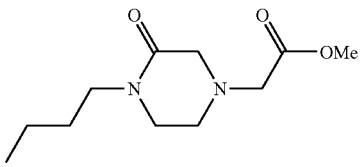

vi

Oxopiperazine v(0.4 g, 2.6 mmol) is combined with diisopropylethylamine (0.55 mL, 3.2 mmol) in 5 mL of methanol over ice, under $N_2$. Methyl bromoacetate (0.27 mL, 2.9 mmol) is added dropwise and the solution is allowed to stir at ambient temperature for 2 hours, at which time it is quenched by the addition of 1 M $KH_2PO_4$ and diluted with ethyl acetate. The phases are separated and the organic phase is washed with 1 M $KH_2PO_4$ and saturated aqueous $NaHCO_3$. The combined aqueous phases are back-extracted with ethyl acetate. The combined organic phases are dried over $Na_2SO_4$. The mixture is filtered and concentrated to give an oil which is purified by flash chromatography on a BIOTAGE 40S column eluting with 500 mL heptane followed by 1/1: heptane/EtOAc and 9/1:$CH_2Cl_2$/MeOH to afford v as colorless oil (0.29 g, 1.3 mmol, 50%). (MS: M+H:229.2).

Step E (4-Butyl-3-oxo-piperazin-1-yl)-acetic acid

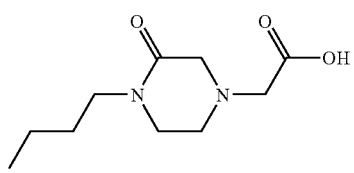

vii

Oxopiperazine vi is dissolved in 5 mL of methanol and a suspension of lithium hydroxide monohydrate (0.3 g, 7.1 mmol) in 5 mL of water is added. The mixture is allowed to stir at ambient temperature for 3 days. The mixture is concentrated under reduced pressure and suspended in water. The mixture is treated with 10 mL acetic acid and extracted with EtOAc. The combined organic extracts are dried over $Na_2SO_4$. The mixture is filtered and concentrated to provide vii as a colorless oil (0.15 g, 0.7 mmol, 56%). (MS:M+H: 215.4)

Step F [3-[2-(4-Butyl-3-oxo-piperazin-1-yl)-acetylamino]-4-(3,5-difluoro-phenyl)-2-hydroxy-butyl]-(3-ethyl-benzyl)-carbamic acid benzyl ester

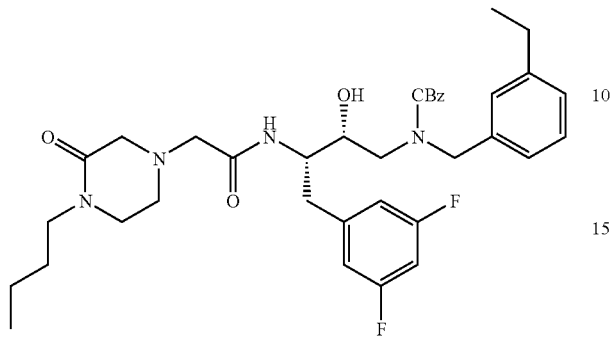

viii

Oxopiperazine vii (0.16 g, 0.75 mmol) is combined with HOAt (0.11 g, 0.81 mmol) and HATU (0.31 g, 0.82 mmol) in 5 mL of dry DMF at 0° C. under $N_2$. After 0.5 h a solution of diisopropylethylamine (0.39 mL, 2.2 mmol) and [3-amino-4-(3,5-difluoro-phenyl)-2-hydroxy-butyl]-(4-ethyl-benzyl)-carbamic acid benzyl ester (0.38 g, 0.81 mmol) in 5 mL anhydrous DMF is added. The solution is allowed to stir for 16 h at ambient temperature. The reaction is quenched by the addition of 1M HCl and diluted with ethyl acetate. The phases are separated and the aqueous layer is extracted with ethyl acetate. The combined organics are washed with 1M HCl, saturated aqueous $NaHCO_3$ and dried over $Na_2SO_4$. The mixture is filtered and concentrated to give an oil which is purified by flash chromatography on a BIOTAGE 40S column eluting with 400 mL of heptane, followed by 1 L of 2/1: heptane/EtOAC and 97/3: $CH_2Cl_2$/MeOH to give H as a yellow oil (0.2 g, 0.3 mmol, 40%). (MS:M+H:665.3)

Step G 208

Oxopiperazine viii is dissolved in 10 mL of methanol and palladium (II) hydroxide (0.04 g) is added. The mixture is hydrogenated at 3 psi for 2 hours, filtered and concentrated to give a colorless oil which is purified by flash chromatography on a BIOTAGE 40S column eluting with 97/3:$CH_2Cl_2$/MeOH followed by 97/3:$CH_2Cl_2$/MeOH and 90/9/1:$CH_2Cl_2$/MeOH/7N $NH_3$ in MeOH to give a colorless oil. The oil is dissolved in 3 mL MeOH and treated with 2 mL 1 N HCl in diether ether. The solvents are removed under reduced pressure to give 208 as the bis HCl salt (0.030 g, 0.05 mmol, 17%). (MS:M+H:531.0).

Example 4

Synthesis of (2R)-2-(4-butyl-3-oxopiperazin-1-yl)-N-{(1S,2R)-1-(3,5-difluorobenzyl)-3-[(3-ethylbenzyl)amino]-2-hydroxypropyl}propanamide (209)

Compound 209 is prepared using the methods described above in Example 3 with the substitution of methyl (s)-2-(trifluoromethylsulfonyloxy)propionate for methyl bromoacetate for the synthesis of intermediate vi. (MS:M+H: 229.2).

Example 5

Synthesis of 2-(1-butyl-2-oxo-1,2-dihydropyridin-4-yl)-N-{(1S,2R)-1-(3,5-difluorobenzyl)-3-[(3-ethylbenzyl)amino]-2-hydroxypropyl}acetamide (210)

Step A 1-Butyl-4-methyl-1H-pyridin-2-one

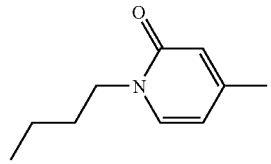

ix

A solution of 2-bromo-4-methylpyridine (7.25 g, 42.1 mmol) and 1-iodobutane (5.8 mL, 50.6 mmol) is heated at 100° C. for 16 h. The residue is triturated with diethyl ether to provide a dark yellow gum. Ethyl alcohol (100 mL) is added followed by the addition of 1 N NaOH (50 mL). The solution is allowed to stir for 4 h and NaOH (1.5 g) is added. After 2 h the solution is partitioned between ethyl acetate and $H_2O$ and separated. The aqueous phase is extracted with ethyl acetate and the combined organics are washed with brine and dried over $MgSO_4$. The mixture is filtered and concentrated to give a dark oil which is purified by flash chromatography (1/1: ethyl acetate/heptane) to provide ix as a yellow oil (2.95 g, 34% 2 steps). (MS:M+H:166.0).

Step B (1-Butyl-2-oxo-1,2-dihydro-pyridin-4-yl)-acetic acid

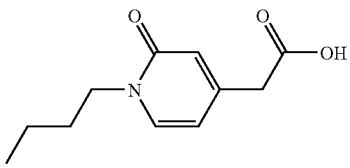

x

A solution of pyridinone ix (1.7 g, 10.3 mmol) in 20 mL anhydrous THF is added dropwise to a solution of LDA (2 M, 5.7 mL, 6.05 mmol) in 40 mL anhydrous THF at −78° C. The solution is allowed to stir for 45 minutes followed by the addition of solid $CO_2$ (10 g). After 0.5 h the mixture is poured onto $H_2O$ and acidified with 1 N HCl. The solution is concentrated under reduced pressure and extracted with ethyl acetate and $CH_2Cl_2$. The combined organics are dried over $MgSO_4$, filtered and concentrated to give a solid which is purified by flash chromatography (9/1:$CH_2Cl_2$/MeOH) to provide x as a white solid (1.4 g, 66%). (MS: M+H: 210.0).

Compound 210 is prepared from x using procedures described above in Example 3. (MS:M+H:526.2).

Example 6

Synthesis of 2-(1-butyl-2-oxopiperidin-4-yl)-N-{(1S, 2R)-1-(3,5-difluorobenzyl)-3-[(3-ethylbenzyl)amino]-2-hydroxypropyl}acetamide (211)

Step A (1-Butyl-2-oxo-piperidin-4-yl)-acetic acid

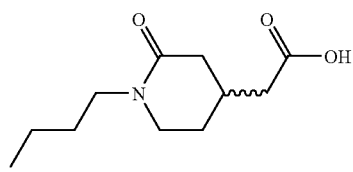

xi

A mixture of pyridinone x (0.81 g, 3.9 mmol), palladium (II) hydroxide (0.84 g) and 15 mL of ethanol is hydrogenated at 33 psi for 4 days. The mixture is filtered to give xi as a colorless oil (0.83 g, 100%). (MS:M+H:214.1).

Compound 211 is prepared from xi using procedures described above in Example 3 (36% yield). (MS:M+H: 530.1).

Example 7

Synthesis of 2-(4-butyl-2,5-dioxopiperazin-1-yl)-N-{(1S,2R)-1-(3,5-difluorobenzyl)-3-[(3-ethylbenzyl)amino]-2-hydroxypropyl}acetamide (212)

Step A [Benzyloxycarbonylmethyl-(2-tert-butoxycarbonylamino-acetyl)-amino]-acetic acid benzyl ester

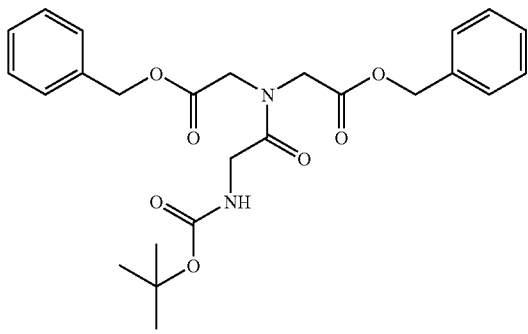

xii

A solution of Boc-glycine (2 g, 11.4 mmol), DIPEA (4 mL, 22.8 mmol) and anhydrous DMF (20 mL) under $N_2$ is cooled with an ice bath. HATU (4.34 g, 11.4 mL) and HOAt (1.55 g, 11.4 mL) are added and after 0.5 h amine R is added. The ice bath is removed and the solution is allowed to stir for 16 h. The solution is partitioned between ethyl acetate and 1 N HCl and separated. The organic layer is washed with aqueous $NaHCO_3$, $H_2O$, brine and dried over $MgSO_4$. The mixture is filtered and concentrated to give xii as a light orange gum (5.05 g, 94%). (MS: M+H: 471.3).

Step B (2,5-Dioxo-piperazin-1-yl)-acetic acid benzyl ester

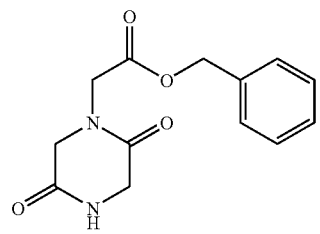

xiii

Intermediate xii (4.8 g, 10.2 mmol) is added to a solution of anhydrous $CH_2Cl_2$ (10 mL) and TFA (10 mL) under $N_2$. After 2 h the solvents are removed under reduced pressure and the residue is partitioned between $CH_2Cl_2$ and aqueous $NaHCO_3$ and separated. The organic layer is dried over $MgSO_4$, filtered and concentrated to give a solid that is triturated with heptane to give xiii as a tan solid (2.0 g, 75%). (MS: M+H: 263.1).

Step C (4-Butyl-2,5-dioxo-piperazin-1-yl)-acetic acid benzyl ester

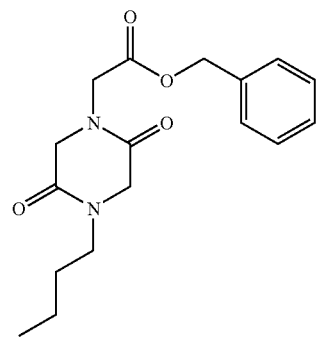

xiv

Dioxopiperazine xiii (1.0 g, 3.81 mmol) is added to a mixture of NaH (60%, 0.18 g, 4.57 mmol) in anhydrous DMF (20 mL) under $N_2$. The mixture turns homogenous and 1-iodobutane (0.48 mL, 4.19 mmol) is added. After 16 h the solution is partitioned between ethyl acetate and $H_2O$ and separated. The aqueous layer is extracted with ethyl acetate and the combined organics are washed with $H_2O$, brine and dried over $MgSO_4$. The mixture is filtered and concentrated to give an oil which is purified by flash chromatography ($CH_2Cl_2$ followed by 98/2:$CH_2Cl_2$/MeOH) to give xiv as a white solid (0.6 g, 50%). (MS: M+H: 319.3).

Step D (4-Butyl-2,5-dioxo-piperazin-1-yl)-acetic acid

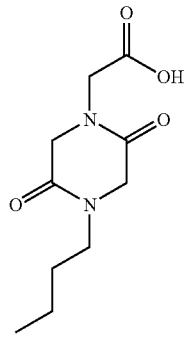

xv

A mixture of dioxopiperazine xiv (0.4 g, 1.26 mmol), 10% Pd/C (0.025 g) and EtOH (10 mL) is hydrogenated at 20 psi for 8 h. The mixture is filtered and concentrated to provide xv as an off-white solid (0.28 g, 97%). (MS: M+H: 229.1).

Compound 212 is prepared from xv using procedures described above in Example 3. (MS:M+H:545.2).

Example 8

Synthesis of N-{(1S,2R)-1-(3,5-difluorobenzyl)-3-[(3-ethylbenzyl)amino]-2-hydroxypropyl}-2-(3-oxo-4-propylcyclohexyl)acetamide (213)

Step A 2-(3-Oxo-4-propyl-cyclohexyl)-malonic acid diethyl ester

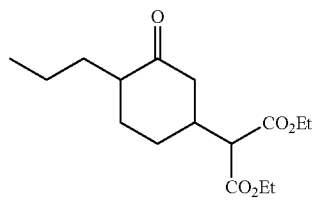

xvi

A solution of sodium metal (30 mg, 1.30 mmol) in absolute ethanol (4.0 mL) is stirred at −10° C. for 0.5 h. Diethyl malonate (3.5 mL, 23 mmol) is added at −10° C. followed by addition of a solution of 6-propyl-cyclohex-2-enone (3.0 g, 21.7 mmol) in absolute ethanol (3.0 mL). The reaction mixture is stirred an additional 12 h at room temperature. The reaction mixture is then acidified to pH 3.0 with 10% hydrogen chloride solution and then extracted several times with diethyl ether. The combined ether extracts are washed with water, and saturated sodium chloride, dried (sodium sulfate), filtered, and concentrated under reduced pressure to yield a yellow oil. Purification by flash column chromatography (silica, 83:17 hexanes/ethyl acetate) gives diester xvi (5.07 g, 91%) as a light yellow oil: $^1$H NMR (300 MHz, CDCl$_3$) δ 4.21 (q, J=7.0 Hz, 2H), 4.20 (q, J=7.0 Hz, 2H), 3.30 (s, 0.5H), 3.28 (s, 0.5H), 2.67-1.55 (m, 8H), 1.43-1.11 (m, 10H), 0.90 (t, J=7.0 Hz, 1.5H), 0.90 (t, J=7.0 Hz, 1.5H).

Step B (3-Oxo-cyclohexyl)-acetic acid

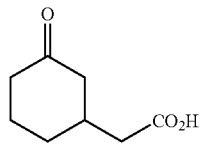

xvii

A solution of diester xvi (2.37 g, 7.94 mmol) in 1 N potassium hydroxide (16.27 mL, 16.27 mmol) is heated at reflux for 2 h. The reaction is cooled to room temperature, diluted with water and extracted with methylene chloride. The aqueous phase is acidified to pH 1-2 with 6 N hydrogen chloride solution and then heated at reflux for 2 h. The reaction is cooled to room temperature and extracted several times with methylene chloride. The combined organic phase is washed with water, saturated sodium chloride, dried (sodium sulfate), filtered, and concentrated under reduced pressure to yield a light yellow oil. Purification by flash column chromatography (silica, 2:1 hexanes/ethyl acetate with 1% glacial acetic acid) gives carboxylic acid xvii (1.42 g, 91%) as a white solid:

$^1$H NMR (300 MHz, CDCl$_3$) δ 2.71-1.12 (m, 14H), 1.11-0.82 (m, 3H); ESI MS m/z 197 [M−H]$^-$.

Step C 213

To a stirred solution of acid xvii (244 mg, 1.23 mmol) and N,N-diisopropyl ethylamine (214 μL, 1.23 mmol) in methylene chloride (7.0 mL) is added HBTU (513 mg, 1.35 mmol) and the reaction mixture stirred for 0.5 h. To the above solution is added a solution of 3-amino-4-(3,5-difluoro-phenyl)-1-(3-ethyl-benzylamino)-butan-2-ol (500 mg, 1.35 mmol) (prepared according to the procedure found in U.S. patent application Ser. No. 09/895,871, filed Jun. 29, 2001) and N,N-diisopropylethylamine (428 μL, 2.46 mmol) in methylene chloride (7.0 mL) and the reaction mixture is stirred under nitrogen for 18 h. The reaction mixture is then diluted with additional methylene chloride and washed with saturated sodium bicarbonate, 0.5 N hydrogen chloride solution, saturated sodium chloride, dried (sodium sulfate), filtered, and concentrated under reduced pressure to yield an oily residue. Purification by flash column chromatography (silica, 7:93 methanol/methylene chloride) gives 213 (360 mg, 33%) as a white solid: mp 52-54° C.; IR (ATR) 2960, 2932, 1698, 1627, 1596, 1533 cm$^{-1}$; $^1$H NMR (500 MHz, CD$_3$OD) δ 7.33-7.30 (m, 2H), 7.25-7.21 (m, 2H), 6.85-6.82 (m, 2H), 6.79-6.63 (m, 1H), 4.08-4.00 (m, 3H), 3.74-3.69 (m, 1H), 3.25-3.19 (m, 1H), 3.06-2.95 (m, 1H), 2.87-2.83 (m, 1H), 2.69-2.64 (m, 2H), 2.62-2.56 (m, 1H), 2.24-2.20 (m, 1H), 2.12-1.95 (m, 5H), 1.69-1.65 (m, 2H), 1.37-1.32 (m, 8H), 1.16-1.08 (m, 2H), 0.92-0.88 (m, 3H); ESI MS m/z 515 [C$_{30}$H$_{40}$F$_2$N$_2$O$_3$+H]$^+$.

Example 9

Synthesis of N-{(1S,2R)-1-(3,5-difluorobenzyl)-3-[(3-ethylbenzyl)amino]-2-hydroxypropyl}-2-(3-oxo-cyclohexyl)acetamide (214)

Step A 2-(3-Oxo-cyclohexyl)-malonic acid diethyl ester

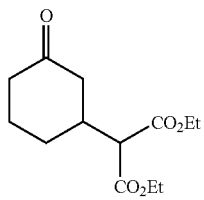

xviii

Diester xviii is prepared in 88% yield from cyclohex-2-enone by the method described for the synthesis of diester xvi above: $^1$H NMR (300 MHz, CDCl$_3$) δ 4.44-4.12 (m, 4H), 2.88-1.22 (m, 16H).

Step B (3-Oxo-cyclohexyl)-acetic acid

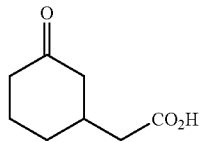

xix

Acid xix is prepared in 70% yield from diester xviii by the method described for the synthesis of xvii above: $^1$H NMR (300 MHz, CDCl$_3$) δ 2.58-1.92 (m, 7H), 1.80-1.61 (m, 1H), 1.52-1.42 (m, 1H); ESI MS m/z 155 [M−H]$^-$.

Step C 214

214 is prepared in 23% yield from acid xix by the method described for the synthesis of 213 (Step C) above: white solid; mp 139.5-149.8° C.; IR (ATR) 3313, 3258, 2940, 1702, 1627, 1595, 1541 cm$^{-1}$; $^1$H NMR (500 MHz, DMSO-d$_6$) δ 7.78-7.74 (m, 1H), 7.22-6.89 (m, 7H), 4.95 (s, 1H), 3.95 (s, 1H), 3.67 (s, 2H), 3.46 (s, 1H), 3.02-2.99 (m, 1H), 2.60-2.54 (m, 4H), 2.20-2.12 (m, 3H), 1.93-1.82 (m, 5H), 1.54-1.36 (m, 2H), 1.18-1.08 (m, 4H); ESI MS m/z 473 [C$_{27}$H$_{34}$F$_2$N$_2$O$_3$+H]$^+$; Anal. Calcd for C$_{27}$H$_{34}$F$_2$N$_2$O$_3$: C, 68.62; H, 7.28; N, 5.93. Found: C, 68.40; H, 7.06; N, 5.85.

Example 10

Synthesis of [3-Amino-4-(3,5-difluoro-phenyl)-2-hydroxy-butyl]-(4-ethyl-benzyl)-carbamic acid benzyl ester To a solution of [1-(3,5-difluoro-benzyl)-3-(3-ethyl-benzylamino)-2-hydroxy-propyl]-carbamic acid tert-butyl ester (16.1 g, 37 mmol) and triethylamine (6.2 mL, 44 mmol) in 80 mL of anhydrous THF under N$_2$ at 0° C. is added benzylchloroformate (5.8 mL, 41 mmol). The solution is warmed to ambient temperature and stirred for 16 h. The solution is quenched with brine and concentrated to remove most of the THF. The residue is diluted with ethyl acetate and separated. The organic phase is washed with 1 M KH$_2$PO$_4$, saturated NaHCO$_3$ and dried over Na$_2$SO$_4$. The mixture is filtered and concentrated to a white solid which is purified on a BIOTAGE 40M column eluting with 400 mL of heptane followed by 4/1:heptane/EtOAc to obtain [3-tert-butoxycarbonylamino-4-(3,5-difluoro-phenyl)-2-hydroxy-butyl]-(3-ethyl-benzyl)-carbamic acid benzyl ester as a white solid (15 g, 26 mmol, 71%), (MS:M+H: 569.4). This compound (6.0 g, 11 mmol) is dissolved in 10 mL of anhydrous CH$_2$Cl$_2$ at 0° C. and 10 mL of TFA is added. The solution is warmed to ambient temperature and stirred for 3 h. The solution is concentrated, diluted with EtOAc and washed with 1M NaOH. The combined organics are dried (Na$_2$SO$_4$) and the mixture is filtered and concentrated to give desired compound as a white solid (5.0 g, 11 mmol, quant. yield), (MS:M+H, 469.5).

Example 11

The following compounds are prepared essentially according to the procedure outlined in CHARTS 3A-E and set forth in Examples 1-10.

(a) N-{(1S,2R)-1-(3,5-difluorobenzyl)-3-[(3-ethylbenzyl)amino]-2-hydroxypropyl}-2-[4-(ethoxymethyl)piperidin-1-yl]hexanamide (compound 215);

(b) (2S)-N-{(1S,2R)-1-(3,5-difluorobenzyl)-3-[(3-ethylbenzyl)amino]-2-hydroxypropyl}-2-[4-(ethoxymethyl)piperidin-1-yl]hexanamide (compound 216);

(c) N-{(1S,2R)-1-(3,5-difluorobenzyl)-3-[(3-ethylbenzyl)amino]-2-hydroxypropyl}-2-[4-(ethoxymethyl)piperidin-1-yl]pentanamide (compound 217);

(d) (2S)-N-{(1S,2R)-1-(3,5-difluorobenzyl)-3-[(3-ethylbenzyl)amino]-2-hydroxypropyl}-2-[4-(ethoxymethyl)piperidin-1-yl]pentanamide (compound 218);

(e) N-{(1S,2R)-1-(3,5-difluorobenzyl)-3-[(3-ethylbenzyl)amino]-2-hydroxypropyl}-2-[4-(ethoxymethyl)piperidin-1-yl]-4-(methylthio)butanamide (compound 219);

(f) (2S)-N-{(1S,2R)-1-(3,5-difluorobenzyl)-3-[(3-ethylbenzyl)amino]-2-hydroxypropyl}-2-[4-(ethoxymethyl)piperidin-1-yl]-4-(methylthio)butanamide (compound 220);

(g) 2-(4-butyl-2-oxopiperazin-1-yl)-N-{(1S,2R)-1-(3,5-difluorobenzyl)-3-[(3-ethylbenzyl)amino]-2-hydroxypropyl}acetamide (compound 221);

(h) 2-(4-butyl-2,3-dioxopiperazin-1-yl)-N-{(1S,2R)-1-(3,5-difluorobenzyl)-3-[(3-ethylbenzyl)amino]-2-hydroxypropyl}hexanamide (compound 222);

(i) (2S)-N-{(1S,2R)-1-(3,5-difluorobenzyl)-3-[(3-ethylbenzyl)amino]-2-hydroxypropyl}-2-[4-(2-methoxyethyl)piperidin-1-yl]-4-(methylthio)butanamide (compound 223);

(j) (2S)-N-{(1S,2R)-1-(3,5-difluorobenzyl)-3-[(3-ethylbenzyl)amino]-2-hydroxypropyl}-2-[4-(2-methoxyethyl)piperidin-1-yl]hexanamide (compound 224);

(k) (2S)-N-{(1S,2R)-1-(3,5-difluorobenzyl)-3-[(3-ethylbenzyl)amino]-2-hydroxypropyl}-2-[4-(2-methoxyethyl)piperidin-1-yl]pentanamide (compound 225);

(l) (2S)-N-{(1S,2R)-1-(3,5-difluorobenzyl)-3-[(3-ethylbenzyl)amino]-2-hydroxypropyl}-4-(methylthio)-2-(4-propoxypiperidin-1-yl)butanamide (compound 226);

(m) (2S)-N-{(1S,2R)-1-(3,5-difluorobenzyl)-3-[(3-ethylbenzyl)amino]-2-hydroxypropyl}-2-(4-propoxypiperidin-1-yl)hexanamide (compound 227);

(n) (2S)-N-{(1S,2R)-1-(3,5-difluorobenzyl)-3-[(3-ethylbenzyl)amino]-2-hydroxypropyl}-2-(4-propoxypiperidin-1-yl)pentanamide (compound 228);

(o) 2-(4-butyl-2,3-dioxopiperazin-1-yl)-N-((1S,2R)-1-(3,5-difluorobenzyl)-3-{[1-(3-ethylphenyl)cyclopropyl]amino}-2-hydroxypropyl)hexanamide (compound 229);

(p) (2S)-N-((1S,2R)-1-(3,5-difluorobenzyl)-3-{[1-(3-ethylphenyl)cyclopropyl]amino}-2-hydroxypropyl)-2-[4(ethoxymethyl)piperidin-1-yl]-4-(methylthio)butanamide (compound 230);

(q) (2S)-N-((1S,2R)-1-(3,5-difluorobenzyl)-3-{[1-(3-ethylphenyl)cyclopropyl]amino}-2-hydroxypropyl)-2-[4-(ethoxymethyl)piperidin-1-yl]hexanamide (compound 231);

(r) (2S)-N-((1S,2R)-1-(3,5-difluorobenzyl)-3-{[1-(3-ethylphenyl)cyclopropyl]amino}-2-hydroxypropyl)-2-[4-(ethoxymethyl)piperidin-1-yl]pentanamide (compound 232); and (s) N-{(1S,2R)-1-(3,5-difluorobenzyl)-3-[(3-ethylbenzyl) amino]-2-hydroxypropyl}-2-(2,3-dioxo-4-pentylpiperazin-1-yl)acetamide (compound 233).

Biological Examples

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et.al, 1999, Nature 40:537-540) or recombinantly produced as the full-length enzyme (amino acids 1-501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well is transferred to a corresponding anti-MBP antibody coated ELISA plate for capture, containing 80 microliters/well specimen diluent. This reaction is incubated overnight at 4 degrees C. and the ELISA is developed the next day after a 2 hours incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

Biotin-SEVNL-DAEFR[oregon green]KK [SEQ ID NO: 1]
Biotin-SEVKM-DAEFR[oregon green]KK [SEQ ID NO: 2]
Biotin-GLNIKTEEISEISY-EVEFRC[oregon green]KK [SEQ ID NO: 3]
Biotin-ADRGLTTRPGSGLTNIKTEEISEVNL-DAEF[oregon green]KK [SEQ ID NO:4]
Biotin-FVNQHLCoxGSHLVEALY-LVCoxGERGFFYT-PKA[oregon green]KK [SEQ ID NO: 5]

The enzyme (0.1 nanomolar) and test compounds (0.001-100 micromolar) are incubated in pre-blocked, low affinity, black plates (384 well) at 37 degrees C. for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acquerest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an IC50 of less than 50 micromolar.

Example C

Beta-secretase inhibition: P26-P4'SW assay

Synthetic substrates containing the beta-secretase cleavage site of APP are used to assay beta-secretase activity, using the methods described, for example, in published PCT application WO00/47618. The P26-P4'SW substrate is a peptide of the sequence:

```
                                          [SEQ ID NO: 6]
(biotin)CGGADRGLTTRPGSGLTNIKTEEISEVNLDAEF
```

The P26-P1 standard has the sequence:

```
                                          [SEQ ID NO: 7]
(biotin)CGGADRGLTTRPGSGLTNIKTEEISEVNL
```

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with strepavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays using Synthetic Oligopeptide-Substrates

Synthetic oligopeptides are prepared that incorporate the known cleavage site of beta-secretase, and optionally detectable tags, such as fluorescent or chouromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et.al., 1992, $Nature$ 360:672-674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et.al., 1995, $Nature$ 373:523-527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A beta production in human patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

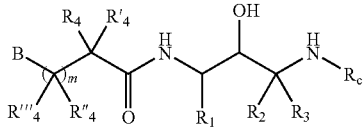

and pharmaceutically acceptable salts thereof wherein m is 0-2;

B is phenyl, which is optionally substituted with one, two, three or four groups independently selected from $R_6$, $R'_6$, $R''_6$ and $R'''_6$;

$R_4$, $R'_4$, $R''_4$ and $R'''_4$ are H;

R and R' independently are —H, —($C_1$-$C_{10}$) alkyl, —($CH_2$)$_{0-4}$—$R_{aryl}$, —($CH_2$)$_{0-4}$—$R_{heteroaryl}$, —($CH_2$)$_{0-4}$—$R_{heterocyclyl}$, or $C_2$-$C_7$ alkenyl or $C_2$-$C_7$ alkynyl, each of which is optionally substituted with one, two or three substituents selected from the group consisting of —F or —OH;

$R_1$ is 3,5-difluorobenzyl;

$R_6$, $R'_6$, $R''_6$, and $R'''_6$ independently are —OR, —NO$_2$, —F, —CO$_2$R, —C≡N, —NRR', —SR, —SO$_2$R, —C(=O)R, —OCF$_3$, —CF$_3$, —CONRR', —SO$_2$NRR', —O—P(=O)(OR)(OR'), —N(R)(COR'), —N(R)(SO$_2$R'), —(CH$_2$)$_{1-4}$—CO—NRR', —(CH$_2$)$_{1-4}$—CO—(C$_1$-C$_{10}$ alkyl), —(CH$_2$)$_{1-4}$—CO—(C$_2$-C$_7$ alkenyl), —(CH$_2$)$_{1-4}$—CO—(C$_2$-C$_7$ alkynyl), —(CH$_2$)$_{0-4}$—$R_{aryl}$, —(CH$_2$)$_{0-4}$—$R_{heteroaryl}$, —(CH$_2$)$_{0-4}$—$R_{heterocycl}$, —(CH$_2$)$_{0-4}$—$R_{aryl}$, —(CH$_2$)$_{0-4}$—CO—$R_{heteroaryl}$, —(CH$_2$)$_{0-4}$—CO—$R_{heterocycl}$, —(CH$_2$)$_{0-4}$—CO—O—$R_{11}$, —(CH$_2$)$_{0-4}$—SO$_2$—NRR', —(CH$_2$)$_{0-4}$—SO$_2$—(C$_1$-C$_{10}$ alkyl), —(CH$_2$)$_{0-4}$—NH—CO—R, —(CH$_2$)$_{0-4}$—N(R$_{11}$) —CO—R, —(CH$_2$)$_{1-4}$—NRR', —(CH$_2$)$_{0-4}$—O—R, or —(CH$_2$)$_{1-4}$—C$_3$-C$_7$ cycloalkyl, or —CH (C$_1$-C$_6$ alkyl)(C$_1$-C$_6$ alkyl), or $C_2$-$C_7$ alkenyl or $C_2$-$C_7$ alkynyl, each of which is optionally sudstituted with one, two or three groups independently selected from —F or —OH;

$R_{11}$ is $C_1$-$C_6$ alkyl, $C_2$-$C_6$ alkenyl, $C_2$-$C_6$ alkynyl, —(CH$_2$)$_{0-2}$—$R_{aryl}$, or —(CH$_2$)$_{0-2}$—$R_{heteroaryl}$;

$R_{aryl}$ is phenyl, 1-naphthyl, 2-naphthyl, indanyl, indenyl, dihydronaphthalyl, or tetralinyl optionally substituted on the aryl ring with one, two, three, or four of the following selected from —F, —Cl, —Br, —I, —NH$_2$, —NH(C$_1$-C$_6$ alkyl), and —N(C$_1$-C$_6$ alkyl), —OH, —C≡N, —SO$_2$—NH$_2$, —SO$_2$—NH—C$_1$-C$_6$ alkyl, —SO$_2$—N(C$_1$-C$_6$ alkyl)$_2$, —SO$_2$—(C$_1$-C$_4$ alkyl), —CO—NH$_2$, —CO—NH—(C$_1$-C$_6$ alkyl), or —CO—N(C$_1$-C$_6$ alkyl)$_2$; or $C_1$-$C_6$ alkyl optionally substituted with one two or three groups independently selected from $C_1$-$C_3$ alkyl, —F, —Cl, —Br, —I, —OH, —SH, —C≡N, —CF$_3$, $C_1$-$C_3$ alkoxy, —NH$_2$, —NH (C$_1$-C$_6$ alkyl), and —N(C$_1$-C$_6$ alkyl)(C$_1$-C$_6$ alkyl); or $C_2$-$C_6$ alkyl with one or two double bonds, optionally substituted with one, two or three groups independently selected from —F, —Cl, —OH, —SH, —C≡N, —CF$_3$, C$_1$-C$_3$ alkoxy, —NH$_2$, —NH(C$_1$-C$_6$ alkyl), and —N(C$_1$-C$_6$alkyl)(C$_1$-C$_6$ alkyl); or $C_2$-$C_6$ alkynyl with one or two triple bonds, optionally substituted with one, two or three groups independently selected from —F, —Cl, —OH, —SH, —C≡N, —CF$_3$, C$_1$-C$_3$ alkoxy, —NH$_2$, —NH(C$_1$-C$_6$ alkyl), and —N(C$_1$-C$_6$ alkyl)(C$_1$-C$_6$ alkyl); or $C_1$-$C_6$ alkoxy optionally substituted with one, two or three of —F;

$R_{heteroaryl}$ is heteroaryl, optionally substituted with one, two, three, or four groups independently selected from —F, —Cl, —Br, —I, —NH$_2$, —NH (C$_1$-C$_6$ alkyl), and —N(C$_1$-C$_6$ alkyl)(C$_1$-C$_6$ alkyl) —OH, —C≡N, —SO$_2$—NH$_2$, —SO$_2$—NH—C$_1$-C$_6$ alkyl, —SO$_2$—N (C$_1$-C$_6$ alkyl)$_2$, —SO$_2$—(C$_1$-C$_4$ alkyl), —CO—NH$_2$, —CO—NH—(C$_1$-C$_6$ alkyl), or —CO—N(C$_1$-C$_6$ alkyl)$_2$; or $C_1$-$C_6$ alykl optionally substituted with one, two or three groups independently selected from $C_1$-$C_3$ alkyl, —F, —Cl, —Br, —I, —OH, —SH, —C≡N, —CF$_3$, $C_1$-$C_3$ alkoxy, —NH$_2$, —NH (C$_1$-C$_6$ alkyl), and —N(C$_1$-C$_6$ alykl)(C$_1$-C$_6$ alkyl); or $C_2$—$C_6$ alkenyl or $C_2$—$C_6$ alkynyl, each of which is optionally substituted with one, two or three groups independently selected from —F, —Cl, —OH, —SH, —C≡N, —CF$_3$, C$_1$-C$_3$ alkoxy, —NH$_2$, —NH(C$_1$-C$_6$ alkyl), and —N(C$_1$-C$_6$ alkyl)(C$_1$-C$_6$ alkyl); or $C_1$-$C_6$ alkoxy optionally substituted with one, two or three of —F;

$R_{heterocyclyl}$ is heterocyclyl optionally substituted with one, two, three, or four groups independently selected from —F, —Cl, —Br, —I, —NH$_2$, —NH(C$_1$-C$_6$ alkyl), and —N(C$_1$-C$_6$ alkyl)(C$_1$-C$_6$ alkyl) —OH, —C≡N, —SO$_2$—NH$_2$, —SO$_2$—NH—C$_1$-C$_6$ alkyl, —SO$_2$—N (C$_1$-C$_6$ alkyl)$_2$, —SO$_2$—(C$_1$-C$_4$ alkyl), —CO—NH$_2$, —CO—NH—(C$_1$-C$_6$ alkyl), —CO—N(C$_1$-C$_6$ alkyl)$_2$ oxo; or $C_1$-$C_6$ alkyl optionally substituted with one, two or three groups independently selected from $C_1$-$C_3$ alkyl, —F, —Cl, —Br, —I, —OH, —SH, —C≡N, —CF$_3$, $C_1$-$C_3$ alkoxy, —NH$_2$, —NH(C$_1$-C$_6$ alkyl), and —N(C$_1$-C$_6$ alkyl)(C$_1$-C$_6$ alkyl); or $C_2$-$C_6$ alkenyl or $C_2$-$C_6$ alkynyl, each of which is optionally substituted with one, two or three groups independently selected from —F, —Cl, —OH, —SH, —C≡N, —CF$_3$, C$_1$-C$_3$ alkoxy, —NH$_2$, —NH(C$_1$-C$_6$ alkyl), and —N(C$_1$-C$_6$ alkyl)(C$_1$-C$_6$ alkyl); or $C_1$-$C_6$ alkoxy optionally substituted with one, two or three of —F;

$R_2$ and $R_3$ are —H;

$R_C$ is phenylmethyl-;

wherein phenyl is optionally substituted with 1, 2, or 3 $R_{200}$; and $R_{200}$ at each occurrence is independently selected from —F, —Cl, —Br, —I, —NH$_2$, —NH(C$_1$-C$_6$ alkyl), and —N(C$_1$-C$_6$ alkyl)(C$_1$-C$_6$ alkyl) —OH, —C≡N, —CO—(C$_1$-C$_4$ alkyl) —SO$_2$—NH$_2$, —SO$_2$—NH—C$_1$-C$_6$ alkyl, —SO$_2$—N(C$_1$-C$_6$ alkyl)$_2$, —SO$_2$—(C$_1$-C$_4$ alkyl), —CO—NH$_2$, —CO—NH—(C$_1$-C$_6$ alkyl), or —CO—N(C$_1$-C$_6$ alkyl)$_2$; —(CH$_2$)$_{1-2}$—C$_3$-C$_7$ cycloalkyl, —(CH$_2$)$_{0-4}$—O—(C$_1$-C$_3$ alkyl) , R$_{aryl}$, and R$_{heterocyclyl}$; or C$_1$-C$_6$ alkyl optionally substituted with one, two or three groups independently selected from C$_1$-C$_3$ alkyl, —F, —Cl, —Br, —I, —OH, —SH, —C≡N, —CF$_3$, C$_1$-C$_3$ alkoxy, —NH$_2$, —NH(C$_1$-C$_6$ alkyl), and —N(C$_1$-C$_6$ alkyl)(C$_1$-C$_6$ alkyl); or C$_2$-C$_6$ alkenyl with one or two double bonds; or C$_2$-C$_6$ alkynyl with one or two triple bonds; or C$_2$-C$_6$ alkyl chain with one double and one triple bond; or C$_2$-C$_6$ alkenyl or C$_2$-C$_6$ alkynyl, each of which is optionally substituted with one, two or three groups independently selected from —F, —Cl, —OH, —SH, —C≡N, —CF$_3$, C$_1$-C$_3$ alkoxy, —NH$_2$, —NH(C$_1$-C$_6$ alkyl), and —N(C$_1$-C$_6$ alkyl)(C$_1$-C$_6$ alkyl); or C$_3$-C$_7$ cycloalkyl, optionally substituted with one, two or three substituents selected from the group consisting of —F, —Cl, —OH, —SH, —C≡N, —CF$_3$, C$_1$-C$_3$ alkoxy, —NH$_2$, —NH(C$_1$-C$_6$ alkyl), and —N(C$_1$-C$_6$ alkyl)(C$_1$-C$_6$ alkyl); or C$_1$-C$_6$ alkoxy optionally substituted with one, two or three of —F.

2. A compound according to claim 1 wherein

B is phenyl, which is substituted with one or two —OH, and one or two groups independently selected from R$_6$, R'$_6$, and —O—C$_1$ alkyl.

3. A compound according to claim 1 wherein

R$_C$ is phenylmethyl-, where the phenyl is optionally substituted with halogen or —C$_1$-C$_6$ alkyl.

4. A compound according to claim 3 wherein m is 0.

5. A compound according to claim 1 which is selected from

N-{(1S,2R)-1-(3,5-difluorobonzyl)-2-hydroxy-3-[(3-iodobonzyl)amino]propyl}-2-{4-[(methylsulfonyl)amino]phenyl}acetamide;

N-{(1S,2R)-1-(3,5-difluorobonzyl)-2-hydroxy-3-[(3-iodobonzyl)amino]propyl}-2-{4-[2-(4-methylpiperazin-1-yl)ethoxy]phenyl}acetamide;

N-{(1S,2R)-1-(3,5-difluorobenzyl)-2-hydroxy-3-[(3-iodobenzyl)amino]propyl}-4-(4-phenoxyphenyl)butanamide;

N-{(1S,2R)-1-(3,5-diflourobenzyl)-2-hydroxy-3-[(3-iodobenzyl)amino]propyl}-2-(4-phenoxyphenyl)acetamide;

N-[(1S,2R)-3-(benzylamino)-1-(3,5difluorobenzyl)-2-hydroxypropyl]-3-phenyipropanamide;

N-{(1S,2R)-1-(3,5-difluorobenzyl)-2-hydroxy-3-[(3-methoxybenzyl)amino]propyl}-3-phenylpropanamide;

N-{(1S,2R)-1-(3,5-difluorobenzyl)-2-hydroxy-3-[(4-methylbenzyl)amino]propyl}-2-(4-isopropyiphenyl)acetamide;

N-[(1S,2R)-3-(benzylamino)-1-(3,5-difluorobenzyl)-2-hydroxypropyl]-2-(4-isopropyiphenyl)acetamide;

N-{(1S,2R)-1-(3,5-difluorobenzyl)-2-hydroxy-3-[4-(methylbenzyl)amino]propyl}-2-[4-(methylthio)phenyl]acetamide;

N-[(1S, 2R -3-(benzylamino)-1-(3,5-difluorobenzyl)-2-hydroxypropyl]-2-[4-(methylthio)phenyl]acetamide;

N-{(1S, 2R)-1-(3,5-difluorobenzyl)-2-hydroxy-3-[(3-methoxybenzyl)amino]propyl}-2-(4-isopropyiphenyl)acetamide;

N-{(1S, 2R)-1-(3,5-difluorobenzyl)-2-hydroxy-3-[(3-iodobenzyl)amino]propyl}-2-(4-isopropyiphenyl)acetamide;

N-{(1S, 2R)-1-(3,5-difluorobenzyl)-2-hydroxy-3-[(3-methoxybenzyl) amino]propyl}-2-[4-(methylthio)phenyl]acetamide;

N-{(1S,2R)-1-(3,5-difluorobenzyl)-2-hydroxy-3-[(3-iodobenzyl)amino]propyl}-2-[4-(methylthio)phenyl]acetamide;

N-{(1S, 2R)-1-(3,5-difluorobenzyl)-2-hydroxy-3-[(3-iodobenzyl)amino]propyl}-3-(2-fluorophenyl)propanamide;

N-{(1S, 2R)-1-(3,5-difluorobenzyl)-3-[(3-ethylbenzyl)amino]-2-hydroxypropyl}-3-{4-[(methylsulfonyl)amino]phenyl}propanamide;

N-{(1S,2R)-1-(3,5-difluorobenzyl)-3-[(3-ethylbenzyl)amino]-2-hydroxypropyl}-2-phenylacetamide;

N-{(1S, 2R)-1-(3,5-difluorobenzyl)-3-[(3-ethylbenzyl)amino]-2-hydroxypropyl}-2-(3-fluoro-4-propoxyphenyl)acetamide;

N-{(1S,2R)-1-(3,5difluorobenzyl)-3-[(3-ethylbenzyl)amino]-2-hydroxypropyl}-2-(3-methoxy-4-propoxyphenyl) acetamide;

N-{(1S, 2R)-1-(3,5-difluorobenzyl)-3-[(3-ethylbenzyl)amino]-2-hydroxypropyl}-2-(4-ethoxyphenyl)acetamide;

N-{(1S, 2R)-1-(3,5difluorobenzyl)-3-[(3-ethylbenzyl)amino]-2-hydroxypropyl}-2-(3-hydroxy-4-methoxyphenyl)acetamide;

N-{(1S, 2R)-1-(3,5-difluorobenzyl)-2-hydroxy-3-[(3-methoxybenzyl)amino]propyl}-3-phenyipropanamide; and N-{(1S, 2R)-1-(3,5difluorobenzyl)-3-[(3-ethylbenzyl)amino]-2-hydroxypropyl}-3-phenyipropanamide.

6. A method of treating a patient who has a disease or condition selected from the group consisting of Alzheimer's disease, mild cognitive impairment (MCI), Down's syndrome, humans who have Hereditary Cerebral Hemorrhage with Amyloidosis of the Dutch-Type, cerebral amyloid angiopathy, frontotemporal dementias with Parkinsonism (FTDP), dementias of mixed vascular and degenerative origin, dementia associated with Parkinson's disease, dementia associated with progressive supranuclear palsy, dementia associated with cortical basal degeneration, and diffuse Lewy body type of Alzheimer's disease, the method comprising administering a therapeutically effective amount of a compound of claim 1 to a patient in need of such treatment.

7. A method of treatment according to claim 6 where the therapeutically effective amount for oral administration is from about 0.1 mg/day to about 1,000 mg/day; for parenteral, sublingual, intranasal, intrathecal administration is from about 0.5 to about 100 mg/day; for depo administration and implants is from about 0.5 mg/day to about 50 mg/day; for topical administration is from about 0.5 mg/day to about 200 mg/day; for rectal administration is from about 0.5 mg to about 500 mg.

* * * * *

UNITED STATES PATENT AND TRADEMARK OFFICE
CERTIFICATE OF CORRECTION

| | | |
|---|---|---|
| PATENT NO. | : 7,589,094 B2 | Page 1 of 1 |
| APPLICATION NO. | : 11/296669 | |
| DATED | : September 15, 2009 | |
| INVENTOR(S) | : Gailunas et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this
Sixteenth Day of August, 2011

David J. Kappos
*Director of the United States Patent and Trademark Office*

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
```

```
<223> OTHER INFORMATION: covalent attachment of oregon green

<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15
Glu Phe Arg Cys Lys Lys
            20

<210> SEQ ID NO 4
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15
Lys Thr Glu Glu Ile Ser Glu Val Asn Leu Asp Ala Glu Phe Arg Cys
            20                  25                  30
Lys Lys

<210> SEQ ID NO 5
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green
```

```
<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Cys Lys
            20                  25                  30

Lys

<210> SEQ ID NO 6
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial sequence
<220> FEATURE:
<223> OTHER INFORMATION: synthetic peptide

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial sequence
<220> FEATURE:
<223> OTHER INFORMATION: synthetic peptide

<400> SEQUENCE: 9

Ala Asp Arg Gly Leu Thr Thr Arg Pro Gly Ser Gly Leu Thr Asn Ile
1               5                   10                  15
```

-continued

```
Lys Thr Glu Glu Ile Ser Glu Val Asn Leu Asp Ala Glu Phe
         20                  25                  30
```